United States Patent
Hoshina et al.

(10) Patent No.: US 7,335,673 B2
(45) Date of Patent: Feb. 26, 2008

(54) 2,3-DIPHENYLPROPIONIC ACID DERIVATIVES OR THEIR SALTS, MEDICINES OR CELL ADHESION INHIBITORS CONTAINING THE SAME, AND THEIR USAGE

(75) Inventors: Yoichiro Hoshina, Kyoto (JP); Satoru Ikegami, Kyoto (JP); Akihiko Okuyama, Kyoto (JP); Tatsuhiro Harada, Kyoto (JP); Atsushi Matsuo, Shizuoka (JP)

(73) Assignee: Kaken Pharmaceutical Co., Ltd. (JP)

( * ) Notice: Subject to any disclaimer, the term of this patent is extended or adjusted under 35 U.S.C. 154(b) by 594 days.

(21) Appl. No.: 10/344,105

(22) PCT Filed: Aug. 10, 2001

(86) PCT No.: PCT/JP01/06934

§ 371 (c)(1),
(2), (4) Date: Aug. 19, 2003

(87) PCT Pub. No.: WO02/14262

PCT Pub. Date: Feb. 21, 2002

(65) Prior Publication Data

US 2004/0072878 A1  Apr. 15, 2004

(51) Int. Cl.
| A61K 31/44 | (2006.01) |
| A61K 31/385 | (2006.01) |
| A61K 31/34 | (2006.01) |
| A61K 31/38 | (2006.01) |
| C07D 211/78 | (2006.01) |

(52) U.S. Cl. ............... 514/354; 514/616; 514/461; 514/438; 514/354; 514/439; 546/322; 548/195; 562/496

(58) Field of Classification Search ............... 562/496; 514/616, 461, 438, 354, 439; 549/487; 546/322; 548/195
See application file for complete search history.

(56) References Cited

U.S. PATENT DOCUMENTS

| 2,345,384 A | 3/1944 | Dohrn et al. |
| 2,552,696 A | 5/1951 | Tullar et al. |
| 2,606,922 A | 8/1952 | Papa et al. |
| 3,483,293 A | 12/1969 | Duncan et al. |
| 3,991,201 A | 11/1976 | Heeres et al. |

FOREIGN PATENT DOCUMENTS

| DE | 1811825 | 7/1969 |
| DE | 1811825 A1 | 7/1969 |
| EP | 325245 | 7/1989 |
| EP | 325245 A1 | 7/1989 |
| GB | 867538 | 5/1961 |
| GB | 1 555 849 | 11/1979 |
| JP | 50-95261 | 7/1975 |
| JP | 57-31640 | 2/1982 |
| JP | 57-31640 A | 2/1982 |
| JP | 3-135914 | 6/1991 |
| JP | 3-135914 A | 6/1991 |
| JP | 50-95261 A | 2/1995 |
| WO | 9503295 | * 2/1995 |
| WO | WO 95/03295 | 2/1995 |
| WO | WO 95/03295 A1 | 2/1995 |
| WO | WO 00/40548 | 7/2000 |
| WO | WO 00/40548 A1 | 7/2000 |
| WO | WO 01/14362 | 3/2001 |
| WO | WO 01/14362 A1 | 3/2001 |

OTHER PUBLICATIONS

Camps et. al., "Deracemization of alpha-Substituted Arylacetic Acids", Tetahedron: Asymmetry, vol. 7, No. 4, pp. 1227-1234, 1996.*
Camps, Pelayo et al., Tetrahedron: Asymmetry, 7(4):1227-1234 (1996).
Greifenstein Linda G. et al., J. Org. Chem., 46:5125-5132 (1981).
Lednicer, Daniel et al., Journal of Medicinal Chemistry, 8:52-57 (1965).
Lewis, T.R. et al., Journal of the American Chemical Society, 71(11):3749-3752 (1949).
Schorr, Von Manfred et al., Arzneitmittel Forschung, 14(10):1151-1156 (1964).
Walker, Gordon N., Journal of Medicinal Chemistry, 8:583-588 (1965).
Biochem J. (1993) 289, 185-193.
Mock, et al. "Fluxionate Lewis acidity of the zinc (2+) ion in carboxypeptidase A", Biochim. J. 289(1):185-193 (1993).

* cited by examiner

Primary Examiner—Janet L. Andres
Assistant Examiner—Binta Robinson
(74) Attorney, Agent, or Firm—Nixon Peabody LLP

(57) ABSTRACT

A 2,3-diphenylpropionic acid derivatives or the salts represented by general formula (1) below; and pharmaceutical compositions and cell adhesion inhibitors comprising the derivatives or the salts as the active ingredient. In the formula, A, B and C independently represents a hydrogen atom or a monovalent substituent; and X and X' independently represents a hydrogen atom or a monovalent substituent

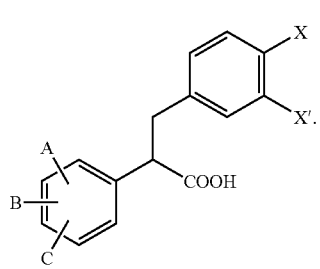

Formula (1)

10 Claims, No Drawings

2,3-DIPHENYLPROPIONIC ACID DERIVATIVES OR THEIR SALTS, MEDICINES OR CELL ADHESION INHIBITORS CONTAINING THE SAME, AND THEIR USAGE

TECHNICAL FIELD

The present invention relates to novel 2,3-diphenylpropionic acid derivatives or salts thereof, a pharmaceutical composition and a cell adhesion inhibitor containing any of which as an active ingredient.

RELATED ART

Adhesion is an indispensable process for a complex life phenomenon resulted from intercellular interaction such as cell activation, migration, proliferation, and differentiation. Cell adhesion molecules are known to be involved in such cell-cell interaction or cell-extracellular matrix interaction, which molecules are typically classified into integrins, immunoglobulin, selectins and cadherins. The integrin family has an αβ-heterodimer structure, and 16 different α-chains and 8 different β-chains have been identified. One of them, integrins VLA-4 (α4β1), is known to be expressed within lymphocyte, eosinophils, basophils and monocyte, where VCAM-1 and fibronectins acts as ligand therefor. That is, VLA-4 plays an important role in cell-cell interaction and cell-extracellular matrix interaction mediated by VCAM-1 and fibronectins. On the other hand, integrins LPAM-1 (α4β7) is known to be expressed within lymphocyte, eosinophils, basophils and monocyte, where VCAM-1, fibronectins and MadCAM-1 act as ligands. In order to function in the inflammatory tissue, leukocytes circulating with blood should pass thorough the vascular endothelial cells and be invade the inflammatory portion. Binding of either VLA-4 or LPAM-1 with either VCAM-1 or MadCAM-1 is one of the most important mechanism of ensuring a strong adhesion between leukocytes and vascular endothelial cells. Inflammatory cells such as T-lymphocyte, B-lymphocyte, monocyte and eosinophils are known to express VLA-4 and LPAM-1, which strongly relate to infiltration of these cells into the inflammatory lesion. The adhesion molecules play an important role also in the activation of cells as being mediated by intercellular interaction, where has been made clear that the VLA-4/VCAM-1 mechanism activates eosinophils to thereby bring about degranulation, and that a signal mediated by VLA-4 also relates to antigen-specific activation and proliferation of lymphocyte.

In order to clarify roles of VLA-4 and LPAM-1 in inflammation or so, several studies have been made on inhibition of this intermolecular binding using monoclonal antibody. For example, anti-α4 monoclonal antibody is known to inhibit adhesion of VLA-4-expressing Ramos cells onto human umbilical venous endothelial cells (HUVEC) or VCAM-1-gene-introduced COS cells. The antibody was successful in exhibiting therapeutic or prophylactic effects in several animal models. For example, significant of effects were shown in rat adjuvant induced arthritis model (Barbadillo et al., *Arthr Rheuma.*, 1993, 36, 95), contact hypersensitivity and delayed hypersensitivity model (Ferguson and Kupper, *J. Immunol.*, 1993, 150, 1172; Chisholm et al., *Eur. J. Immunol.*, 1993, 23, 682). The action of the antibody was also assessed in an experimental autoimmune encephalomyelitis (Yednock, *Nature*, 1992, 356, 63), asthma model (Abraham et al., *J. Clin. Invest.*, 1993, 93, 776), and inflammatory bowel disease (IBD) model (Podolsky et al., *J. Clin. Invest.*, 1993, 92, 372). Still other studies revealed that cell adhesion by VLA-4 plays some roles also in rheumatoid arthritis, nephritis, diabetes, systemic lupus erythematosus, delayed allergy, multiple sclerosis, arteriosclerosis, organ transplantation and various malignant tumor.

It is therefore apparent that blocking of VLA-4 (α4β) and/or LPAM-1 (α4β7) integrins using an appropriate antagonist is effective for treatment of inflammatory diseases and various diseases listed in the above.

Several low molecular weight chemical compounds have already been proposed as VLA-4 and/or LPAM-1 antagonists, which are found in International Patent Publication Nos. WO96/22966, WO98/53817, WO01/14328, WO99/06431, WO99/06432, WO99/06436, WO99/10312, WO99/48879, WO00/18759, WO00/20396, WO99/36393, WO99/52898 and WO00/67746. All compounds described in these publications have either of an urea structure or phenylalanine structure, and are different from the compounds of the present invention having a diphenylpropionic acid structure. All conventional compounds also suffer from problems of lack of bio-availability through oral administration and biodegradation. Therefore there is a strong need for a novel compound having an antagonistic action against VLA-4 and/or LPAM-1, and thus have a preferable profile for use as a remedy or prophylactic.

In view of prophylactic or therapeutic treatment of diseases mediated by VLA-4 and/or LPAM-1, it is an object of the present invention to provide novel 2,3-diphenylpropionic acid derivatives or salts thereof having an antagonistic action against VLA-4 and/or LPAM-1, an excellent oral absorption and pharmacokinetics. It is another object of the present invention to provide a VLA-4 and/or LPAM-1 antagonist and a medicine useful in prophylactic or therapeutic treating of diseases mediated by VLA-4 and/or LPAM-1.

DISCLOSURE OF THE INVENTION

After extensive investigations to solve the above-described problems, the present inventors found out that 2,3-diphenylpropionic acid derivatives has an excellent inhibition against α4 integrins, which led us to complete the present invention.

The above mentioned object of the present invention can be achieved by a 2,3-diphenylpropionic acid derivative or a salt thereof represented by general formula (1) below:

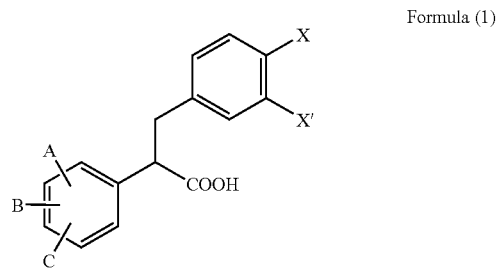

Formula (1)

where, A, B and C independently represent a hydrogen atom, halogen atom, nitro, cyano, hydroxy, carboxy, $C_{1-15}$ alkyl group, $C_{6-10}$ aryl group, heteroaryl group, $C_{1-15}$ alkoxy group, $C_{6-10}$ aryloxy group, heteroaryloxy group, $C_{2-16}$ alkoxycarbonyl group, $C_{7-11}$ aryloxycarbonyl group, heteroaryloxycarbonyl group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, $C_{1-15}$ alkylsulfonyl group, $C_{6-10}$ arylsulfonyl group, heteroarylsulfonyl group, $C_{1-15}$ alkylsulfinyl group, $C_{6-10}$ arylsulfinyl group, heteroarylsulfinyl group, —$NR^1R^2$, —$NR^1COR^2$, —$NR^1SO_2R^2$, —$NR^1CONR^2R^3$ or —$CONR^1R^2$ (where, $R^1$, $R^2$ and $R^3$ independently represent a hydrogen atom, $C_{1-15}$ alkyl group, $C_{2-15}$ alkenyl group, $C_{1-15}$ alkoxy group, $C_{6-10}$ aryl group, $C_{6-10}$ aryloxy group, heteroaryloxy group or heteroaryl group; either $R^1$ and $R^2$ or $R^2$ and $R^3$ may respectively form a ring; said ring may additionally contain at least one ring-composing atom selected from oxygen atom, nitrogen atom and sulfur atom; said ring may contain a double bond; and said ring may have a substituent); any two of A, B and C bound on the adjacent carbon atoms may form a benzene ring or methylenedioxy ring; X and X' independently represent a hydrogen atom, halogen atom, nitro, cyano, hydroxy, carboxy, $C_{1-15}$ alkyl group, $C_{2-15}$ alkenyl group, $C_{2-15}$ alkynyl group, $C_{6-10}$ aryl group, heteroaryl group, $C_{1-15}$ alkoxy group, $C_{6-10}$ aryloxy group, heteroaryloxy group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, —$NR^4R^5$, —$NR^4COR^5$, —$NR^4SO_2R^5$, —$NR^4CONR^5R^6$, —$OCONR^4R^5$ or —$CONR^4R^5$ (where, $R^4$, $R^5$ and $R^6$ independently represent a hydrogen atom, $C_{1-15}$ alkyl group, $C_{2-15}$ alkenyl group, $C_{6-10}$ aryl group, $C_{1-15}$ alkoxy group, $C_{6-10}$ aryloxy group, heteroaryloxy group or heteroaryl group; either $R^4$ and $R^5$ or $R^5$ and $R^6$ may form a ring; said ring may additionally contain at least one ring-composing atom selected from oxygen atom, nitrogen atom and sulfur atom; said ring may contain a double bond; and said ring may have a substituent).

As one embodiment of the present invention, there is provided the 2,3-diphenylpropionic acid derivative or the salt thereof, wherein at least one of X and X' in the general formula (1) is represented by any one of general formulae (2) to (5) below:

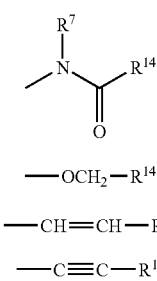

Formula (2)

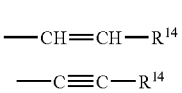

Formula (3)

—$OCH_2$—$R^{14}$

Formula (4)

—$CH\!=\!CH$—$R^{14}$

Formula (5)

—$C\!\equiv\!C$—$R^{14}$ where $R^7$ represents a hydrogen atom or $C_{1-15}$ alkyl group, and $R^{14}$ represents either of groups represented by general formulae (6) and (7);

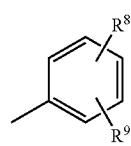

Formula (6)

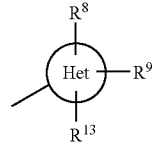

Formula (7)

where, $R^8$ and $R^9$ independently represent a hydrogen atom, halogen atom, nitro, cyano, hydroxy, carboxy, $C_{1-15}$ alkyl group, $C_{6-10}$ aryl group, $C_{1-15}$ alkoxy group, $C_{6-10}$ aryloxy group, heteroaryloxy group, $C_{2-16}$ alkoxycarbonyl group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, $C_{1-15}$ alkylsulfonyl group, $C_{6-10}$ arylsulfonyl group, heteroarylsulfonyl group, $C_{1-15}$ alkylsulfinyl group, $C_{6-10}$ arylsulfinyl group, heteroarylsulfinyl group, —$NR^{10}R^{11}$, —$NR^{10}COR^{11}$, —$NR^{10}SO_2R^{11}$, —$NR^{10}CONR^{11}R^{12}$ or —$CONR^{10}R^{11}$ (where, $R^{10}$, $R^{11}$ and $R^{12}$ independently represent a hydrogen atom, $C_{1-15}$ alkyl group, $C_{2-15}$ alkenyl group, $C_{1-15}$ alkoxy group, $C_{6-10}$ aryl group, $C_{6-10}$ aryloxy group, heteroaryloxy group or heteroaryl group; either $R^{10}$ and $R^{11}$ or $R^{11}$ and $R^{12}$ may form a ring; said ring may additionally contain at least one ring-composing atom selected from oxygen atom, nitrogen atom and sulfur atom; said ring may contain a double bond; and said ring may have a substituent); Het represents an aromatic heterocycle containing at least one atom selected from nitrogen atom, oxygen atom and sulfur atom; and $R^{13}$ represents a hydrogen atom or $C_{1-15}$ alkyl group.

As one prefer embodiment, there are provided the 2,3-diphenylpropionic acid derivative or the salt thereof wherein at least one of A, B and C in the formula (1) represents —$NR^1R^2$, —$NR^1COR^2$, —$NR^1SO_2R^2$ or —$NR^1CONR^2R^3$; and at least one of X and X' represents an atom or group other than hydrogen atom; the 2,3-diphenylpropionic acid derivative or the salt thereof wherein at least one of A, B and C in the formula (1) represents a $C_{1-15}$ alkyl group, $C_{1-15}$ alkoxy group, $C_{6-10}$ aryl group, heteroaryl group or $C_{2-16}$ alkoxycarbonyl group; and at least one of X and X' represents an atom or group other than hydrogen atom; and the 2,3-diphenylpropionic acid derivative or the salt thereof wherein at least one of A, B and C in the formula (1) represents a halogen atom, cyano or $C_{1-15}$ alkylthio group; and at least one of X and X' represents an atom or group other than hydrogen atom.

As more prefer embodiment of the present invention, there are provided the 2,3-diphenylpropionic acid derivative or the salt thereof wherein "A" represents —$NR^1COR^2$ substituted at the 3-position; X represents an atom or group other than hydrogen atom; and X' represents a hydrogen atom; and as furthermore prefer embodiment, the 2,3-diphenylpropionic acid derivative or the salt thereof wherein "A" represents —$NR^1COR^2$ substituted at the 3-position; B represents a $C_{1-15}$ alkyl group or $C_{1-15}$ alkoxy group substituted at the 4- or 5-position; X' represents a hydrogen atom; and X represents a halogen atom, nitro, cyano, hydroxy, $C_{6-10}$ aryl group, heteroaryl group, $C_{1-15}$ alkoxy group, —$NR^4R^5$, —$NR^4COR^5$, —$NR^4SO_2R^5$, —$NR^4CONR^5R^6$, —$OCONR^4R^5$ or —$CONR^4R^5$.

And the above mentioned object of the present invention can be achieved by a pharmaceutical composition comprising as an active ingredient thereof the 2,3-diphenylpropionic acid derivatives or the salt thereof; a pharmaceutical composition for prophylactic or therapeutic treatment of inflammatory disease related to cell adhesion, comprising as an active ingredient the 2,3-diphenylpropionic acid derivative or the salt thereof; a pharmaceutical composition for prophylactic or therapeutic treatment of inflammatory disease related to cell adhesion mediated by α4 integrins, comprising as an active ingredient the 2,3-diphenylpropionic acid derivative or the salt thereof; a cell adhesion inhibitor comprising as an active ingredient the 2,3-diphenylpropionic acid derivative or the salt thereof; an α4 integrin inhibitor comprising as an active ingredient the 2,3-diphenylpropionic acid derivative or the salt thereof; a VLA-4 and/or LPAM-1 antagonist comprising as an active ingredient the 2,3-diphenylpropionic acid derivative or the salt thereof.

And the above mentioned object of the present invention can be achieved by a method of using as a pharmaceutical composition the 2,3-diphenylpropionic acid derivative or the salt thereof; a method of using as an α4 integrins inhibitor the 2,3-diphenylpropionic acid derivative or the salt thereof.

MODES FOR CARRYING OUT THE INVENTION

It is to be noted that, in this specification, a range of the number of carbon atoms is defined as denoting that for the individual groups having no substituent, and is not inclusive of the number of carbon atoms ascribable to any substituent portion (for example, for the case of an alkyl group substituted with an aryl group, (arylalkyl group), the number of carbon atoms denotes the number of carbon atoms composing the alkyl portion composing such arylalkyl group, not inclusive of the number of carbon atoms composing the aryl portion).

First, 2,3-diphenylpropionic acid derivatives represented by the formula (1) will be explained.

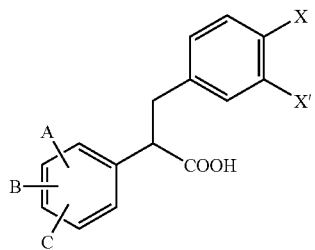

Formula (1)

In the formula (1), A, B and C independently represent a hydrogen atom, halogen atom, nitro, cyano, hydroxy, carboxy, $C_{1-15}$ alkyl group, $C_{6-10}$ aryl group, heteroaryl group, $C_{1-15}$ alkoxy group, $C_{6-10}$ aryloxy group, heteroaryloxy group, $C_{2-16}$ alkoxycarbonyl group, $C_{7-11}$ aryloxycarbonyl group, heteroaryloxycarbonyl group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, $C_{1-15}$ alkylsulfonyl group, $C_{6-10}$ arylsulfonyl group, heteroarylsulfonyl group, $C_{1-15}$ alkylsulfinyl group, $C_{6-10}$ arylsulfinyl group, heteroarylsulfinyl group, $-NR^1R^2$, $-NR^1COR^2$, $-NR^1SO_2R^2$, $-NR^1CONR^2R^3$ or $-CONR^1R^2$.

Specific examples of the halogen atom include fluorine atom, chlorine atom, bromine atom and iodine atom.

The foregoing $C_{1-15}$ alkyl group includes non-substituted alkyl group and substituted alkyl group, where the alkyl chain may be straight or branched, and may be a cycloalkyl group having one or more cyclic structure (the term "alkyl group" in this specification will be used in this meaning unless otherwise specifically be noted). The alkyl group includes straight and branched ones, examples of which include $C_{1-15}$ non-substituted alkyl group, and specific examples of which include methyl, ethyl, n-propyl, isopropyl, n-butyl, isobutyl, tert-butyl, sec-butyl, n-pentyl, tert-amyl, 3-methylbutyl, neopentyl, n-hexyl and n-decyl. The alkyl group also include $C_{3-15}$ cycloalkyl group, specific examples of which include cyclopropyl, cyclobutyl, cyclopentyl, cyclohexyl and cycloheptyl.

For the case where the alkyl group has any substituent, such substituent can typically be exemplified by a halogen atom, nitro, cyano, hydroxy, carboxy, $C_{6-10}$ aryl group, heteroaryl group, $-OR$, $-SR$, $-SOR$, $-SO_2R$ and $-NRR'$ [in this specification, the same substituents will apply also to those for the alkyl group portion of the alkyl-group-containing substituent (e.g., alkoxy group and alkylthio group) unless otherwise specifically be noted]. R and R' herein independently represent a hydrogen atom, $C_{1-10}$ alkyl group, $C_{2-10}$ alkenyl group, $C_{6-10}$ aryl group or heteroaryl group. For the case where the alkyl group is a halogenoalkyl group having a halogen atom as a substituent, such halogenoalkyl group can be exemplified by $C_{1-15}$ groups, where specific examples of which include trichloromethyl, trifluoromethyl, 1-chloroethyl and 2,2,2-trifluoroethyl. For the case where the alkyl group is substituted by an aryl group, the aryl group can be exemplified by $C_{6-10}$ non-substituted or 1- to 3-substituted monocyclic or bicyclic aryl groups, where specific examples of which include benzyl, 2-phenethyl, 1-phenethyl, 1-phenylpropyl, 1-naphthylmethyl and 2-naphthylmethyl. The aryl portion of the arylalkyl group may further be substituted, where examples of the substituent in this case include $C_{1-6}$ alkyl group, $C_{1-7}$ alkoxy group, halogen atom, nitro, cyano, hydroxy, carboxy, $C_{6-10}$ aryl group and $C_{6-10}$ aryloxy group.

For the case where the alkyl group is a heteroarylalkyl group having a heteroaryl group as a substituent, specific examples of which include 2-pyridylmethyl, 3-furylmethyl and 2-(2-thienyl)ethyl. On the other hand for the case the alkyl group is an alkoxyalkyl group having an alkoxy group as a substituent, the alkoxy group may be $C_{1-10}$ alkoxy group, where specific examples of which include methoxymethyl, ethoxymethyl, isopropoxymethyl, 2-methoxyethyl and 1-methoxyisopropyl.

The foregoing substituted alkyl group include $-(CH_2)_n-NRR'$, $-(CH_2)_n-OR$, $-(CH_2)_n-SR$, $-(CH_2)_n-SOR$ or $-(CH_2)_n-SO_2R$. It is to be noted that "n" represents any of integer from 1 to 3; and R and R' are same as those defined in the above, where specific examples of which are also same.

The $C_{6-10}$ aryl group includes both of non-substituted aryl group and substituted aryl group (in this specification, the term "aryl group" is used in this meaning unless otherwise specifically be noted). The aryl group includes $C_{6-10}$ non-substituted aryl group, where specific examples of which include phenyl, 1-naphthyl and 2-naphthyl.

For the case where the aryl group is substituted by any substituent, such substituent may typically be exemplified by $C_{1-10}$ alkyl group, halogen atom, nitro, cyano, hydroxy, carboxy, $C_{6-10}$ aryl group, heteroaryl group, $-OR$, $-NRR'$, $-SR$, $-SOR$ and $-SO_2R$ (in this specification, the same substituents will apply also to those for the aryl group portion of the aryl group-containing substituent (e.g., aryloxy group, arylthio group,) unless otherwise specifically be noted). R and R' are same as those defined in the above, where specific examples of which are also same. The substituted aryl group can typically exemplified by o-tolyl, 2,6-dimethoxyphenyl, 3-chlorophenyl, 2-cyanophenyl and biphenyl.

The foregoing heteroaryl group refers to a group comprising an aromatic heterocycle which contains at least one hetero atom selected from nitrogen atom, oxygen atom and sulfur atom, where such heteroaryl group includes both of non-substituted heteroaryl group and substituted heteroaryl group (in this specification, the "heteroaryl group" is used in this meaning unless otherwise specifically be noted). For the case where the heteroaryl group has any substituent, examples of such substituent include halogen atom, nitro, cyano, hydroxy, carboxy, the above-described alkyl group, the above-described aryl group, —OR, —NRR', —SR, —SOR and —SO$_2$R [in this specification, the same substituents will apply also to the heteroaryl group portion of the heteroaryl-group-containing substituent (e.g., heteroaryloxy group, heteroarylthio group,) unless otherwise specifically be noted]. R and R' are same as those defined in the above, where specific examples of which are also same.

Specific examples of the heteroaryl group include furyl, thienyl, imidazolyl, thiazolyl, oxazolyl, isoxazolyl, pyridyl, pyrazyl, indolyl, tetrazolyl and quinolyl.

The foregoing $C_{1-15}$ alkoxy group includes both of non-substituted alkoxy group and substituted alkoxy group, where alkyl groups possibly composing the alkoxy group are same with the foregoing alkyl groups (the term "alkoxy group" in this specification is used for this meaning unless otherwise being specifically noted), and the same will apply to any substituents in the alkyl group portion and specific examples thereof. The foregoing alkoxy groups include straight-chained or branched ones which include $C_{1-15}$ non-substituted alkoxy groups, where specific examples thereof include methoxy, ethoxy, n-propoxy, isopropoxy, n-butoxy, isobutoxy, tert-butoxy, sec-butoxy, n-pentyloxy, tert-amyloxy, neopentyloxy and n-hexyloxy.

For the case where the foregoing alkoxy group is alkoxyalkoxy group having an alkoxy group as a further substituent, specific examples thereof include methoxy methoxy and methoxy ethoxy methoxy. On the other hand, for the case where the foregoing alkoxy group is arylalkoxy group having an aryl group as a substituent, the aryl group can be exemplified by $C_{6-10}$ ones, where specific examples of the arylalkoxy group include benzyloxy, 1-naphthylmethoxy, 2-naphthylmethoxy, 1-phenylethoxy, 4-methoxybenzyloxy, 2-phenylethoxy, 3-phenylpropoxy. Further for the case where the foregoing alkoxy group is heteroarylalkoxy group having a heteroaryl group as a substituent, specific examples of the heteroarylalkoxy group include 2-pyridylmethoxy, (3,5-dichloropyrido-4-yl)methoxy and 2-(indole-1-yl) ethoxy.

The foregoing $C_{6-10}$ aryloxy group includes both of non-substituted aryloxy group and substituted aryloxy group. Aryl groups possibly composing the aryloxy group are same with the foregoing aryl groups (the term "aryloxy group" in this specification is used for this meaning unless otherwise being specifically noted), and the same will apply to any substituents in the aryl group portion and specific examples thereof. The aryloxy group includes $C_{6-10}$ non-substituted aryloxy group, where specific examples of which include phenoxy and naphthoxy. Specific examples of the substituted aryloxy group include 2-chlorophenoxy.

The heteroaryloxy group includes both of non-substituted heteroaryloxy group and substituted heteroaryloxy group, where heteroaryl group possibly composing the heteroaryloxy group are the same as those defined in the above (the term "heteroaryloxy group" in this specification is used in this meaning unless otherwise specifically be noted), and the same will apply also to any substituents in the heteroaryl group portion, where specific examples of which are also same. Specific examples of the heteroaryloxy group include 4-pyridyloxy and 2-pyrimidyloxy.

The $C_{2-16}$ alkoxycarbonyl group includes both of non-substituted alkoxycarbonyl group and substituted alkoxycarbonyl group, where the alkyl group possibly composing the alkoxycarbonyl group are same as those defined in the above (the term "alkoxycarbonyl group" in this specification is used in this meaning unless otherwise specifically be noted), and the same will apply also to any substituents in the alkyl group portion, where specific examples of which are also same. Specific examples of the alkoxycarbonyl group include methoxycarbonyl, ethoxycarbonyl, n-propoxycarbonyl, isopropoxycarbonyl, n-butoxycarbonyl, sec-butoxycarbonyl and tert-butoxycarbonyl.

The $C_{7-11}$ aryloxycarbonyl group includes both of non-substituted aryloxycarbonyl group and substituted aryloxycarbonyl group, where the aryl groups possibly composing the aryloxycarbonyl group are same as those defined in the above, (the term "aryloxycarbonyl group" in this specification is used in this meaning unless otherwise specifically be noted), where the same will apply to any substituents in the aryl group portion and specific examples thereof. Specific examples of the aryloxycarbonyl group include phenoxycarbonyl and naphthoxycarbonyl.

The heteroaryloxycarbonyl group includes both of non-substituted heteroaryloxycarbonyl group and substituted heteroaryloxycarbonyl group, where the heteroaryl groups possibly composing the heteroaryloxycarbonyl group are same as those defined in the above (the term "heteroaryloxycarbonyl group" in this specification is used in this meaning unless otherwise specifically be noted), where the same will apply to any substituents in the heteroaryl group portion and specific examples thereof. Specific examples of the heteroaryloxycarbonyl group include 4-pyridyloxycarbonyl.

The $C_{2-16}$ alkanoyl group includes both of non-substituted alkanoyl group and substituted alkanoyl group, where alkyl groups possibly composing the alkanoyl group are same as those defined in the above (the term "alkanoyl group" in this specification is used in this meaning unless otherwise specifically be noted), and the same will apply to any substituents in the alkyl group and specific examples thereof. Specific examples of the alkanoyl group include acetyl, propionyl, n-butanoyl and isobutanoyl.

The $C_{7-11}$ aroyl group includes both of non-substituted aroyl group and substituted aroyl group, where the aryl groups possibly composing the aroyl group are same as those defined in the above (the term "aroyl group" in this specification is used in this meaning unless otherwise specifically be noted), and the same will apply to any substituents in the aryl group portion and specific examples thereof. Specific examples of the aroyl group include 3-chlorobenzoyl.

The heteroaroyl group includes both of non-substituted heteroaroyl group and substituted heteroaroyl group, where heteroaryl groups possibly composing the heteroaroyl group are same as those defined in the above (the term "heteroaroyl group" in this specification is used in this meaning unless otherwise specifically be noted), and the same will apply to any substituents in the heteroaryl group portion and specific examples thereof. Specific examples of the heteroaroyl group include 2-thiophenecarbonyl.

The $C_{2-16}$ alkylcarbonyloxy group includes both of non-substituted alkylcarbonyloxy group and substituted alkylcarbonyloxy group, where alkyl groups possibly composing the alkylcarbonyloxy group are same as those defined in the above (the term "alkylcarbonyloxy group" in this specification is used in this meaning unless otherwise specifically be noted), and the same will apply to any substituents in the alkyl group portion and specific examples thereof. Specific examples of the alkylcarbonyloxy group include acetoxy.

The $C_{7-11}$ arylcarbonyloxy group includes both of non-substituted arylcarbonyloxy group and substituted arylcarbonyloxy group, where aryl groups possibly composing the arylcarbonyloxy group are same as those defined in the above (the term "arylcarbonyloxy group" in this specification is used in this meaning unless otherwise specifically be noted), and the same will apply to any substituents in the aryl group portion and specific examples thereof. Specific examples of the arylcarbonyloxy group include benzoyloxy.

The heteroarylcarbonyloxy group includes both of non-substituted heteroarylcarbonyloxy group and substituted heteroarylcarbonyloxy group, where heteroaryl groups possibly composing the heteroarylcarbonyloxy group are same as those defined in the above (the term "heteroarylcarbonyloxy group" in this specification is used in this meaning unless otherwise specifically be noted), and the same will apply to any substituents in the heteroaryl group portion and specific examples thereof. Specific examples of the heteroarylcarbonyloxy group include 3-pyridinecarbonyloxy.

The $C_{1-15}$ alkylthio group includes both of non-substituted alkylthio group and substituted alkylthio group, where alkyl groups possibly composing the alkylthio group are same as those defined in the above (the term "alkylthio group" in this specification is used in this meaning unless otherwise specifically be noted), and the same will apply to any substituents in the alkyl group portion and specific examples thereof. Specific examples of the alkylthio group include straight-chained or branched ones, which include methylthio, ethylthio, n-pryopylthio, isopropylthio, n-butylthio, sec-butylthio and tert-butylthio.

The $C_{6-10}$ arylthio group includes both of non-substituted arylthio group and substituted arylthio group, where aryl groups possibly composing the arylthio group are same as those defined in the above (the term "arylthio group" in this specification is used in this meaning unless otherwise specifically be noted), and the same will apply to any substituents in the aryl group portion and specific examples thereof. The specific examples of the arylthio group include phenylthio and tolylthio.

The heteroarylthio group includes both of non-substituted heteroarylthio group and substituted heteroarylthio group, where heteroarylthio groups possibly composing the heteroaryl group are same as those defined in the above (the term "heteroarylthio group" in this specification is used in this meaning unless otherwise specifically be noted), and the same will apply to any substituents in the heteroaryl group portion and specific examples thereof. Specific examples of the heteroarylthio group include pyridylthio, imidazolydylthio and thienylthio.

The $C_{1-15}$ alkylsulfonyl group includes both of non-substituted alkylsulfonyl group and substituted alkylsulfonyl group, where alkyl groups possibly composing the alkylsulfonyl group are same as those defined in the above (the term "alkylsulfonyl group" in this specification is used in this meaning unless otherwise specifically be noted), and the same will apply to any substituents in the alkyl group portion and specific examples thereof. Specific examples of the alkylsulfonyl group include straight-chained or branched ones, which include methanesulfonyl, ethanesulfonyl, n-propylsulfonyl, isopropylsulfonyl, n-butylsulfonyl, sec-butylsulfonyl and tert-butylsulfonyl.

The $C_{6-10}$ arylsulfonyl group includes both of non-substituted arylsulfonyl group and substituted arylsulfonyl group, where aryl groups possibly composing the arylsulfonyl group are same as those defined in the above (the term "arylsulfonyl group" in this specification is used in this meaning unless otherwise specifically be noted), and the same will apply to any substituents in the aryl group portion and specific examples thereof. Specific examples of the arylsulfonyl group include benzenesulfonyl, fluorobenzenesulfonyl and tosyl.

The heteroarylsulfonyl group includes both of non-substituted heteroarylsulfonyl group and substituted heteroarylsulfonyl group, where heteroaryl groups possibly composing the heteroarylsulfonyl group are same as those defined in the above (the term "heteroarylsulfonyl group" in this specification is used in this meaning unless otherwise specifically be noted), and the same will apply to any substituents in the heteroaryl group portion and specific examples thereof. Specific examples of the heteroarylsulfonyl group include 2-pyridylsulfonyl and 2-thienylsulfonyl.

The $C_{1-15}$ alkylsulfinyl group includes both of non-substituted alkylsulfinyl group and substituted alkylsulfinyl group, where alkyl groups possibly composing the alkylsulfinyl group are same as those defined in the above (the term "alkylsulfinyl group" in this specification is used in this meaning unless otherwise specifically be noted), and the same will apply to any substituents in the alkyl group portion and specific examples thereof. Specific examples of the alkylsulfinyl group include straight-chained or branched ones, which include methanesulfinyl, ethanesulfinyl, n-propylsulfinyl, isopropylsulfinyl, n-butylsulfinyl, sec-butylsulfinyl and tert-burylsulfinyl.

The $C_{6-10}$ arylsulfinyl group includes both of non-substituted arylsulfinyl group and substituted arylsulfinyl group, where aryl groups possibly composing the arylsulfinyl group are same as those defined in the above (the term "arylsulfinyl group" in this specification is used in this meaning unless otherwise specifically be noted), and the same will apply to any substituents in the aryl group portion and specific examples thereof. Specific examples of the arylsulfinyl group include benzenesulfinyl.

The heteroarylsulfinyl group includes both of non-substituted heteroarylsulfinyl group and substituted heteroarylsulfinyl group, where heteroaryl groups possibly composing the heteroarylsulfinyl group are same as those defined in the above (the term "heteroarylsulfinyl group" in this specification is used in this meaning unless otherwise specifically be noted), and the same will apply to any substituents in the heteroaryl group portion and specific examples thereof. Specific examples of the heteroarylsulfinyl group include 2-pyridylsulfinyl and 2-thienylsulfinyl.

$R^1$, $R^2$ and $R^3$ in the groups represented by —$NR^1R^2$, —$NR^1COR^2$, —$NR^1SO_2R^2$, —$NR^1CONR^2R^3$ and —$CONR^1R^2$, independently represent a hydrogen atom, $C_{1-15}$ alkyl group, $C_{2-15}$ alkenyl group, $C_{6-10}$ aryl group, $C_{1-15}$ alkoxy group, $C_{6-10}$ aryloxy group, heteroaryloxy group or heteroaryl group.

The $C_{2-15}$ alkenyl group includes both of non-substituted alkenyl group and substituted alkenyl group, where alkenyl chain may be straight or branched, and may be a cycloalkenyl group having one or more cyclic structures (the term "alkenyl group" in this specification is used in this meaning unless otherwise specifically be noted). For the case where the alkenyl group has any substituent, the substituent can typically be exemplified by a halogen atom, nitro, cyano, hydroxy, carboxy, $C_{6-10}$ aryl group, heteroaryl group, —OR, —SR, —SOR, —$SO_2R$ and —NRR'. R and R' herein are same as those defined in the above. Specific examples of the alkenyl group include vinyl group, 1-propenyl group, 2-propenyl group, 2-methyl-1-propenyl group and 1,2-dimethylpropenyl group. On the other hand, for the case where the alkenyl group is arylalkenyl group having an aryl group as a substituent, the aryl groups possibly composing the arylalkenyl group are same as those descried in the above, and the same will apply to any substituents in the aryl group portion and specific examples thereof. Specific examples thereof include 2-phenylvinyl group. For the case where the alkenyl group is a heteroarylalkenyl group having a heteroaryl group as a substituent, the heteroaryl groups possibly composing the heteroarylalkenyl group are same as those defined in the above, and the same will apply to any substituents in the heteroaryl group portion and specific examples thereof.

It is to be noted that the $C_{1-15}$ alkyl group, $C_{1-15}$ alkoxy group, $C_{6-10}$ aryl group, $C_{6-10}$ aryloxy group, heteroaryloxy group and heteroaryl group respectively represented by $R^1$, $R^2$ and $R^3$ are same as those defined in the above, and same will apply to specific examples thereof.

Either $R^1$ and $R^2$ or $R^2$ and $R^3$ may bind with each other to respectively form a ring; which ring may additionally contain at least one ring-composing atom selected from oxygen atom, nitrogen atom and sulfur atom; which ring may contain a double bond; and which ring may have a substituent. The ring possibly formed includes lactam, pyrrolidine, piperidine, morpholine and hydantoin. For the case the ring possibly formed include any substituent, such substituent can be exemplified by those represented by the foregoing A, B and C.

Any two of A, B and C bound on the adjacent carbon atoms may form a benzene ring or methylenedioxy ring.

In the formula (1), X and X' independently represent a hydrogen atom, halogen atom, nitro, cyano, hydroxy, carboxy, $C_{1-15}$ alkyl group, $C_{2-15}$ alkenyl group, $C_{2-15}$ alkynyl group, $C_{6-10}$ aryl group, heteroaryl group, $C_{1-15}$ alkoxy group, $C_{6-10}$ aryloxy group, heteroaryloxy group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, —$NR^4R^5$, —$NR^4COR^5$, —$NR^4SO_2R^5$, —$NR^4CONR^5R^6$, —$OCONR^4R^5$ and —$CONR^4R^5$.

The halogen atom, alkyl group, alkenyl group, aryl group, heteroaryl group, alkoxy group, aryloxy group, heteroaryloxy group, alkanoyl group, aroyl group, heteroaroyl group, alkylcarbonyloxy group, arylcarbonyloxy group, heteroarylcarbonyloxy group, alkylthio group, arylthio group and heteroarylthio group independently represented by X and X' are same as those defined in the above, and the same will apply to specific examples thereof.

$C_{2-15}$ alkynyl group independently represented by X and X' include both of non-substituted alkynyl group and substituted alkynyl group, where the alkynyl group may be straight-chained or branched (the term "alkynyl group" in this specification is used in this meaning unless otherwise specifically be noted). For the case where the alkynyl group has any substituent, such substituent can typically be exemplified by halogen atom, nitro, cyano, hydroxy, carboxy, $C_{6-10}$ aryl group, heteroaryl group, —OR, —SR, —SOR, —$SO_2R$ and —NRR'. R and R' are same as those defined in the above. Specific examples of the alkynyl group include hexynyl group, phenylethynyl and pyridylethynyl. For the case where the alkynyl group is an arylalkynyl group having an aryl group as a substituent, the aryl groups possibly composing the arylalkynyl group are same as those defined in the above, and the same will apply to any substituents in the aryl group portion and specific examples thereof. Specific examples thereof include 2-phenylethynyl. On the other hand, for the case where the alkynyl group is heteroarylalkynyl group having a heteroaryl group as a substituent, the heteroaryl groups possibly composing the heteroarylalkynyl group are same as those defined in the above, and the same will apply to any substituents in the heteroaryl group portion and specific examples thereof.

$R^4$, $R^5$ and $R^6$ in the foregoing —$NR^4R^5$, —$NR^4COR^5$, —$NR^4SO_2R^5$, —$NR^4CONR^5R^6$, —$OCONR^4R^5$ and —$CONR^4R^5$ independently represent a hydrogen atom, $C_{1-15}$ alkyl group, $C_{2-15}$ alkenyl group, $C_{6-10}$ aryl group, $C_{1-15}$ alkoxy group, $C_{6-10}$ aryloxy group, heteroaryloxy group or heteroaryl group. Either $R^4$ and $R^5$ or $R^5$ and $R^6$ may respectively form a ring; which ring may additionally contain at least one ring-composing atom selected from oxygen atom, nitrogen atom and sulfur atom; which ring may contain a double bond; and which ring may have a substituent. The alkyl group, alkenyl group, aryl group, alkoxy group, aryloxy group, heteroaryloxy group, and heteroaryl group independently represented by $R^4$, $R^5$ and $R^6$ are the same as those defined in the above, and the same will apply also to the specific the specific examples. Rings possibly formed by binding either $R^4$ and $R^5$ or $R^5$ and $R^6$ are same as those formed by binding either $R^1$ and $R^2$ or $R^2$ and $R^3$, respectively. The same will apply also to the substituents if any.

Compounds represented by the formula (1) include those in which at least one of X and X' is represented by the formulae (2) to (5) below:

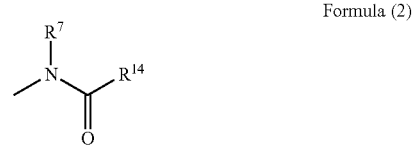

Formula (2)

Formula (3)

Formula (4)

Formula (5)

Where $R^7$ represents a hydrogen atom or $C_{1-15}$ alkyl group, and $R^{14}$ represents either of the groups represented by the formulae (6) and (7) below:

Formula (6)

Formula (7)

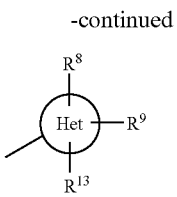

In the formulae (6) and (7), $R^8$ and $R^9$ independently represent a hydrogen atom, halogen atom, nitro, cyano, hydroxy, carboxy, $C_{1-15}$ alkyl group, $C_{6-10}$ aryl group, $C_{1-15}$ alkoxy group, $C_{6-10}$ aryloxy group, heteroaryloxy group, $C_{2-16}$ alkoxycarbonyl group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, $C_{1-15}$ alkylsulfonyl group, $C_{6-10}$ arylsulfonyl group, heteroarylsulfonyl group, $C_{1-15}$ alkylsulfinyl group, $C_{6-10}$ arylsulfinyl group, heteroarylsulfinyl group, $—NR^{10}R^{11}$, $—NR^{10}COR^{11}$, $—NR^{10}SO_2R^{11}$, $—NR^{10}CONR^{11}R^{12}$ or $—CONR^{10}R^{11}$. "Het" in the formula represents an aromatic heterocycle containing at least one hetero atom selected from nitrogen atom, oxygen atom and sulfur atom, and $R^{13}$ represents a hydrogen atom or $C_{1-15}$ alkyl group.

The alkyl groups represented by $R^7$, $R^8$, $R^9$ and $R^{13}$ are same as those defined in the above, and the same will apply also to the specific examples thereof. The halogen atom, aryl group, alkoxy group, aryloxy group, heteroaryloxy group, alkoxycarbonyl group, alkanoyl group, aroyl group, heteroaroyl group, alkylcarbonyloxy group, arylcarbonyloxy group, heteroarylcarbonyloxy group, alkylthio group, arylthio group, heteroarylthio group, alkylsulfonyl group, arylsulfonyl group, heteroarylsulfonyl group, alkylsulfinyl group, arylsulfinyl group and heteroarylsulfinyl group respectively represented by $R^8$ and $R^9$ are same as those defined in the above, and the same will apply also to the specific examples thereof.

$R^{10}$, $R^{11}$ and $R^{12}$ in $—NR^{10}R^{11}$, $—NR^{10}COR^{11}$, $—NR^{10}SO_2R^{11}$, $—NR^{10}CONR^{11}R^{12}$ and $—CONR^{10}R^{11}$ independently express a hydrogen atom, $C_{1-15}$ alkyl group, $C_{2-15}$ alkenyl group, $C_{1-15}$ alkoxy group, $C_{6-10}$ aryl group, $C_{6-10}$ aryloxy group, heteroaryloxy group or heteroaryl group. Either $R^{10}$ and $R^{11}$ or $R^{11}$ and $R^{12}$ may bind with each other to respectively form a ring; which ring may additionally contain at least one ring-composing atom selected from oxygen atom, nitrogen atom and sulfur atom; which ring may contain a double bond; and which ring may have a substituent. The alkyl group, alkenyl group, aryl group, alkoxy group, aryloxy group, heteroaryloxy group and heteroaryl group independently represented by $R^{10}$, $R^{11}$ and $R^{12}$ are same as those defined in the above, and the same will apply to the specific examples thereof. Rings possibly formed by binding either $R^{10}$ and $R^{11}$ or $R^{11}$ and $R^{12}$ are same as those formed by binding either $R^1$ and $R^2$ or $R^2$ and $R^3$, respectively. The same will apply also to the substituents if any.

The aromatic heterocycle represented by Het is such that containing at least one hetero atom selected from nitrogen atom, oxygen atom and sulfur atom. The aromatic heterocycle includes both of non-substituted aromatic heterocycle and substituted aromatic heterocycle, and may have a condensed structure comprising two or more rings (the term "aromatic heterocycle" in this specification is used in this meaning, unless otherwise specifically be noted). Specific examples thereof include furan, thiophene, pyrrole, oxazole, thiazole, imidazole, triazole, tetrazole, pyridine, pyrimidine, indole, benzofuran, thianaphthene and purine.

Of the compounds represented by the formula (1), preferable compounds are 2,3-diphenylpropionic acid derivatives or salts thereof in which at least one of A, B and C represents $—NR^1R^2$, $—NR^1COR^2$, $—NR^1SO_2R^2$ or $—NR^1CONR^2R^3$, and at least one of X and X' represents a group or atom other than hydrogen atom; 2,3-diphenylpropionic acid derivatives or salts thereof in which at least one of A, B and C represents a $C_{1-15}$ alkyl group, $C_{1-15}$ alkoxy group, $C_{6-10}$ aryl group, heteroaryl group or $C_{2-16}$ alkoxycarbonyl group, and at least one of X and X' represents a group or atom other than hydrogen atom; or 2,3-diphenylpropionic acid derivatives or salts thereof in which at least one of A, B and C represents halogen atom, cyano or $C_{1-15}$ alkylthio group, and at least one of X and X' represents a group or atom other than hydrogen atom.

Of the compounds represented by the foregoing the formula (1), more preferable examples relate to 2,3-diphenylpropionic acid derivatives or salts thereof in which "A" represents $—NR^1COR^2$ substituted at the 3-position, X represents a group or atom other than hydrogen atom, X' represents a hydrogen atom; and more preferable examples relate to 2,3-diphenylpropionic acid derivatives or salts thereof in which "A" represents $—NR^1COR^2$ substituted at the 3-position, B represents a $C_{1-15}$ alkyl group or $C_{1-15}$ alkoxy group substituted at the 4- or 5-position, X' represents a hydrogen atom, and X represents a halogen atom, nitro, cyano, hydroxy, $C_{6-10}$ aryl group, heteroaryl group, $C_{1-15}$ alkoxy group, $—NR^4R^5$, $—NR^4COR^5$, $—NR^4SO_2R^5$, $—NR^4CONR^5R^6$, $—OCONR^4R^5$ or $—CONR^4R^5$ For the case where the compound represented by the formula (1) has a chiral carbon atom, the present invention also includes any racemic body, diastereomer and the individual optically active substances, and for the case where the compound can have geometrical isomers, the present invention also includes any of (E) body, (Z) body and a mixture thereof.

The compound of the present invention represented by the formula (1) includes any pharmacologically acceptable salts. Such salts are not specifically limited so far as they are pharmacologically acceptable, and examples of which include salts formed with inorganic base, organic base, organic acid, inorganic acid and amino acid. Examples of the salts with inorganic base include alkali metal salts such as sodium salt, potassium salt and calcium salt, and ammonium salt. Examples of the salts with organic base include triethylamine salt, pyridine salt, ethanolamine salt, cyclohexylamine salt, and dicyclohexylamine salt. Examples of the salts with organic acid include formate, acetate, tartrate, maleate, succinate and methanesulfonate. Examples of the salts with inorganic acid include hydrochloride, hydrobromide and nitrate. Examples of the salts with amino acid include glycine salt, alanine salt, arginine salt, glutamate and aspartate.

The compound represented by the formula (1) can be prepared according to the preparation methods A to L described below.

[Preparation Method A]

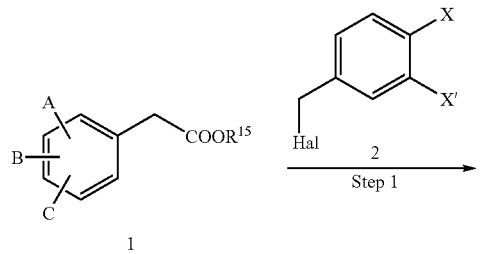

A, B, C, X and X' in the formulae are same as those defined in the formula (1) in the above, and $R^{15}$ represents a $C_{1-10}$ alkyl group or aryl group, and Hal represents a halogen atom.

(Step 1)

In a proper neutral solvent (e.g., tetrahydrofuran), a phenylacetic acid derivative represented by the formula 1 is reacted at a low temperature with a base such as lithium diisopropylamide to thereby generate enolate anion, and is further reacted with a benzyl halide represented by the formula 2, which results in production of a correspondent compound represented by the formula 3.

(Step 2)

The obtained ester derivative represented by the formula 3 is hydrolyzed under an alkaline condition using an alkaline aqueous solution such that containing lithium hydroxide, sodium hydroxide or potassium hydroxide to thereby obtain a compound represented by the formula 4. The reaction solvent used herein is not specifically limited so far as it is miscible with water, where preferable examples thereof include methanol, ethanol, tetrahydrofuran, 1,4-dioxane and 1,2-dimethoxyethane. Reaction temperature is not specifically limited, where the general practice employs 0 to 100° C., and a reaction time ranging from 30 minutes to 6 hours. When $R^{15}$ is an aryl group, $R^{15}$ can be deprotected using a palladium catalyst. When $R^{15}$ is tert-butyl, $R^{15}$ can be deprotected using a strong acid such as hydrochloric acid or trifluoroacetic acid. And when $R^{15}$ is benzyl, $R^{15}$ can reductively be deprotected using a palladium catalyst.

A compound represented by the formula (1) having X representing $—NR^4R^5$, $—NR^4COR^5$, $—NR^4SO_2R^5$ or $—NR^4CONR^5R^6$ (where, $R^6$ represents a hydrogen atom) can be synthesized according to preparation method B below.

[Preparation Method B]

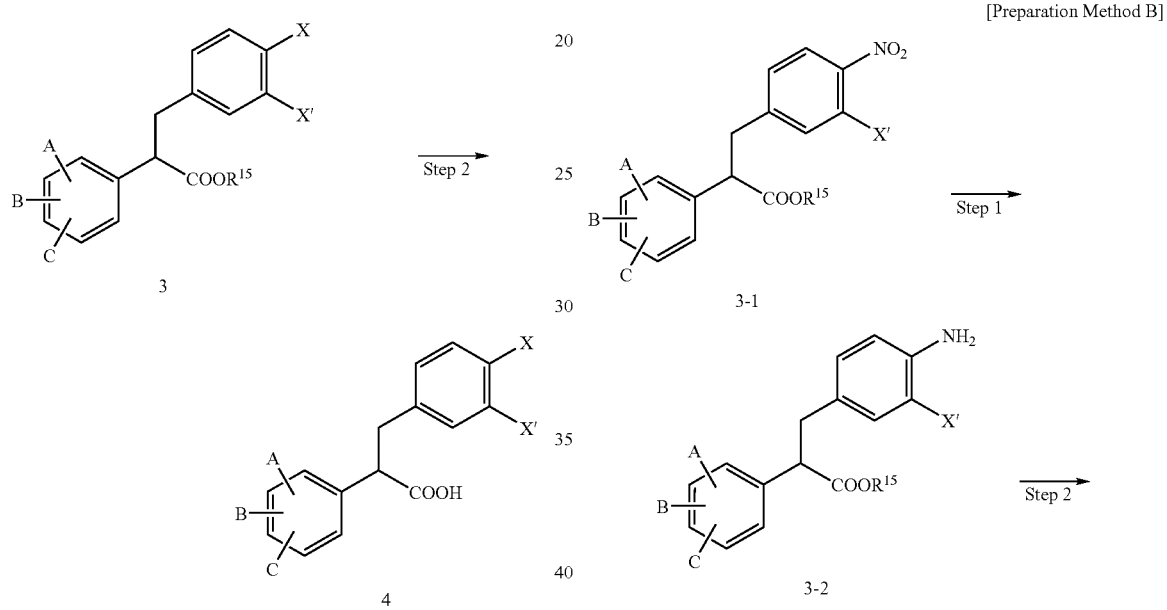

-continued

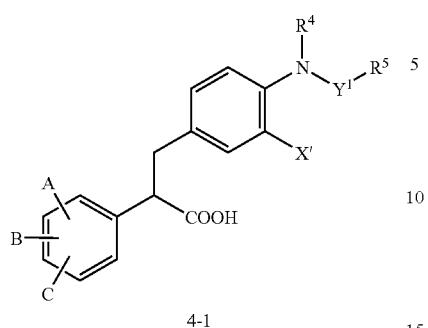

4-1

A, B, C, X', $R^4$, $R^5$, $R^{15}$ and Hal in the formulae are same as those defined in the above. $Y^1$ represents a single bond, —CO—, —SO$_2$— or —CONH—.

(Step 1)

A compound represented by the formula 3 in which X is a nitro (a compound represented by the formula 3-1) is obtained by step 1 of preparation method A in the above, and the obtained compound is then reduced by contact hydrogenation under the presence of a catalyst such as palladium/carbon or platinum oxide, to thereby obtain a compound represented by the formula 3-2 in which the nitro is reduced to an amino. The reaction solvent used herein is not specifically limited so far as it does not distinctively inhibit the reaction, where examples of which include methanol, ethanol, ethyl acetate, tetrahydrofuran, dimethylformamide and any arbitrary mixtures thereof. While the hydrogen pressure is not specifically limited, general practice employs a pressure of 1 to 5 kg/cm$^2$. The reduction is also available with a metal reagent such as tin chloride (I) or zinc.

(Step 2)

Monoalkylation of the amino in a compound represented by the formula 3-3 can be converted into a compound represented by the formula 3-2. For example, the reaction of a compound represented by the formula 3-2 with a reducing agent such as sodium cyanotrihydroborate or sodium triacetoxyborohydride is carried out in methanol under an aldehyde or ketone. This step is omissible when $R^4$ represents a hydrogen atom.

(Step 3)

A compound represented by the formula 3-4 is obtained by reacting a primary amine represented by the formula 3-2 or a secondary amine represented by the formula 3-3 with an alkyl halide, acid chloride or sulfonyl chloride represented by formula $R^5Y^1$-Hal, or with isocyanic acid represented by formula $R^5N$=C=O. As an exemplary reaction with an alkyl halide, reaction in dimethylformamide with methallyl bromide in the presence of base such as sodium hydride can yield a tertiary amine. Reaction in dichloromethane with an acid chloride or sulfonyl chloride in the presence of a base such as pyridine can yield corresponding amide and sulfonamide, respectively. Reaction with isocyanic acid will successfully yield a corresponding urea using a reaction solvent such as ethyl acetate which does not distinctively inhibit the reaction.

(Step 4)

compound represented by the formula 4-1 can be prepared by hydrolyzing an ester derivative represented by the formula 3-4 typically under the conditions described in Step 2 in preparation method "A".

A compound represented by the formula (1) in which "A" represents any of —NR$^1$R$^2$, —NR$^1$COR$^2$, —NR$^1$SO$_2$R$^2$ and —NR$^1$CONR$^2$R$^3$ (where, R$^3$ represents a hydrogen atom) substituted at the 3-position of the benzene ring, and X represents any of —NR$^4$R$^5$, —NR$^4$COR$^5$, —NR$^4$SO$_2$R$^5$ and —NR$^4$CONR$^5$R$^6$ (where, R$^6$ represents a hydrogen atom) can be prepared by preparation method C below.

[Preparation Method C]

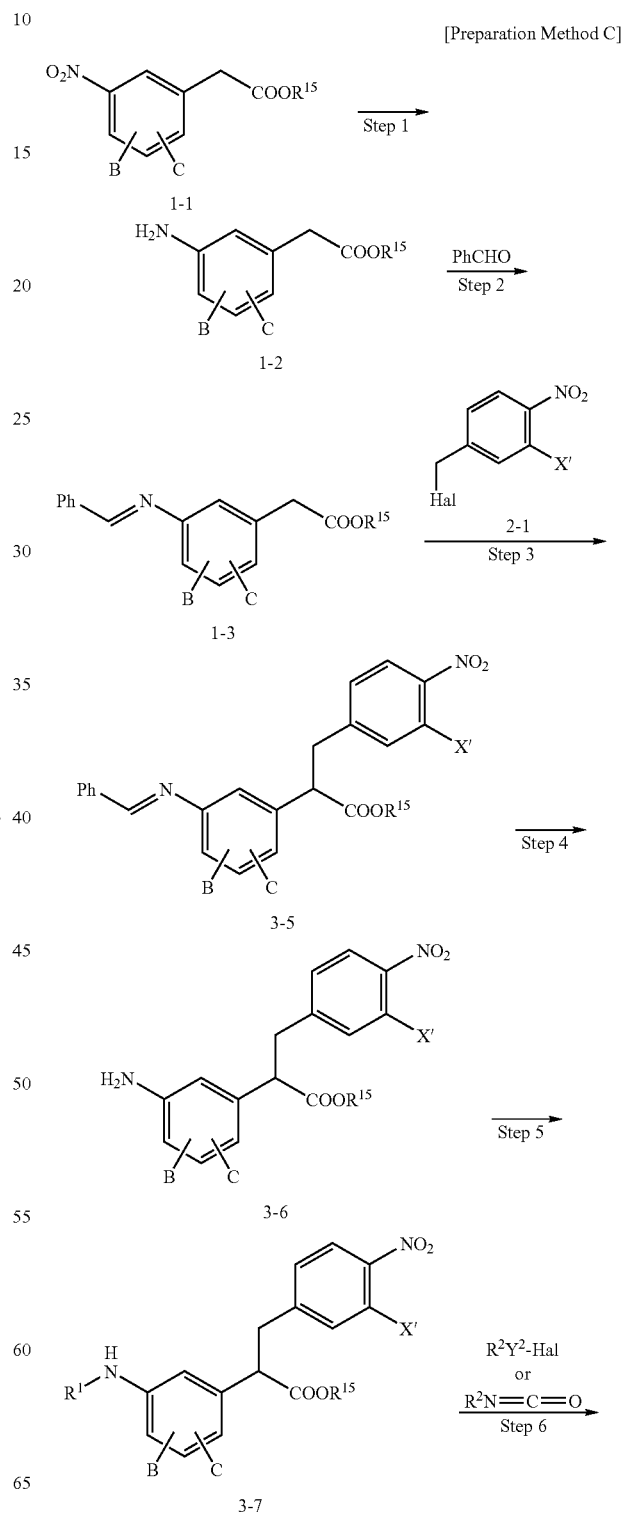

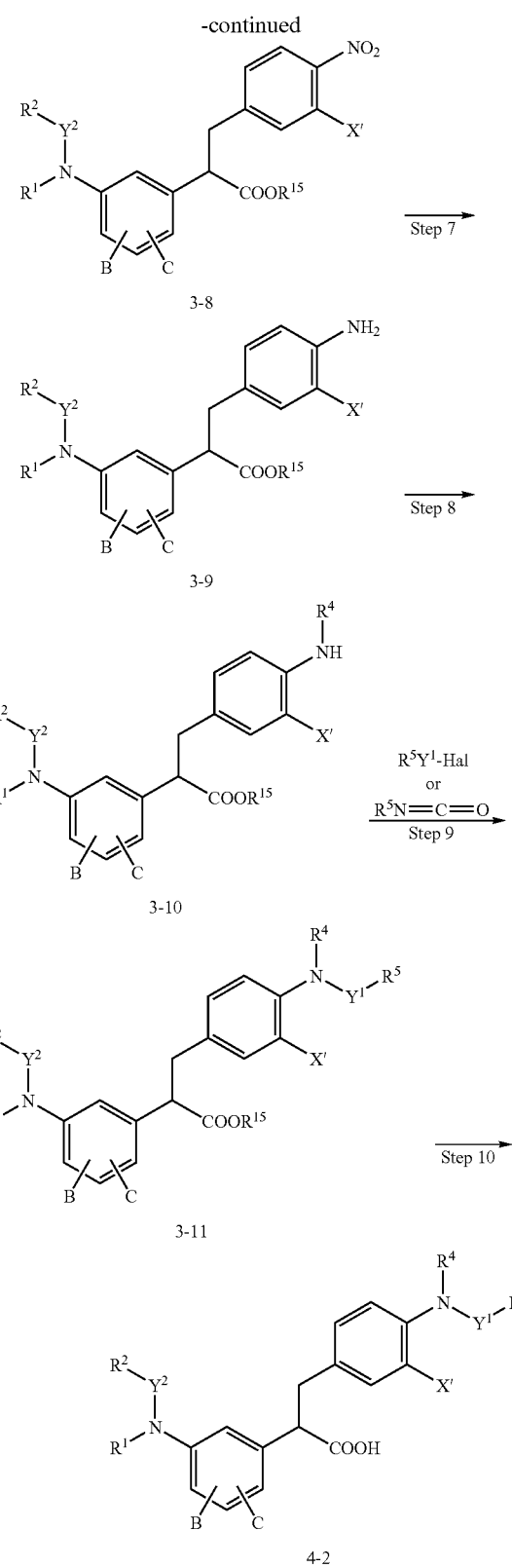

3-8

3-9

3-10

3-11

4-2

B, C, X', R¹, R², R⁴, R⁵, R¹⁵, Hal and Y¹ in the formulae are same as those defined in the above, Ph represents a phenyl, and Y² represents a single bond, —CO—, —SO₂— or —CONH—.

(Step 1)

A compound represented by the formula 1-2 can be prepared by reducing an ester derivative of 3-nitrophenyl acetate represented by the formula 1-1 as described in step 1 of preparation method B.

(Step 2)

A compound having an amino protected by a benzylidene as represented by the formula 1-3 can be prepared by heating and dehydrating an ester derivative of 3-aminophenyl acetate represented by the formula 1-2 typically in the presence of benzaldehyde. The reaction solvent used herein is not specifically limited so far as it does not distinctively inhibit the reaction, where preferable examples thereof include benzene, toluene and chlorobenzene.

(Step 3)

In a proper neutral solvent (e.g., tetrahydrofuran), a benzylidene aminophenyl acetate derivative represented by the formula 1-3 is reacted at a low temperature with a base such as lithium diisopropylamide to thereby generate enolate anion, and is further reacted with a benzyl halide represented by the formula 2-1, which results in production of a correspondent compound represented by the formula 3-5.

(Step 4)

A compound represented by the formula 3-6 can be prepared by adding hydrochloric acid in a solvent such as tetrahydrofuran under an acidic condition, to thereby eliminate a benzylidene protective group protecting the amino in the compound.

(Step 5)

A compound represented by the formula 3-7 can be prepared by subjecting the amino in a compound represented by the formula 3-6 to monoalkylation as described in step 2 of preparation method 2. The step is omissible when $R^1$ represents a hydrogen atom.

(Step 6)

Reaction of a secondary amine represented by the formula 3-7 with alkyl halide, acid chloride, sulfonyl chloride or isocyanate according to the method described in step 3 of preparation method B will yield corresponding tertiary amine, amide, sulfonamide or urea represented by the formula 3-8.

(Step 7 to 10)

These steps are same as those described in steps 1 to 4 of preparation method B.

On the other hand, it is also allowable in preparation method C to protect the amino of a compound represented by the formula 3-6 with a protective group such as tert-butoxycarbonyl, to thereby modify the nitro in advance. In this case, the compound represented by the formula (1) can be prepared according to preparation method D below.

[Preparation Method D]

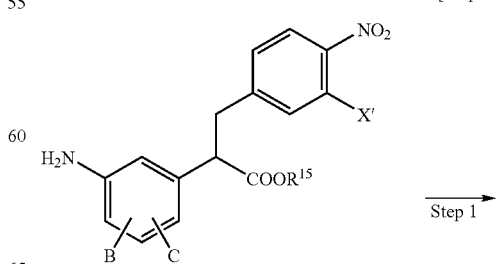

3-6

-continued

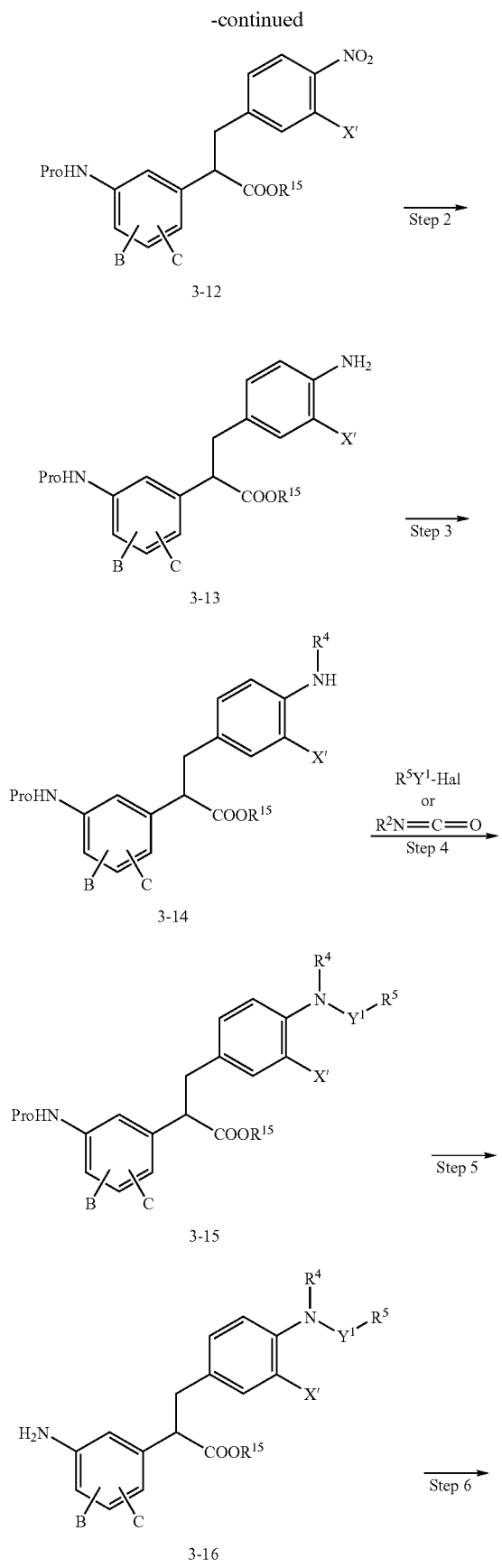

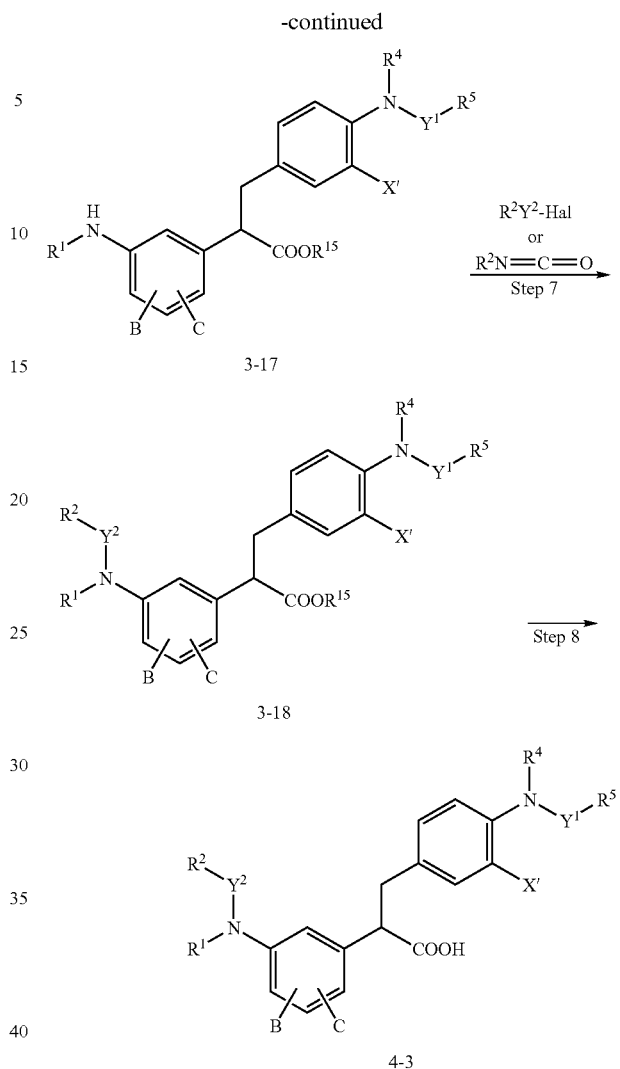

B, C, X', $R^1$, $R^2$, $R^4$, $R^5$, $R^{15}$, Hal, $Y^1$ nd $Y^2$ in the formulae are same as those defined in the above. Pro represents a protective group.

(Step 1)

The amino of a compound represented by the formula 3-6 is protected with a protective group Pro (e.g., tert-butoxycarbonyl) according to a method well known in the art, typically by reacting with di-tert-butyl bicarbonate in a proper neutral solvent (e.g., chloroform), which yields a compound represented by the formula 3-12.

(Steps 2 to 4)

These steps are same as those described for steps 1 to 3 of preparation method B.

(Step 5)

A compound represented by the formula 3-16 can be prepared by eliminating a protective group (e.g., tert-butoxycarbonyl) in a compound represented by the formula 3-15 under an acidic condition, which is typified by reacting with a hydrochloric acid-ethyl acetate mixed solution.

(Step 6 to 7)

These steps are same as those described for steps 5 to 6 of preparation method C in the above.

(Step 8)

This step is same as that described for step 10 of preparation method C in the above.

Any compound represented by the formula (1) in which X is an aryl group or heteroaryl group can be prepared according to preparation method E below:

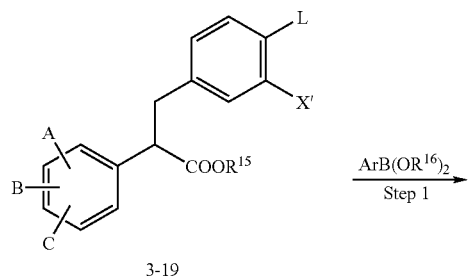

[Preparation Method E]

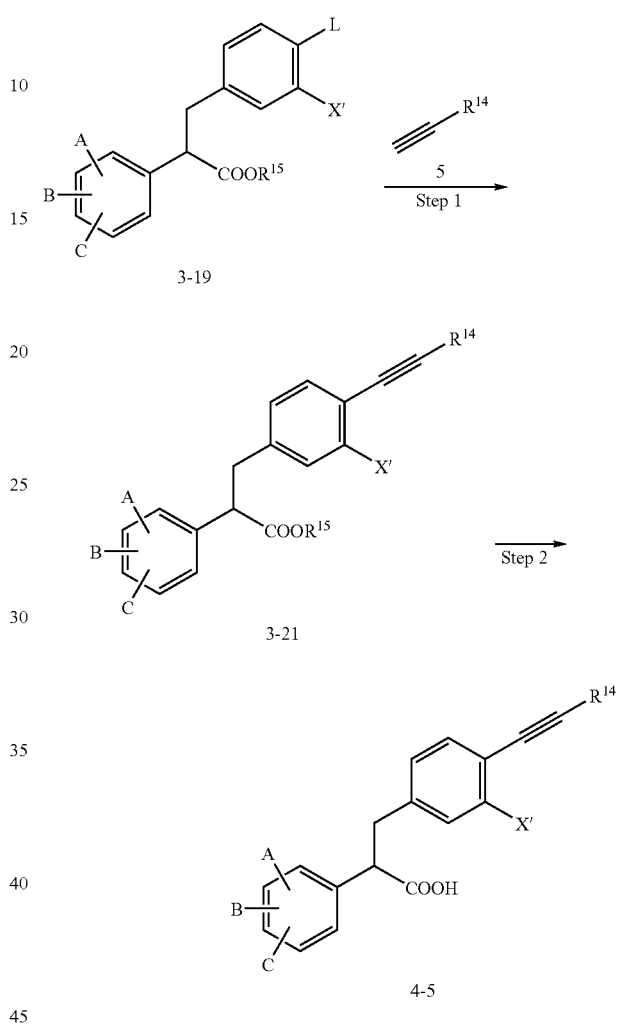

[Preparation Method F]

A, B, C, X' and $R^{15}$ in the formulae are same as those defined in the above. $R^{16}$ represents a hydrogen atom or alkyl group, Ar represents an aryl group or heteroaryl group, and L represents an eliminative group (e.g., bromine atom or iodine atom).

(Step 1)

Reaction of a compound represented by the formula 3-19 with aryl borate or heteroarylborate in the presence of a catalyst such as potassium carbonate and tetrakis(triphenylphosphine) palladium will yield a compound represented by the formula 3-20. The reaction solvent used herein is not specifically limited so far as it does not distinctively inhibit the reaction, where examples of which include benzene, toluene, tetrahydrofuran, 1,2-dimethoxyethane, dimethylformamide, water, and any arbitrary mixtures thereof.

(Step 2)

A compound represented by the formula 4-4 can be prepared by hydrolyzing an ester derivative represented by the formula 3-20 under the alkaline condition described in step 2 of preparation method "A" in the above.

A, B, C, X', L, $R^{14}$ and $R^{15}$ in the formulae are same as those defined in the above.

(Step 1)

A compound represented by the formula 3-21 can be prepared by reacting a compound represented by the formula 3-19 with a compound represented by the formula 5 in the presence of a catalyst such as base typified by triethylamine, or other catalyst such as copper iodide (I) or tetrakis(triphenylphosphine) palladium. The reaction solvent used herein is not specifically limited so far as it does not distinctively inhibit the reaction, where examples of which include benzene, toluene, dimethylformamide and any arbitrary mixtures thereof.

(Step 2)

A compound represented by the formula 4-5 can be prepared by hydrolyzing an ester derivative represented by the formula 3-21 under the condition described in step 2 of preparation method "A" in the above.

Any compound represented by the formula 1-1 in preparation method C and having B representing an alkoxy group can be prepared according to preparation method G below.

[Preparation Method G]

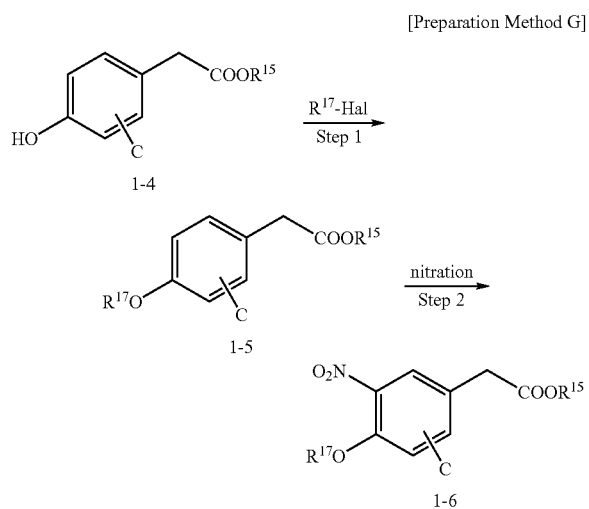

C, $R^{15}$ and Hal in the formulae are same as those defined in the above, and $R^{17}$ represents a $C_{1-15}$ alkyl group.

(Step 1)

Reaction of a compound represented by the formula 1-4 with an alkyl halide in the presence of a base such as potassium carbonate yields a compound represented by the formula 1-5. The reaction solvent used herein is not specifically limited so far as it does not distinctively inhibit the reaction, where examples of which include acetone, dimethylformamide, dimethyl sulfoxide and any arbitrary mixtures thereof.

(Step 2)

A compound represented by the formula 1-6 can be prepared by drop-wisely adding a nitric acid to a compound represented by the formula 1-5 in the presence of a catalytic amount of concentrated sulfuric acid. The reaction solvent used herein is not specifically limited so far as it does not distinctively inhibit the reaction, where examples of which include acetic acid, acetic anhydride, water, and any arbitrary mixtures thereof.

In particular, any compound represented by the formula 1-6 in preparation method G, in which $R^{17}$ is a primary alkyl group, can be prepared according to preparation method H below.

[Preparation Method H]

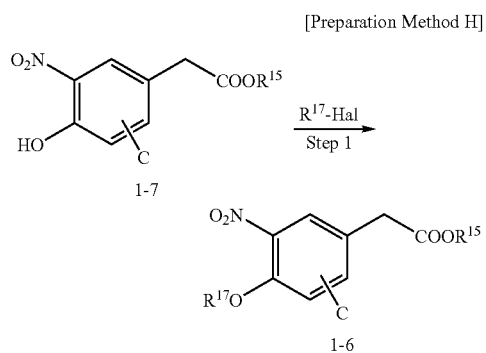

C, $R^{15}$, Hal and $R^{17}$ in the formulae are same as those defined in the above.

(Step 1)

A compound represented by the formula 1-6 can be prepared by alkylation of a phenolic hydroxy of a compound represented by the formula 1-7 according to step 1 of preparation method G in the above.

Any compound represented by the formula 1-1 in preparation method C, in which B is an aryl group substituting the 4-position of the benzene ring, can be prepared according to preparation method I below.

[Preparation Method I]

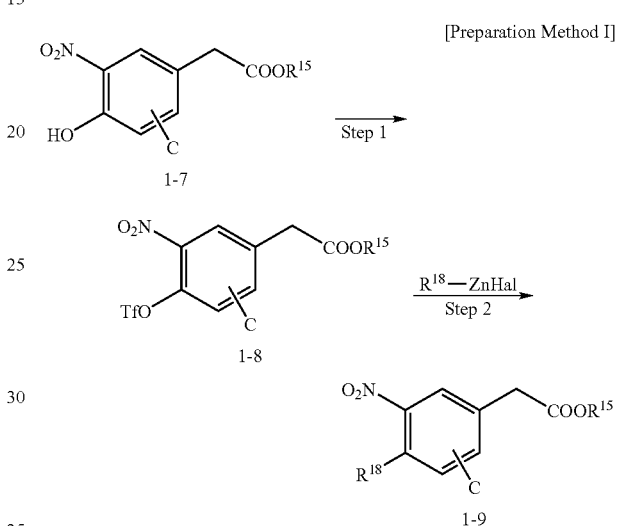

C, $R^{15}$ and Hal in the formulae are same as those described in the above, $R^{18}$ is an alkyl group, and Tf is a trifluoromethanesulfonyl.

(Step 1)

A compound represented by the formula 1-8 can be prepared by the reaction of a compound represented by the formula 1-7 with trifluoromethanesulfonic acid anhydride in the presence of a base such as pyridine. The reaction solvent used herein is not specifically limited so far as it does not distinctively inhibit the reaction, where examples of which include dichloromethane, 1,2-dichloroethane, and any arbitrary mixtures thereof.

(Step 2)

A compound represented by the formula 1-9 can be prepared by the reaction of a compound represented by the formula 1-8 with an alkyl zinc compound in the presence of a palladium catalyst. The reaction solvent used herein is not specifically limited so far as it does not distinctively inhibit the reaction, where examples of which include tetrahydrofuran, diethyl ether, toluene, 1,2-dimethoxyethane, and any arbitrary mixtures thereof. (reference: *J. Org. Chem., Vol* 42, No. 10, 1977).

A compound represented by the formula 4-2 in preparation method C, having $Y^1$ and $Y^2$ representing carbonyls, and having $R^4$ representing a hydrogen atom can be prepared also by solid phase synthesis according to preparation method J below.

[Preparation Method J]

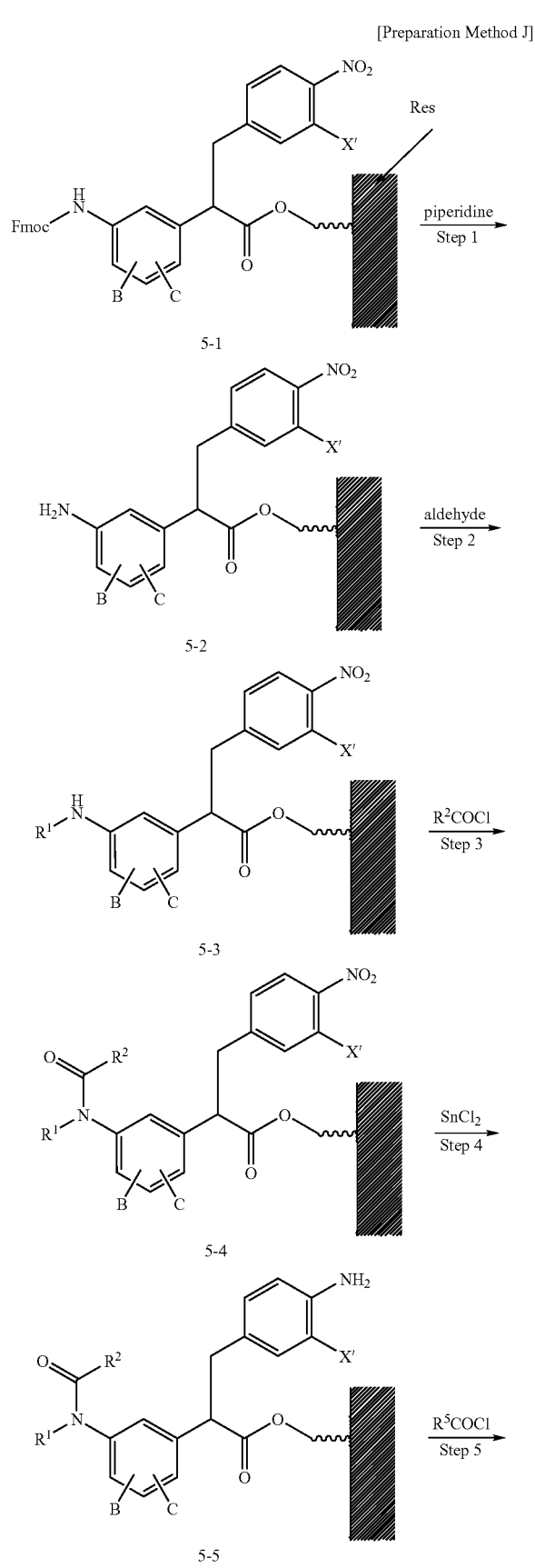

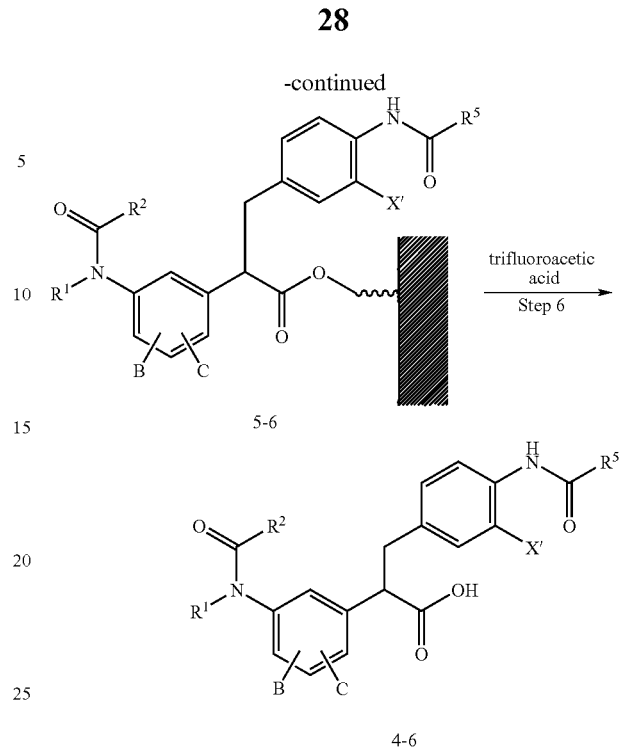

B, C, X', $R^1$, $R^2$ and $R^5$ in the formulae are same as those defined in the above, Fmoc represents 9-fluorenylmethoxycarbonyl, Res represents a solid phase resin, and a wavyline represents a linker. Linker available herein is mainly such that used for releasing the target compound from the solid phase using an acid such as trifluoroacetic acid, and types of which include Wang type, trityl type, and 4-(oxymethyl) benzamide ester type. A carboxylic acid synthesized by the foregoing preparation method C or D can chemically bind to the solid phase under various reaction conditions suitable for types of linker and support, and is converted into a compound represented by the formula 5-1.

(Step 1)

A compound represented by the formula 5-2 can be prepared by the reaction of a compound represented by the formula 5-1 with a base such as piperidine. The reaction solvent used herein is not specifically limited so far as it does not distinctively inhibit the reaction, where examples of which include dimethylformamide.

(Step 2)

A compound represented by the formula 5-3 can be prepared by subjecting the amino included in the compound represented by the formula 5-2 to monoalkylation reaction. For example, a compound represented by the formula 5-2 is reacted with a reducing agent such as sodium cyanotrihydroborate or sodium triacetoxyborohydride in the presence of an acidic catalyst such as acetic acid and in the presence of aldehyde. The reaction solvent used herein is not specifically limited so far as it does not distinctively inhibit the reaction, where examples of which include methanol, dimethylformamide, and any arbitrary mixtures thereof.

(Step 3)

A compound represented by the formula 5-4 can be prepared by the reaction of a compound represented by the formula 5-3 with an acid chloride in the presence of a base such as N-ethyl diisopropylamine. The reaction solvent used herein is not specifically limited so far as it does not distinctively inhibit the reaction, where examples of which include dichloromethane, dimethylformamide, pyridine, tetrahydrofuran, ethyl acetate, and any arbitrary mixtures thereof.

(Step 4)

A compound represented by the formula 5-5 can be prepared by reducing the nitro included in a compound represented by the formula 5-4 into an amino using tin chloride (I). The reaction solvent used herein is not specifically limited so far as it does not distinctively inhibit the reaction, where examples of which include dichloromethane, dimethylformamide, ethanol, and any arbitrary mixtures thereof.

(Step 5)

An amide represented by the formula 5-5 can be obtained by the reaction of a compound represented by the formula 5-5 with an acid chloride according to the method described in step 3 of preparation method J.

(Step 6)

A compound represented by the formula 4-6 can be released by the reaction of a compound represented by the formula 5-6 with an acid such as trifluoroacetic acid, where concentration of the acid depends on types of the linker. The reaction solvent used herein is not specifically limited so far as it does not distinctively inhibit the reaction, where a preferable example of which is dichloromethane.

A compound represented by the formula 4-4 in preparation method E, in which "A" is —NR$^1$COR$^2$ substituting the 3-position of the benzene ring, can be prepared also by solid phase synthesis according to preparation method K below.

[Preparation Method K]

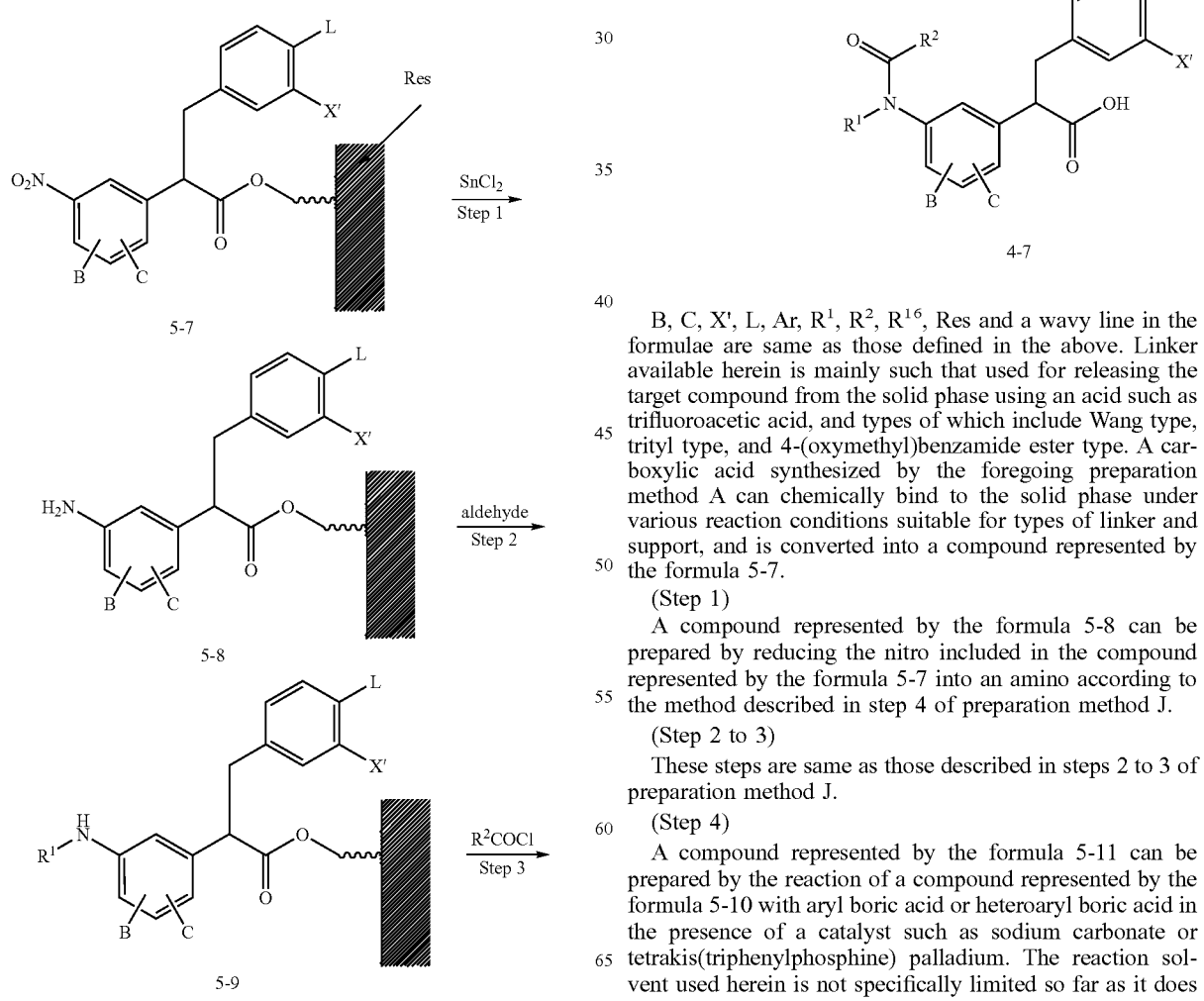

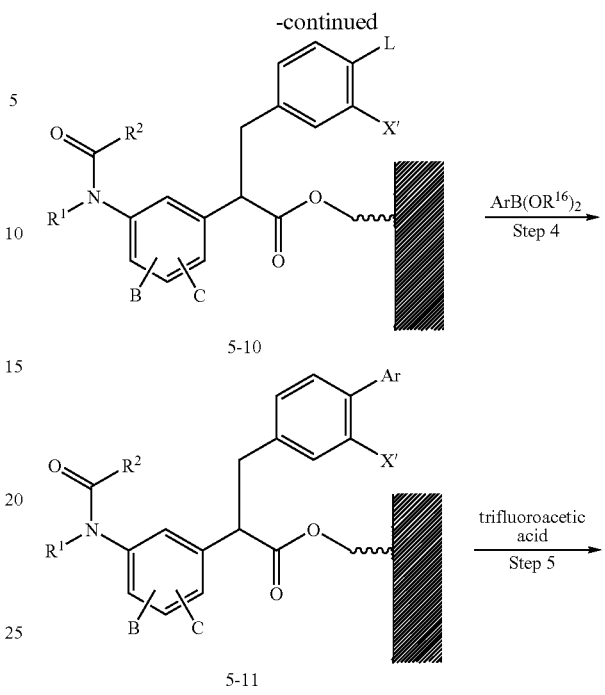

B, C, X', L, Ar, R$^1$, R$^2$, R$^{16}$, Res and a wavy line in the formulae are same as those defined in the above. Linker available herein is mainly such that used for releasing the target compound from the solid phase using an acid such as trifluoroacetic acid, and types of which include Wang type, trityl type, and 4-(oxymethyl)benzamide ester type. A carboxylic acid synthesized by the foregoing preparation method A can chemically bind to the solid phase under various reaction conditions suitable for types of linker and support, and is converted into a compound represented by the formula 5-7.

(Step 1)

A compound represented by the formula 5-8 can be prepared by reducing the nitro included in the compound represented by the formula 5-7 into an amino according to the method described in step 4 of preparation method J.

(Step 2 to 3)

These steps are same as those described in steps 2 to 3 of preparation method J.

(Step 4)

A compound represented by the formula 5-11 can be prepared by the reaction of a compound represented by the formula 5-10 with aryl boric acid or heteroaryl boric acid in the presence of a catalyst such as sodium carbonate or tetrakis(triphenylphosphine) palladium. The reaction solvent used herein is not specifically limited so far as it does not distinctively inhibit the reaction, where examples of (Step 5)

A compound represented by the formula 5-11 can release a compound represented by the formula 4-7 according to the method described in step 6 of preparation method J.

An enantiomer can be obtained as a stereochemically pure isomer by selecting a proper source material, by asymmetric synthesis, or by resolution of racemic compounds. Resolution methods for racemic compounds include optical resolution based on formation of salt with a chiral base, and resolution using a chiral column, which is properly selected depending on properties of the target final product or intermediate. For example, any compounds represented by the formula 3-9 obtained as racemic compounds can be resoluted using a chiral column, to thereby obtain final product having a stereochemical purity.

Of the compounds represented by the formula (1), an optically active compound, having a chiral carbon atom at the 2-position, can be synthesized according to preparation method L below.

[Preparation Method L]

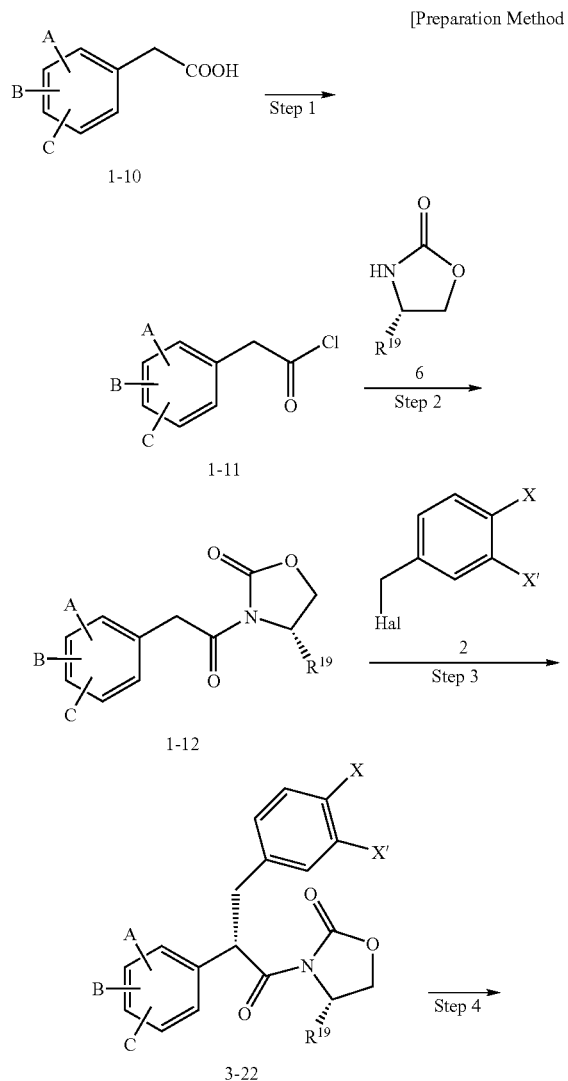

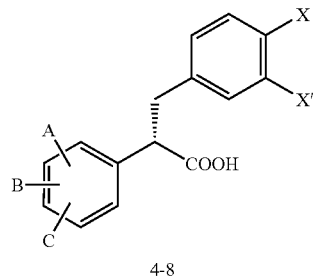

4-8

A, B, C, X, X' and Hal in the formulae are same as those defined in the above, and $R^{19}$ is a $C_{1-10}$ alkyl group.

(Step 1)

An acid chloride represented by the formula 1-11 can be prepared by the reaction of a carboxylic acid represented by the formula 1-10 with oxalyl chloride or thionyl chloride. The reaction solvent used herein is not specifically limited so far as it does not distinctively inhibit the reaction, where examples of which include dichloromethane, 1,2-dichloroethane, chloroform, dimethylformamide, and any arbitrary mixtures thereof.

(Step 2)

A compound represented by the formula 1-12 can be obtained by adding a base such as butyl lithium to a general material for asymmetric synthesis such as an optically active oxazolidinone derivative represented by the formula 6, to thereby obtain a corresponding anion, and the anion is further added to an acid chloride represented by the formula 1-11. The reaction solvent used herein is not specifically limited so far as it does not distinctively inhibit the reaction, where examples of which include tetrahydrofuran, ether, and any arbitrary mixtures thereof.

(Step 3)

A compound represented by the formula 3-22 can be prepared by alkylation of a compound represented by the formula 1-12 according to the method described in step 1 of preparation method "A".

(Step 4)

A compound represented by the formula 4-8 can be prepared by allowing a compound represented by the formula 3-22 to react with a mixed aqueous solution of hydrogen peroxide and lithium hydroxide.

The compound of the present invention possibly prepared by the foregoing preparation methods can be isolated and purified in a form of free compound, salt thereof, various solvates (hydrate, ethanolate, etc.) or crystal polymorphic substance. For the case where the compound of the present invention has a form of salt, a pharmacologically acceptable salt can be produced by the method of the known salt formation reactions. Isolation and purification thereof can be available through chemical processes such as extractive fractionation, crystallization, and various fractional chromatographic techniques.

The 2,3-diphenylpropionic acid derivative of the present invention has a cell adhesion inhibitory effect, and more specifically has an inhibitory effect against α4 integrins. The compound has a particularly excellent antagonistic functions against VLA-4 and/or LPAM-1, and is useful as a remedy or prophylactic for diseases caused by adhesion and infiltration of leukocytes, or diseases in which an adhesive process depending on VLA-4 and/or LPAM-1 play a certain role. Examples of such diseases include autoimmune diseases such as rheumatoid arthritis, systemic lupus erythematosus, multiple sclerosis and Sjoegren's syndrome; various organ inflammations associative therewith; allergic diseases such as asthma, atopic dermatitis, congested nose and rhinitis;

inflammatory bowel diseases including Crohn's disease; nephritis; hepatitis; inflammatory diseases of central nervous system; cardiovascular disease; arteriosclerosis; diabetes; and various malignant tumor. It is also used for preventing damage of transplant organs, or blocking of proliferation and metastasis of tumor.

The compound of the present invention can be administered in a systemic or topical manner by methods such as oral administration, intravenous injection, subcutaneous injection and intrarectal administration, where oral administration is preferable. Dosage form can properly be selected depending on administration routes, and examples of which include tablet, troche, sublingual tablet, sugar-coated tablet, capsule formulation, pill, powder, granule, liquid, emulsion, syrup, inhalant, instillation, nasal drop, injection and suppository. These formulations may be prepared using excipient, antiseptic agent, wetting agent, emulsifier, stabilizer, solubilization aid and so forth.

Dose of the compound of the present invention can properly be determined depending on various conditions such as targets for administration, administration routes and symptom. For example for oral administration to an adult patient, a single dose of the compound of the present invention as an active ingredient is preferably within a range from approx. 0.1 to 100 mg/kg, and more preferably within a range from 1 to 30 mg/kg, and frequency of dose is preferably once to three times a day.

EXAMPLES

The following paragraphs will describe the present invention more specifically referring to examples, by which, however, the present invention is by no means limited.

$^1$H-NMR spectra shown in the following examples were measured using tetramethyl silane (TMS) as an internal standard and using a NMR spectrometer Model JNM-EX270 (270 MHz, JEOL) where δ value is represented in ppm, coupling constant (J) in Hz, and splitting forms were abbreviated as (singlet), d (doublet), t (triplet), q (quartet), m (multiplet) and br (broad). Low-resolution mass spectrum (FABMS) was measured using a fast-atom-bombardment mass spectrometer Model JMS-HX-110 (JEOL). Another low-resolution mass spectrum (ESIMS) was measured using an electrospray ionization mass spectrometer Model LCQ-DECA (Thermo Quese).

In the formulae and Tables shown below, Me is a methyl, Et is an ethyl, Fmoc is 9-fluorenylmethoxycarbonyl, and Res is a solid-phase support resin.

Example 1

Preparation of 3-[4-(2,6-dichlorobenzoyl amino) phenyl]-2-{3-[(2,2-dimethylpropionyl)isobutyl amino]phenyl}propionic acid

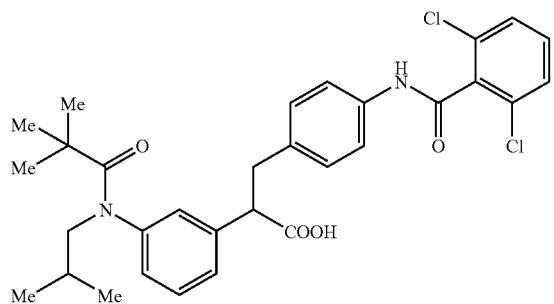

3-Nitrophenylacetic acid (9.78 g, 54 mmol) was dissolved in ethanol (110 mL), added with a concentrated sulfuric acid (1 mL), and the mixture was allowed to reflux under heating for 3 hours. The solvent was evaporated off, and the residue was dissolved in ethyl acetate (300 mL). The solution was successively washed with water and a saturated sodium hydrogen carbonate solution, dried over anhydrous sodium sulfate, evaporated under reduced pressure so as to remove the solvent, to thereby obtain ethyl 3-nitrophenylacetate (yield: 11 g, yield ratio: 97%) as a syrup.

Thus obtained ethyl 3-nitrophenylacetate (5.0 g, 24 mmol) was then dissolved in methanol (80 mL) together with 10 wt % of palladium/carbon (150 mg), and stirred under a hydrogen atmosphere (1 kg/cm$^2$) for 14 hours. The reaction solution was filtered through Celite so as to remove the palladium/carbon catalyst, evaporated under reduced pressure so as to remove the solvent, and the residue was purified through silica gel column chromatography (hexane: ethyl acetate (v/v)=7:3) to thereby obtain a purified ethyl 3-aminophenylacetate (yield: 4.0 g, yield ratio: 100%) as a syrup.

The ethyl 3-aminophenylacetate (1.15 g, 6.4 mmol) and isobutylaldehyde (0.58 mL, 6.4 mmol) were dissolved in an absolute methanol (100 mL). The solution was added with sodium triacetoxyborohydride (3.39 g, 16 mmol) and acetic acid (1 drop), and stirred for 14 hours. The solvent was evaporated under reduced pressure, and the resultant residue was added with water. The solution was extracted using ethyl acetate, dried over anhydrous sodium sulfate, evaporated under reduced pressure so as to remove the solvent, and the residue was purified through silica gel column chromatography (hexane:ethyl acetate (v/v)=8:1 to 4:1) to thereby obtain ethyl 3-(isobutylamino)phenylacetate (yield: 1.32 g, yield ratio: 87%) as a syrup.

The ethyl 3-(isobutylamino)phenylacetate (1.32 g, 5.6 mmol) was dissolved in chloroform (25 mL), and added with triethylamine (1.4 mL, 10 mmol). The mixture was further added with pivaloyl chloride (1.03 mL, 8.4 mmol) at 0° C., and stirred for 3 hours at room temperature. The mixture was treated with a 1 mol/L hydrochloric acid (20 mL), extracted with chloroform, dried over anhydrous sodium sulfate, evaporated under reduced pressure so as to remove the solvent, and the resultant residue was purifier by purified through silica gel column chromatography (hexane:ethyl acetate (v/v)=4:1) to thereby obtain 3-[(2,2-dimethylpropionyl)isobutyl-amino]phenylacetic acid ethyl ester (yield: 1.76 g, yield ratio: 99%).

Diisopropylamine (0.65 mL, 4.6 mmol) was dissolved in tetrahydrofuran (20 mL), and the solution was added drop-wisely with a 1.5 mol/L hexane solution of n-butyllithium (2.8 mL, 4.2 mmol) at −78° C., stirred for 30 minutes to thereby prepare lithium diisopropylamide. Into the lithium diisopropylamide solution, a tetrahydrofuran solution (5 mL) of 3-[(2,2-dimethylpropionyl) isobutylamino]phenylacetic acid ethyl ester was drop-wisely added while keeping the temperature of the solution at −78° C. The mixture was stirred at −78° C. for 1 hour, and a tetrahydrofuran solution (10 mL) of 4-nitrobenzyl bromide (972 mg, 4.5 mmol) was drop-wisely added thereto. The mixture was then heated to room temperature, and was further stirred for 1 hour. The resultant solution was washed with a saturated ammonium chloride solution and was then extracted using ethyl acetate. The extract was dried over anhydrous sodium sulfate, evaporated under reduced pressure so as to remove the solvent, and the resultant residue was purified through silica gel column chromatography (hexane:ethyl acetate (v/v)=4: 1) to thereby obtain 3-(4-nitrophenyl)-2-{3-[(2,2-dimethyl-propionyl)isobutylamino]phenyl}propionic acid ethyl ester (yield: 1.57 g, yield ratio: 99%).

Thus obtained 3-(4-nitrophenyl)-2-{3-[(2,2-dimethyl propionyl)isobutylamino]phenyl}propionic acid ethyl ester (1.55 g, 3.4 mmol) and 10 wt % of palladium/carbon (100 mg) were dissolved in methanol (20 mL), and stirred under a hydrogen atmosphere (1 kg/cm$^2$) for 14 hours. The mixture was filtered through Celite so as to remove the palladium/carbon catalyst, evaporated under reduced pressure so as to remove the solvent, and the resultant residue was dissolved in chloroform (30 mL). The solution was added with triethylamine (1.5 mL, 10.5 mmol), further added with 2,6-dichlorobenzoyl chloride (1.08 mL, 7.5 mmol) at 0° C., and was stirred for 15 hours. The mixture was then treated with a 1 mol/L hydrochloric acid (15 mL), extracted with chloroform, dried over anhydrous sodium sulfate, evaporated under reduced pressure so as to remove the solvent, and the resultant residue was purified through silica gel column chromatography (hexane:ethyl acetate (v/v)=2:1) to thereby obtain 3-[4-(2,6-dichlorobenzoylamino)phenyl]-2-{3-[(2,2-dimethyl propionyl)isobutylamino]phenyl}propionic acid ethyl ester (yield: 1.7 g, yield ratio: 83%) as a solid.

Thus obtained 3-[4-(2,6-dichlorobenzoyl amino) phenyl]-2-{3-[(2,2-dimethylpropionyl)isobutylamino] phenyl}propionic acid ethyl ester (1.7 g, 2.8 mmol) was dissolved in a mixed solvent of methanol (15 mL) and tetrahydrofuran (15 mL), and added with a 2 mol/L aqueous sodium hydroxide solution (15 mL, 30 mmol). The solvent was evaporated under reduced pressure, and the resultant residue was added with water to solubilize, and washed with diethyl ether. The separated aqueous phase was added with a 1 mol/L hydrochloric acid solution so as to adjust pH of the solution to as low as below 4. The solution was extracted with ethyl acetate, dried over anhydrous sodium sulfate, and evaporated under reduced pressure so as to remove the solvent, to thereby obtain 3-[4-(2,6-dichlorobenzoylamino) phenyl]-2-{3-[(2,2-dimethylpropionyl)isobutylamino] phenyl}propionic acid (yield: 1.6 g, yield ratio: 99%) as a light-yellow solid.

Physical properties of the compound were listed in Table 1.

Example 2

Preparation of 3-[4-(2,6-dichlorobenzoyl amino) phenyl]-2-{3-[(2-ethylbutylyl)isobutylamino] phenyl}propionic acid

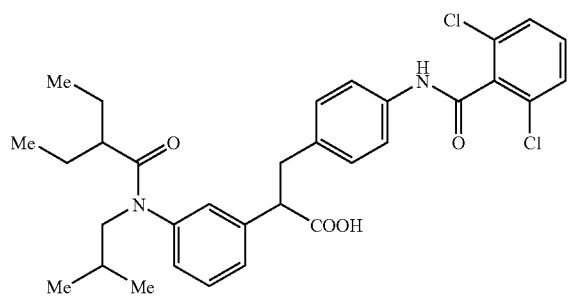

2-(3-aminophenyl)-3-(4-nitrophenyl)propionic acid ethyl ester (6.79 g, 2.16 mmol) was dissolved in chloroform (80 mL), added with di-tert-butyl bicarbonate (7.2 g, 33 mmol) and 4-dimethylaminopyridine (10 mg), and the mixture was stirred at 60° C. for 8 hours. The mixture was treated with a 0.5 mol/L hydrochloric acid (80 mL). The reaction solution was extracted with chloroform, the extract was dried over anhydrous sodium sulfate, the solvent was then evaporated under reduced pressure, and the resultant residue was purified through silica gel column chromatography (hexane:ethyl acetate (v/v)=4:1) to thereby obtain 2-(3-tert-butoxycarbonylaminophenyl)-3-(4-nitrophenyl)propionic acid ethyl ester (yield: 6.05 g, yield ratio: 68%) as a light-yellow syrup.

Thus obtained 2-(3-tert-butoxycarbonylamino phenyl)-3-(4-nitrophenyl)propionic acid ethyl ester (5.05 g, 12.2 mmol) and 10 wt % of palladium/carbon (150 mg) were dissolved in methanol (60 mL), and stirred under a hydrogen atmosphere (3 kg/cm$^2$) for 3 hours. The mixture was filtered through Celite so as to remove the palladium/carbon catalyst, concentrated under reduced pressure, evaporated under reduced pressure so as to remove the solvent, and the residue was added with chloroform (60 mL) and triethylamine (4.2 mL, 30 mmol). The mixture was further added with 2,6-dichlorobenzoyl chloride (2.87 mL, 20 mmol) and stirred for 2 hours. The reaction mixture was treated with a 0.5 mol/L hydrochloric acid (50 mL). The mixture was extracted with chloroform, the extract was dried over anhydrous sodium sulfate, evaporated under reduced pressure so as to remove the solvent, and the resultant residue was purified through silica gel column chromatography (hexane:ethyl acetate (v/v)=2:1 to 3:2) to thereby obtain 2-(3-tert-butoxycarbonylaminophenyl)-3-[4-(2,6-dichloro benzoylamino)phenyl] propionic acid ethyl ester (yield: 7.02 g, yield ratio: 103%) containing a trace amount of solvent as a white solid.

Thus obtained 2-(3-tert-butoxycarbonylaminophenyl)-3-[4-(2,6-dichlorobenzoyl amino)phenyl]propionic acid ethyl ester (1.50 g, 27 mmol) was dissolved in ethyl acetate (14 mL), added with a 4 mol/L hydrogen chloride solution in ethyl acetate (14 mL), and stirred at room temperature for 4 hours. The solvent was evaporated under reduced pressure, and the resultant residue was added with an aqueous saturated sodium hydrogen carbonate solution so as to adjust pH of the solution as high as 7 or above, extracted with ethyl acetate, dried over anhydrous sodium sulfate, and evaporated under reduced pressure so as to remove the solvent to thereby obtain 2-(3-aminophenyl)-3-[4-(2,6-dichlorobenzoylamino)phenyl]propionic acid ethyl ester (yield: 1.23 g, yield ratio: 100%) as a white solid.

Thus obtained 2-(3-aminophenyl)-3-[4-(2,6-dichloro Benzoylamino)phenyl]propionic acid ethyl ester (1.64 g, 3.6 mmol) and isobutylaldehyde (0.363 mL, 4.0 mmol) were dissolved in absolute methanol (20 mL). The mixture was further added with sodium triacetoxyborohydride (2.29 g, 10.8 mmol) and acetic acid (one drop), and stirred for 14 hours. The solvent was evaporated under reduced pressure, and the resultant residue was added with water, the solution was extracted with ethyl acetate, dried over anhydrous sodium sulfate, evaporated under reduced pressure so as to remove the solvent, and the resultant residue was purified through silica gel column chromatography (hexane:ethyl acetate (v/v)=3:1) to thereby obtain 3-[4-(2,6-dichlorobenzoylamino)phenyl]-2-[(3-isobutyl amino)phenyl]propionic acid ethyl ester (yield: 697 mg, yield ratio: 38%) as a white solid.

Thus obtained 3-[4-(2,6-dichlorobenzoyl amino) phenyl]-2-[(3-isobutylamino)phenyl]propionic acid ethyl ester (51 mg, 0.1 mmol) was dissolved in chloroform (2 mL), and added with triethylamine (0.042 mL, 0.3 mmol). The mixture was further added with 2-ethylbutylyl chloride (0.028 mL, 0.2 mmol) at 0° C., and stirred at room temperature for 2 hours. The reaction mixture was treated with a 1 mol/L hydrochloric acid (20 mL). The mixture was extracted with chloroform, dried over anhydrous sodium sulfate, evaporated under reduced pressure so as to remove the solvent, and the resultant residue was purified silica gel thin layer chromatography (hexane:ethyl acetate (v/v)=3:2) to thereby obtain 3-[4-(2,6-dichlorobenzoyl amino)phenyl]-2-{3-[(2-ethylbutylyl) isobutylamino]phenyl}propionic acid ethyl ester (yield: 64 mg, yield ratio: 105%) as a white crystal containing a trace amount of solvent.

Thus obtained 3-[4-(2,6-dichlorobenzoyl amino) phenyl]-2-{3-[(2-ethylbutylyl)isobutylamino]phenyl} propionic acid ethyl ester (64 mg, 0.1 mmol) was dissolved in a mixed solvent of methanol (2 mL) and tetrahydrofuran (2 mL), and the mixture was further added with a 2 mol/L aqueous sodium hydroxide solution (2 mL, 4 mmol). The solvent was evaporated under reduced pressure, and the resultant residue was added with water to solubilize, and washed with diethyl ether. The separated aqueous phase was added with a 1 mol/L hydrochloric acid so as to adjust pH of the solution as low as 4 or below. The solution was then extracted with ethyl acetate, dried over anhydrous sodium sulfate, evaporated under reduced pressure so as to remove the solvent to thereby obtain 3-[4-(2,6-dichlorobenzoyl amino)phenyl]-2-{3-[(2-ethylbutylyl)isobutylamino]phenyl}propionic acid (yield: 47 mg, yield ratio: 77%) as a white solid.

Compounds of Examples 3 to 29 shown in Tables 1 and 2 below were also prepared similarly to Example 2. Physical properties of these compounds are shown in Tables 1 and 2.

TABLE 1

| Example No. | R¹ | R² | NMR, MS |
|---|---|---|---|
| 1 | isobutyl (CH(Me)₂ with extra CH₂) — iPr-CH₂ | tBu | ¹H-NMR(CDCl₃)δ: 0.85(3H, d, J=1.0Hz), 0.87(3H, d, J=1.0Hz), 1.73(1H, m), 3.02(1H, dd, J=6.9, 13.9Hz), 3.36-3.46(3H, m), 3.87(1H, t, J=7.8Hz), 7.08-7.18(4H, m), 7.22-7.31(3H, m), 7.35(2H, d, J=5.0Hz), 7.55(2H, d, J=8.3Hz), 7.96(1H, s). FABMS: 569(M+H)⁺. |
| 2 | isobutyl | 2-ethylbutyl | ¹H-NMR(CDCl₃)δ: 0.61-0.80(6H, m), 0.86(3H, d, J=2.0Hz), 0.89(3H, d, J=2.0Hz), 1.18-1.36(2H, m), 1.43-1.60(2H, m), 1.68(1H, m), 1.97(1H, m), 3.02(1H, dd, J=6.8, 13.7Hz), 3.41(1H, dd, J=8.9, 13.9Hz), 3.47-3.58(2H, m), 3.86(1H, t, J=7.8Hz), 7.02-7.15(4H, m), 7.20-7.31(3H, m), 7.38(2H, d, J=5.3Hz), 7.56(2H, d, J=8.6Hz), 8.06(1H, s). FABMS: 583(M+H)⁺. |
| 3 | isobutyl | —Me | ¹H-NMR(CDCl₃)δ: 0.84(3H, d, J=1.6Hz), 0.86(3H, d, J=1.7Hz), 1.66(1H, m), 1.71(3H, s), 3.02(1H, dd, J=6.9, 13.5Hz), 3.41(1H, dd, J=8.6, 13.9Hz), 3.48(2H, d, J=7.6Hz), 3.87(1H, dd, J=7.3, 7.9Hz), 7.02-7.16(4H, m), 7.17-7.43(5H, m), 7.53(2H, d, J=8.2Hz), 8.07(1H, s). FABMS: 527(M+H)⁺. |
| 4 | isobutyl | —Et | ¹H-NMR(CDCl₃)δ: 0.84(3H, d, J=1.6Hz), 0.86(3H, d, J=1.7Hz), 1.67(1H, m), 1.92(2H, q, J=7.5Hz), 3.02(1H, dd, J=6.9, 13.9Hz), 3.34-3.52(3H, m), 3.87(1H, t, J=7.6Hz), 7.02-7.14(4H, m), 7.19-7.30(3H, m), 7.37(2H, d, J=4.6Hz), 7.55(2H, d, J=8.2Hz), 8.04(1H, s). FABMS: 541(M+H)⁺. |
| 5 | isobutyl | iPr | ¹H-NMR(CDCl₃)δ: 0.80-1.00(12H, m), 1.68(1H, m), 2.29(1H, m), 3.03(1H, dd, J=7.1, 13.7Hz), 3.36-3.51(3H, m), 3.87(1H, t, J=7.6Hz), 7.03-7.14(4H, m), 7.22-7.30(3H, m), 7.38(2H, d, J=4.4Hz), 7.55(2H, d, J=8.2Hz), 8.01(1H, s). FABMS: 555(M+H)⁺. |
| 6 | isobutyl | cyclopropyl | ¹H-NMR(CDCl₃)δ: 0.46-0.61(2H, m), 0.77-0.98(8H, m), 1.17(1H, m), 1.69(1H, m), 3.03(1H, dd, J=6.9, 13.5Hz), 3.35-3.58(3H, m), 3.87(1H, t, J=7.8Hz), 7.08-7.43(9H, m), 7.54(2H, d, J=8.2Hz), 8.00(1H, s). FABMS: 553(M+H)⁺. |
| 7 | isobutyl | cyclohexyl | ¹H-NMR(CDCl₃)δ: 0.76-0.97(7H, m), 1.09(1H, m), 1.34-1.76(8H, m), 2.03(1H, m), 3.02(1H, dd, J=6.3, 13.5Hz), 3.34-3.53(3H, m), 3.89(1H, t, J=7.4Hz), 7.02-7.41 (9H, m), 7.57(2H, d, J=8.6Hz), 7.97(1H, s). FABMS: 595(M+H)⁺. |

TABLE 1-continued

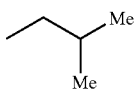

| Example No. | R¹ | R² | NMR, MS |
|---|---|---|---|
| 8 | 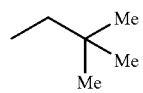 | 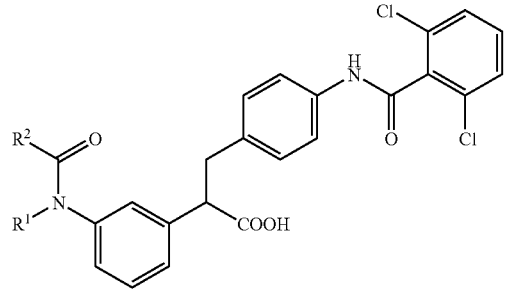 | ¹H-NMR(CDCl₃)δ: 0.87(6H, d, J=11.2Hz), 0.89(9H, s), 1.65-1.70(1H, m), 1.91(2H, s), 2.98-3.05(1H, m), 3.36-3.50(3H, m), 3.87(1H, t, J=7.3Hz), 7.02-7.39(7H, m), 7.13(2H, d, J=7.9Hz), 7.56(2H, d, J=7.9Hz), 8.08(1H, s). FABMS: 583(M+H)⁺. |
| 9 | 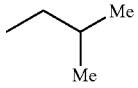 | 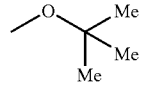 | ¹H-NMR(CDCl₃)δ: 0.83(3H, d, J=1.3Hz), 0.86(3H, d, J=1.3Hz), 1.38(9H, s), 1.71(1H, m), 2.98(1H, dd, J=5.3, 13.5Hz), 3.39(1H, m), 3.44(2H, d, J=7.3Hz), 3.80(1H, dd, J=5.4, 9.7Hz), 7.06-7.32(9H, m), 7.56(2H, d, J=8.3Hz), 8.03(1H, s). FABMS: 585(M+H)⁺. |
| 10 | 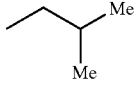 | 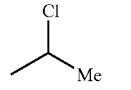 | ¹H-NMR(CDCl₃)δ: 0.84-0.91(6H, m), 1.49(3H, br s), 1.69-1.75(1H, m), 2.99-3.07(1H, m), 3.29-3.49(2H, m), 3.59-3.71(1H, m), 3.88(1H, m), 4.04-4.07(1H, m), 7.10-7.26(7H, m), 7.42(2H, br s), 7.55(2H, d, J=7.6Hz), 7.95(1H, s). FABMS: 575(M+H)⁺. |
| 11 | 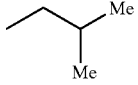 | 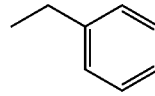 | ¹H-NMR(CDCl₃)δ: 0.82(3H, d, J=2.6Hz), 0.85(3H, d, J=2.6Hz), 1.66(1H, m), 2.94(1H, dd, J=6.6, 13.5Hz), 3.25-3.41(3H, m), 3.49(2H, d, J=7.6Hz), 3.79(1H, m), 6.88-7.00(4H, m), 7.05-7.41(10H, m), 7.50(2H, d, J=8.3Hz), 7.74(1H, br s). FABMS: 603(M+H)⁺. |
| 12 | 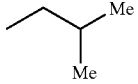 | 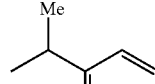 | ¹H-NMR(CDCl₃)δ: 0.76-0.88(6H, m), 1.25-1.33(3H, m), 1.62-1.65(1H, m), 2.91(1H, m), 3.40-3.49(4H, m), 3.74(1H, m), 6.90(2H, d, J=6.6Hz), 7.11-7.37(12H, m), 7.53-7.58(2H, m), 7.97(1H, s). FABMS: 617(M+H)⁺. |
| 13 | 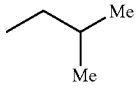 | 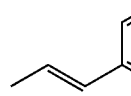 | ¹H-NMR(CDCl₃)δ: 0.88(6H, d, J=6.6Hz), 1.76(1H, m), 3.02(1H, dd, J=6.8, 13.7Hz), 3.41(1H, dd, J=8.4, 13.7Hz), 3.57-3.72(2H, m), 3.88(1H, t, J=7.6Hz), 6.22(1H, d, J=15.5Hz), 7.06-7.30(12H, m), 7.34-7.43(2H, m), 7.48(2H, d, J=8.3Hz), 7.63(1H, d, J=15.5Hz), 7.83(1H, br s). FABMS: 615(M+H)⁺. |
| 14 | 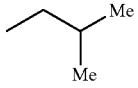 | 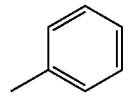 | ¹H-NMR(CDCl₃)δ: 0.92(3H, d, J=1.0Hz), 0.94(3H, d, J=1.0Hz), 1.89(1H, m), 2.71(1H, dd, J=6.3, 13.9Hz), 3.18(1H, dd, J=9.2, 13.5Hz), 3.67(1H, dd, J=6.4, 8.7Hz), 3.76(2H, d, J=7.6Hz), 6.91-7.30(14H, m), 7.53(2H, d, J=8.6Hz), 8.07(1H, s). FABMS: 589(M+H)+. FABMS: 589(M+H)⁺. |
| 15 | 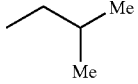 | 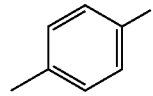 | ¹H-NMR(CDCl₃)δ: 0.96(6H, d, J=6.6Hz), 1.84(1H, m), 2.66(1H, dd, J=5.8, 13.7Hz), 3.17(1H, dd, J=9.7, 13.5Hz), 3.54-3.68(4H, m), 3.76(2H, d, J=7.6Hz), 6.55(1H, d, J=8.3Hz), 6.71(1H, t, J=7.3Hz), 6.94-7.30(11H, m), 7.53(2H, d, J=8.6Hz), 7.99(1H, s). FABMS: 619(M+H)⁺. |
| 16 | 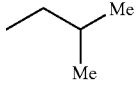 | 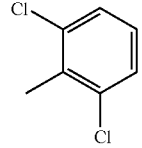 | ¹H-NMR(DMSO-d₆)δ: 0.92(6H, d, J=6.6Hz), 1.65(1H, m), 2.68(1H, dd, J=8.3, 13.9Hz), 3.11(1H, dd, J=7.4, 13.7Hz), 3.58-3.83(3H, m), 6.95(2H, d, J=8.6Hz), 7.06(1H, d, J=7.3Hz), 7.12-7.37(6H, m), 7.42-7.63(5H, m), 10.63(1H, s), 12.38(1H, br s). FABMS: 657(M+H)⁺. |

TABLE 1-continued

[Structure: core compound with R²−C(=O)−N(R¹)− attached to 3-position of a phenyl group bearing −CH(COOH)−CH₂− linker to 4-[(2,6-dichlorobenzoyl)amino]phenyl]

| Example No. | R¹ | R² | NMR, MS |
|---|---|---|---|
| 17 | sec-butyl (CH(Me)Et) | 2-furyl | ¹H-NMR(CDCl₃)δ: 0.90(3H, d, J=1.3Hz), 0.93(3H, d, J=1.0Hz), 1.83(1H, m), 2.99(1H, dd, J=6.9, 13.9Hz), 3.37(1H, dd, J=8.4, 13.7Hz), 3.66(2H, d, J=7.3Hz), 3.87(1H, t, J=7.6Hz), 5.62(1H, d, J=3.3Hz), 6.11(1H, dd, J=1.7, 3.6Hz), 7.04-7.30(8H, m), 7.36(2H, d, J=5.0Hz), 7.40(2H, d, J=8.2Hz), 8.04(1H, s). FABMS: 579(M+H)⁺. |
| 18 | sec-butyl (CH(Me)Et) | 2-thienyl | ¹H-NMR(CDCl₃)δ: 0.93(6H, d, J=6.6Hz), 1.87(1H, m), 2.98(1H, dd, J=6.9, 13.9Hz), 3.36(1H, dd, J=8.6, 13.9Hz), 3.68(2H, d, J=7.3Hz), 3.87(1H, t, J=7.8Hz), 6.64(1H, d, J=3.6Hz), 6.70(1H, m), 7.07-7.30(8H, m), 7.37(2H, d, J=5.0Hz), 7.54(2H, d, J=8.2Hz), 8.01(1H, s). FABMS: 595(M+H)⁺. |
| 19 | n-pentyl | tert-butyl (CMe₃) | ¹H-NMR(CDCl₃)δ: 0.84(3H, t, J=6.8Hz), 0.92(9H, s), 1.13-1.32(4H, m), 1.40-1.56(2H, m), 3.02(1H, dd, J=6.9, 13.9Hz), 3.42(1H, dd, J=8.4, 13.7Hz), 3.52(2H, dd, J=5.9, 8.9Hz), 3.87(1H, t, J=7.6Hz), 7.05-7.20(4H, m), 7.22-7.38(5H, m), 7.54(2H, d, J=8.2Hz), 7.80(1H, s). FABMS: 583(M+H)⁺. |
| 20 | benzyl | tert-butyl (CMe₃) | ¹H-NMR(CDCl₃)δ: 0.95(9H, s), 2.85(1H, dd, J=6.6, 13.9Hz), 3.27(1H, dd, J=8.7, 13.7Hz), 3.74(1H, dd, J=6.8, 8.7Hz), 4.72(1H, d, J=14.2Hz), 4.82(1H, d, J=14.2Hz), 6.86-6.95(2H, m), 7.03-7.12(4H, m), 7.17-7.29(8H, m), 7.53(2H, d, J=8.6Hz), 7.91(1H, s). FABMS: 603(M+H)⁺. |
| 21 | —Me | benzyl | FABMS: 561(M+H)⁺. |
| 22 | —H | benzyl | ¹H-NMR(CDCl₃)δ: 3.02(1H, dd, J=6.6, 13.9Hz), 3.38(1H, dd, J=8.6, 13.9Hz), 3.82(1H, t, J=7.6Hz), 7.07-7.32(7H, m), 7.38-7.59(6H, m), 7.74(1H, d, J=7.9Hz), 7.88(2H, d, J=6.9Hz), 8.58(1H, s), 8.80(1H, s). FABMS: 533(M+H)⁺. |
| 23 | —H | benzyl | ¹H-NMR(CDCl₃)δ: 2.98(1H, dd, J=6.8, 13.7Hz), 3.35(1H, dd, J=8.6, 13.9Hz), 3.67(2H, s), 3.76(1H, dd, J=7.6, 7.6Hz), 7.04-7.39(13H, m), 7.49-7.51(3H, m), 8.24(1H, s), 9.07(1H, s). FABMS: 547(M+H)⁺. |
| 24 | —H | 2-phenylethyl | ¹H-NMR(CDCl₃)δ: 2.63(2H, t, J=7.8Hz), 2.94-3.07(3H, m), 3.36(1H, dd, J=8.4, 13.7Hz), 3.77(1H, t, J=7.6Hz), 7.05-7.36(13H, m), 7.54(2H, d, J=8.2Hz), 7.61(1H, d, J=8.3Hz), 8.42(1H, s), 9.13(1H, s). FABMS: 561(M+H)⁺. |
| 25 | —H | cyclohexylmethyl | ¹H-NMR(CDCl₃)δ: 1.13-1.38(4H, m), 1.39-1.95(6H, m), 2.23(1H, m), 3.00(1H, dd, J=6.9, 13.7Hz), 3.37(1H, dd, J=8.9, 13.9Hz), 3.79(1H, t, J=7.6Hz), 7.03-7.37(7H, m), 7.42(1H, s), 7.54(2H, d, J=8.2Hz), 7.63(1H, d, J=7.9Hz), 7.99(1H, s), 8.98(1H, s). FABMS: 539(M+H)⁺. |

TABLE 1-continued

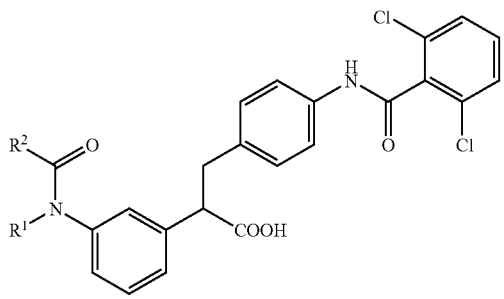

| Example No. | R¹ | R² | NMR, MS |
|---|---|---|---|
| 26 | —H | 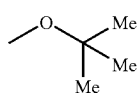 | ¹H-NMR(CDCl₃)δ: 1.48(9H, s), 2.94(1H, dd, J=5.3, 13.9Hz), 3.36(1H, dd, J=9.9, 13.9Hz), 3.77(1H, dd, J=5.3, 9.9Hz), 7.00(1H, d, J=7.6Hz), 7.12-7.35(8H, m), 7.51(2H, d, J=8.3Hz), 8.06(1H, m). FABMS: 529(M+H)⁺. |

TABLE 2

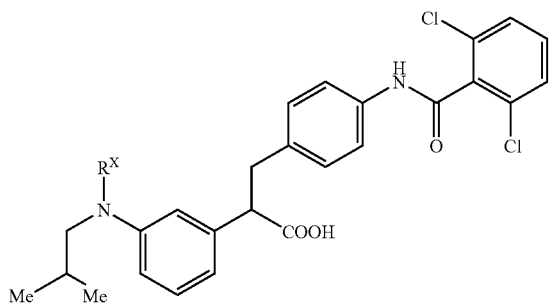

| Example No. | Rˣ | NMR, MS |
|---|---|---|
| 27 | H— | ¹H-NMR(CDCl₃)δ: 0.97(6H, d, J=6.6Hz), 1.86(1H, m), 2.85-3.00(3H, m), 3.38(1H, dd, J=10.6, 13.5Hz), 3.72(1H, dd, J=4.6, 10.2Hz), 6.51(1H, d, J=7.9Hz), 6.59(1H, s), 6.68(1H, d, J=7.6Hz), 7.07-7.19(6H, m), 7.56(2H, d, J=8.3Hz), 8.00(1H, s). FABMS: 485(M+H)⁺. |
| 28 | 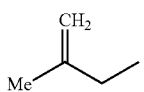 | ¹H-NMR(CDCl₃)δ: 0.92(6H, d, J=5.9Hz), 1.68(3H, s), 2.03(1H, m), 2.96(1H, dd, J=5.0, 13.5Hz), 3.10(2H, d, J=7.3Hz), 3.38(1H, dd, J=10.2, 13.5Hz), 3.72(1H, dd, J=5.1, 10.1Hz), 3.81(2H, s), 4.67(1H, s), 4.79(1H, s), 6.46-6.59(2H, m), 6.63(1H, d, J=7.6Hz), 7.07-7.30(6H, m), 7.55(2H, d, J=8.6Hz), 7.94(1H, s). FABMS: 539(M+H)⁺. |
| 29 | 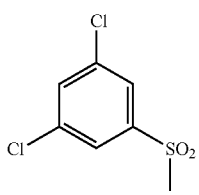 | ¹H-NMR(CDCl₃)δ: 0.87(3H, d, J=5.3Hz), 0.90(3H, d, J=5.3Hz), 1.54(1H, m), 2.92(1H, dd, J=5.6, 13.9Hz), 3.22-3.37(3H, m), 3.79(1H, dd, J=5.6, 9.9Hz), 7.01-7.05(2H, m), 7.12-7.42(9H, m), 7.49(1H, m), 7.55(2H, d, J=8.6Hz), 8.00(1H, s). FABMS: 693(M+H)⁺. |

Example 38

Preparation of 3-[4-(2,6-dichlorobenzoyl amino) phenyl]-2-{3-[(2,2-dimethylpropionyl)isobutyl amino]-4-methoxyphenyl}propionic acid

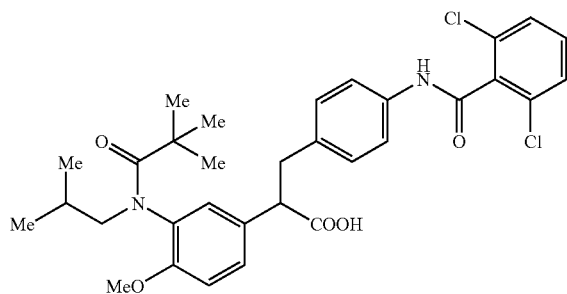

4-hydroxy-3-nitrophenylacetic acid ethyl ester (28.2 g, 125 mmol) was dissolved in acetone (700 mL), the solution was added with methyl iodide (23.39 mL, 376 mmol) in the presence of potassium carbonate (86.53 g, 626 mmol), and refluxed under heating for 3 hours. The solid matter was filtered off, the filtrate was evaporated under reduced pressure so as to remove the solvent, and the resultant residue was dissolved in ethyl acetate. The solution was washed with brine, dried over anhydrous sodium sulfate, evaporated under reduced pressure so as to remove the solvent, and the resultant residue was purified through silica gel column chromatography (hexane:ethyl acetate (v/v)=3:1) to thereby obtain 4-methoxy-3-nitrophenylacetic acid ethyl ester (yield: 29.60 g, yield ratio: 99%).

Thus obtained 4-methoxy-3-nitrophenylacetic acid ethyl ester (8.40 g, 35 mmol) and 10 wt % of palladium/carbon (800 mg) were dissolved in methanol (130 mL), and stirred under a hydrogen atmosphere (3 kg/cm$^2$) for 5 hours. The reaction mixture was filtered through Celite so as to remove the palladium/carbon catalyst, concentrated under reduced pressure, evaporated under reduced pressure so as to remove the solvent, and the resultant residue was purified through silica gel column chromatography (hexane:ethyl acetate (v/v)=2:1) to thereby obtain 3-amino-4-methoxyphenylacetic acid ethyl ester (yield: 6.12 g, yield ratio: 83%) as a yellow syrup.

Thus obtained 3-amino-4-methoxyphenylacetic acid ethyl ester (6.06 g, 29 mmol) was dissolved in toluene (200 mL), added with benzaldehyde (2.94 mL, 29 mmol), and refluxed under heating at 130° C. for 14 hours. The reaction mixture was cooled to room temperature, evaporated under reduced pressure so as to remove the solvent, and the resultant residue was dissolved in tetrahydrofuran (200 mL), and added drop-wisely with a 2 mol/L lithium diisopropylamide solution (heptane/tetrahydrofuran/ethylbenzene solution, 15.9 mL, 32 mmol) while keeping the temperature thereof at −78° C. The mixture was heated to −20° C., stirred for 10 minutes, cooled again to −78° C., and at that temperature added drop-wisely with a tetrahydrofuran solution (80 mL) of 4-nitrobenzyl bromide (6.88 g, 32 mmol). The mixture was then heated to room temperature, and 2-[3-(benzylideneamino)-4-methoxy phenyl]-3-(4-nitrophenyl)propionic acid ethyl ester was produced in the reaction solution. Next as a series of processing, the reaction solution was then treated with a 1 mol/L hydrochloric acid (150 mL), the separated aqueous phase was added with an aqueous saturated sodium hydrogen carbonate solution so as to adjust pH of the solution as high as 7 or above, and extracted with ethyl acetate, which series was repeated three times. The ethyl acetate phase was dried over anhydrous sodium sulfate, evaporated under reduced pressure so as to remove the solvent, and the resultant residue was purified through silica gel column chromatography (hexane:ethyl acetate (v/v)=2:1) to thereby obtain 2-(3-amino-4-methoxyphenyl)-3-(4-nitrophenyl)propionic acid ethyl ester (yield: 5.63 g, yield ratio: 56%) as an orange syrup.

$^1$H-NMR (CDCl$_3$) δ value: 1.14 (3H, t, J=7.1 Hz), 3.07 (1H, dd, J=7.1, 13.7 Hz), 3.42 (1H, dd, J=8.4, 13.7 Hz), 3.68 (1H, t, J=7.8 Hz), 3.72-3.93 (2H, m), 3.83 (3H, s), 3.96-4.17 (2H, m), 6.58 (1H, dd, J=2.0, 8.3 Hz), 6.64-6.72 (2H, m), 7.27 (2H, d, J=8.6 Hz), 8.09 (2H, d, J=8.6 Hz).

FABMS: 345 (M+H)$^+$.

Thus obtained 2-(3-amino-4-methoxyphenyl)-3-(4-nitrophenyl)propionic acid ethyl ester (3.57 g, 10.4 mmol) and isobutylaldehyde (1.41 mL, 15.5 mmol) were dissolved in absolute methanol (100 mL). The mixture was added with sodium triacetoxyborohydride (6.59 g, 31 mmol) and acetic acid (one drop), and stirred for 14 hours. The solvent was evaporated under reduced pressure, and the resultant residue was added with water. The solution was extracted with ethyl acetate, the extract was dried over anhydrous sodium sulfate, evaporated under reduced pressure so as to remove the solvent, and the resultant residue was purified through silica gel column chromatography (hexane:ethyl acetate (v/v)=6:1 to 3:1) to thereby obtain 2-[(3-isobutylamino)-4-methoxyphenyl]-3-(4-nitrophenyl)propionic acid ethyl ester (yield: 3.17 g, yield ratio: 76%) as an orange syrup.

$^1$H-NMR (CDCl$_3$) δ value: 0.97 (3H, d, J=1.6 Hz), 0.99 (3H, d, J=1.6 Hz), 1.15 (3H, t, J=7.1 Hz), 1.86 (1H, m), 2.91 (2H, d, J=6.9 Hz), 3.10 (1H, dd, J=7.1, 13.7 Hz), 3.45 (1H, dd, J=8.4, 13.7 Hz), 3.71 (1H, t, J=7.6 Hz), 3.82 (3H, s), 3.95-4.18 (2H, m), 4.29 (1H, br s), 6.43-6.53 (2H, m), 6.65 (1H, d, J=8.3 Hz), 7.28 (2H, d, J=8.6 Hz), 8.09 (2H, d, J=8.6 Hz).

FABMS: 401 (M+H)$^+$.

Thus obtained 2-[(3-isobutylamino)-4-methoxy phenyl]-3-(4-nitrophenyl)propionic acid ethyl ester (328 mg, 0.82 mmol) was dissolved in chloroform (5 mL), and added with triethylamine (0.418 mL, 3 mmol). The mixture was further added with pivaloyl chloride (0.246 mL, 2 mmol) at 0° C., and then stirred at room temperature for one hour. The reaction solution was treated with a 1 mol/L hydrochloric acid (20 mL). The solution was extracted with chloroform, the extract was dried over anhydrous sodium sulfate, evaporated under reduced pressure so as to remove the solvent, and the resultant residue was purified through silica gel column chromatography (hexane:ethyl acetate (v/v)=3:1) to thereby obtain 2-{3-[(2,2-dimethylpropionyl)isobutyl amino]-4-methoxyphenyl}-3-(4-nitrophenyl)propionic acid ethyl ester (yield: 399 mg, yield ratio: 101%) as a light yellow crystal containing a trace amount of solvent.

$^1$H-NMR (CDCl$_3$) δ value: 0.71-1.06 (15H, m), 1.15 (3H, t, J=7.1 Hz), 1.45-1.80 (1H, m), 2.50-2.75 (1H, m), 3.05-3.22 (1H, m), 3.73-3.88 (1H, m), 3.80 (3H, s), 3.94-4.17 (3H, m), 6.84 (1H, d, J=8.6 Hz), 7.08 (1H, br s), 7.16-7.34 (3H, m), 8.09 (2H, d, J=8.6 Hz).

FABMS: 485 (M+H)$^+$.

Thus obtained 2-{3-[(2,2-dimethylpropionyl)isobutyl amino]-4-methoxyphenyl}-3-(4-nitrophenyl)propionic acid ethyl ester (4.86 g, 10 mmol) and 10 wt % of palladium/carbon (450 mg) were dissolved in a mixed solvent of methanol (25 mL) and ethyl acetate (25 mL), and the solution was stirred under a hydrogen atmosphere (3 kg/cm$^2$) for 3 hours. The reaction solution was filtered through Celite so as to remove the palladium/carbon catalyst, concentrated under reduced pressure, evaporated under reduced pressure so as to remove the solvent, and the resultant residue was purified through silica gel column chromatography (hexane:ethyl acetate (v/v)=2:1) to thereby obtain 3-(4-aminophenyl)-2-{3-[(2,2-dimethylpropionyl) isobutylamino]-4-methoxyphenyl} propionic acid ethyl ester (yield: 4.35 g, yield ratio: 95%) as a syrup.

Thus obtained 3-(4-aminophenyl)-2-{3-[(2,2-dimethylpropionyl)isobutylamino]-4-methoxyphenyl} propionic acid ethyl ester (3.26 g, 7.18 mmol) was dissolved in chloroform (40 mL), and added with pyridine (0.81 mL, 10 mmol). The mixture was further added with 2,6-dichlorobenzoyl chloride (1.33 mL, 9.3 mmol), and stirred for 2 hours. The reaction solution was treated with a 1 mol/L hydrochloric acid (15 mL). The solution was extracted with chloroform, the extract was dried over anhydrous sodium sulfate, evaporated under reduced pressure so as to remove the solvent, and the resultant residue was purified through silica gel column chromatography (chloroform:ethyl acetate (v/v)=10:1). The eluate was further dissolved in a mixed solvent of chloroform (50 mL) and ethyl acetate (50 mL), added with hexane, allowed to crystallize, and the crystal was collected by filtration. The obtained crystal was dried in vacuo to thereby obtain 3-[4-(2,6-dichlorobenzoyl amino) phenyl]-2-{3-[(2,2-dimethylpropionyl)isobutyl amino]-4-methoxyphenyl}propionic acid ethyl ester (yield: 3.2 g, yield ratio: 71%) as a white solid.

Thus obtained 3-[4-(2,6-dichlorobenzoyl amino) phenyl]-2-{3-[(2,2-dimethylpropionyl)isobutylamino]-4-methoxyphenyl}propionic acid ethyl ester (415 mg, 0.66 mmol) was dissolved in a mixed solvent of methanol (6 mL) and tetrahydrofuran (6 mL), and added with a 2 mol/L aqueous sodium hydroxide solution (6 mL, 12 mmol). The solvent was evaporated under reduced pressure, the resultant residue was added with water to be dissolved, and the solution was washed with diethyl ether. The separated aqueous phase was added with a 1 mol/L hydrochloric acid so as to adjust pH of the solution to as low as 4 or below. The solution was extracted with ethyl acetate, dried over anhydrous sodium sulfate, evaporated under reduced pressure so as to remove the solvent to thereby obtain 3-[4-(2,6-dichlorobenzoyl amino) phenyl]-2-{3-[(2,2-dimethylpropionyl)isobutylamino]-4-methoxyphenyl}propionic acid (yield: 360 mg, yield ratio: 91%) as a light yellow solid.

Physical properties of the solid are shown in Table 3 below.

Example 39

Preparation of 3-[4-(3,5-dichloropyridine-4-carbonylamino)phenyl]-2-{3-[(2,2-dimethylpropionyl)isobutylamino]-4-methoxyphenyl}propionic acid

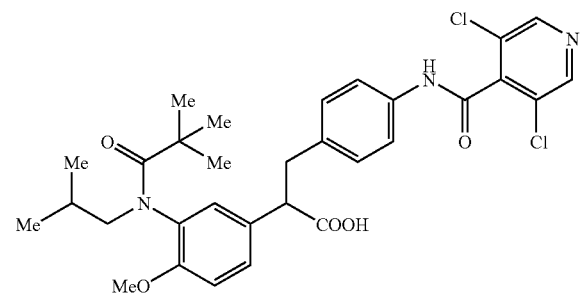

Diisopropylamine (31 mL, 221 mmol) was dissolved in tetrahydrofuran (200 mL), and the solution was added drop-wisely with a 1.6 mol/L hexane solution of n-butyl-lithium (128 mL, 205 mmol) at −78° C. The mixture was stirred for 15 minutes, and was added drop-wisely with a tetrahydrofuran solution (200 mL) of 3,5-dichloropyridine (25.1 g, 170 mmol) while keeping the temperature at −78° C., and then stirred for additional 1 hour. The reaction solution was added with dry ice to thereby gradually heat to room temperature, and further stirred for 15 hours. The mixture was treated with water (1 L), added with a 1 mol/L aqueous sodium hydroxide solution (100 mL), and washed with ether. The separated aqueous phase was adjusted to be acidic using a 6 mol/L hydrochloric acid, and the resultant precipitate was collected by filtration. The filtrate was extracted with ethyl acetate, the extract was dried over anhydrous sodium sulfate, evaporated under reduced pressure so as to remove the solvent, and the mixture of the resultant residue and the precipitate previously collected were re-crystallized from ethanol, which yielded 3,5-dichloropyridine-4-carboxylic acid (yield: 23 g, yield ratio: 70%) as a yellow crystal.

Thus obtained 3,5-dichloropyridine-4-carboxylic acid (384 mg, 2 mmol) was dispersed in 1,2-dichloroethane (30 mL) to prepare a slurry, added with thionyl chloride (0.44 mL, 5 mmol), further added with dimethylformamide (0.3 mL), and the mixture was refluxed under heating for 1 hour. The solvent was evaporated under reduced pressure to thereby obtain a crude product of 3,5-dichloropyridine-4-carbonylchloride. 3-(4-aminophenyl)-2-{3-[(2,2-dimethyl propionyl)isobutylamino]-4-methoxyphenyl}propionic acid ethyl ester (2.04 g, 4.5 mmol) obtained in Example 38 was then dissolved in 1,2-dichloroethane (30 mL), and added with pyridine (0.57 mL, 7 mmol). To the mixture, the 1, 2-dichloroethane solution (10 mL) of 3,5-dichloro pyridine-4-carbonylchloride obtained in the above was added, and the mixture was stirred for 1 hour. The reaction solution was treated with water (15 mL), extracted with chloroform, dried over anhydrous sodium sulfate, evaporated under reduced pressure so as to remove the solvent, and the resultant residue was purified through silica gel column chromatography (hexane:ethyl acetate (v/v)=3:2) to thereby obtain 3-[4-(3,5-dichloropyridine-4-carbonylamino) phenyl]-2-{3-[(2,2-dimethylpropionyl)isobutylamino]-4-methoxyphenyl}propionic acid ethyl ester (yield: 2.77 g, yield ratio: 98%).

Thus obtained 3-[4-(3,5-dichloropyridine-4-carbonylamino)phenyl]-2-{3-[(2,2-dimethylpropionyl) isobutylamino]-4-methoxyphenyl}propionic acid ethyl ester (400 mg, 0.64 mmol) was dissolved in a mixed solvent of methanol (5 mL) and tetrahydrofuran (5 mL), and added with a 2 mol/L aqueous sodium hydroxide solution (5 mL, 10 mmol). The solvent was evaporated under reduced pressure, the resultant residue was added with water to be dissolved, and the solution was washed with diethyl ether. The separated aqueous phase was added with a 1 mol/L hydrochloric acid so as to adjust pH of the solution to 5 to 7. The solution was then extracted with ethyl acetate, dried over anhydrous sodium sulfate, and evaporated under reduced pressure so as to remove the solvent to thereby obtain 3-[4-(3,5-dichloro pyridine-4-carbonylamino)phenyl]-2-{3-[(2,2-dimethyl propionyl)isobutylamino]-4-methoxyphenyl}propionic acid (yield: 353 mg, yield ratio: 92%) as a white solid.

Physical properties of the product were shown in Table 3 below.

Compounds of Examples 30 to 37 and Examples 40 to 91 were also prepared similarly to Examples 38 and 39. Physical properties of these compounds are shown in Tables 3 to 8.

TABLE 3

[Structure: dichloropyridine/pyridazine carboxamide linked via NH to para-phenyl, then CH2-CH(COOH)- to a 3-amino-4-methoxyphenyl group, where the 3-amino is N(R1)-C(=O)-R2]

| Example No. | R1 | R2 | Z | NMR, MS |
|---|---|---|---|---|
| 30 | sec-Bu (CH(Me)Et) | —Me | CH | $^1$H-NMR(DMSO-d$_6$)δ: 0.75-0.89(6H, m), 1.39-1.55(1H, m), 1.47&1.63(3H, s), 2.90-3.10(2H, m), 3.20-3.28(1H, m), 3.49-3.62(1H, m), 3.78(3H, s), 3.72-3.88(1H, m), 7.02-7.12(4H, m), 7.26-7.31(1H, m), 7.45-7.59(5H, m), 10.61(1H, d, J=4.0Hz), 12.41(1H, br s). FABMS: 557(M+H)$^+$. |
| 31 | sec-Bu | —Me | N | $^1$H-NMR(DMSO-d$_6$)δ: 0.74-0.88(6H, m), 1.34-1.57(1H, m), 1.47&1.62(3H, s), 2.89-3.10(2H, m), 3.20-3.28(1H, m), 3.52-3.61(1H, m), 3.78(3H, s), 3.72-3.89(1H, m), 7.00-7.14(4H, m), 7.25-7.32(1H, m), 7.44-7.49(2H, m), 8.79(2H, s), 10.81(1H, d, J=3.6Hz), 12.41(1H, br s). FABMS: 558(M+H)$^+$. |
| 32 | sec-Bu | —Et | CH | $^1$H-NMR(DMSO-d$_6$)δ: 0.75-0.89(9H, m), 1.39-1.96(3H, m), 2.87-3.05(2H, m), 3.19-3.27(1H, m), 3.57-3.65(1H, m), 3.77(3H, s), 3.83-3.89(1H, m), 7.00-7.12(4H, m), 7.25-7.33(1H, m), 7.45-7.58(5H, m), 10.62(1H, d, J=2.0Hz), 12.39(1H, br s). FABMS: 571(M+H)$^+$. |
| 33 | sec-Bu | —Et | N | $^1$H-NMR(DMSO-d$_6$)δ: 0.74-0.89(9H, m), 1.36-1.99(3H, m), 2.86-3.05(2H, m), 3.20-3.28(1H, m), 3.57-3.65(1H, m), 3.77(3H, s), 3.83-3.90(1H, m), 7.00-7.14(4H, m), 7.26-7.33(1H, m), 7.45-7.50(2H, m), 8.79(2H, s), 10.80(1H, s), 12.31(1H, br s). FABMS: 572(M+H)$^+$. |
| 34 | sec-Bu | iso-Pr (CH(Me)$_2$) | CH | $^1$H-NMR(DMSO-d$_6$)δ: 0.74-0.81(12H, m), 1.41-1.60(1H, m), 2.01-2.25(1H, m), 2.82-3.01(2H, m), 3.19-3.30(1H, m), 3.58-3.70(1H, m), 3.77(3H, s), 3.82-3.91(1H, m), 7.00-7.12(4H, m), 7.25-7.34(1H, m), 7.45-7.58(5H, m), 10.61(1H, s), 12.40(1H, br s). FABMS: 585(M+H)$^+$. |
| 35 | sec-Bu | iso-Pr | N | $^1$H-NMR(DMSO-d$_6$)δ: 0.74-0.91(12H, m), 1.40-1.58(1H, m), 1.96-2.25(1H, m), 2.82-3.02(2H, m), 3.21-3.28(1H, m), 3.58-3.70(1H, m), 3.77(3H, s), 3.84-3.91(1H, m), 7.00-7.14(4H, m), 7.26-7.34(1H, m), 7.45-7.50(2H, m), 8.78(2H, s), 10.80(1H, s), 12.40(1H, br s). FABMS: 586(M+H)$^+$. |
| 36 | sec-Bu | cyclobutylmethyl | CH | $^1$H-NMR(DMSO-d$_6$)δ: 0.74-0.85(6H, m), 1.37-1.66(6H, m), 1.91-2.61(2H, m), 2.77-3.02(2H, m), 3.21-3.28(1H, m), 3.64-3.77(1H, m), 3.75(3H, s), 3.84-3.91(1H, m), 6.97-7.14(4H, m), 7.25-7.40(1H, m), 7.42-7.58(5H, m), 10.62(1H, s), 12.39(1H, br s). FABMS: 597(M+H)$^+$. |
| 37 | sec-Bu | cyclobutylmethyl | N | $^1$H-NMR(DMSO-d$_6$)δ: 0.74-0.85(6H, m), 1.37-1.63(6H, m), 1.91-2.64(2H, m), 2.73-3.03(2H, m), 3.21-3.29(1H, m), 3.63-3.77(1H, m), 3.75(3H, s), 3.85-3.91(1H, m), 6.96-7.07(2H, m), 7.15(2H, d, J=7.9Hz), 7.25-7.33(1H, m), 7.50(2H, d, J=8.3Hz), 8.78(2H, s), 10.82(1H, s), 12.37(1H, br s). FABMS: 598(M+H)$^+$. |
| 38 | sec-Bu | neopentyl (CH$_2$C(Me)$_3$) | CH | $^1$H-NMR(DMSO-d$_6$)δ: 0.63-1.00(15H, m), 1.39-1.70(1H, m), 2.40-2.60(1H, m), 2.81-3.04(1H, m), 3.16-3.40(1H, m), 3.77(3H, s), 3.80-4.01(2H, m), 6.94-7.18(4H, m), 7.32(1H, m), 7.42-7.61(5H, m), 10.60(1H, s), 12.40(1H, s). FABMS: 599(M+H)$^+$. |

TABLE 3-continued

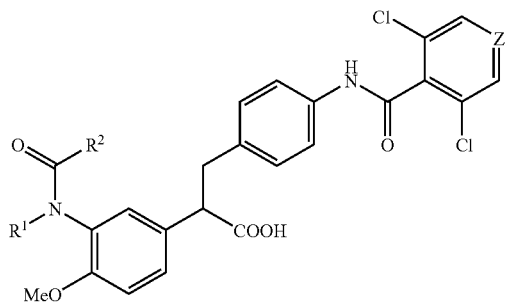

| Example No. | R¹ | R² | Z | NMR, MS |
|---|---|---|---|---|
| 39 | sec-Bu (Me-CH(Me)-CH2-... shown as Me/Me branched) | tBu (C(Me)3) | N | $^1$H-NMR(DMSO-$d_6$)δ: 0.60-1.00(15H, m), 1.35-1.68(1H, m), 2.39-2.59(1H, m), 2.78-3.07(1H, m), 3.14-3.43(1H, m), 3.68-4.00(2H, m), 3.77(3H, s), 6.90-7.21(4H, m), 7.22-7.56(3H, m), 8.79(2H, s), 10.81(1H, s), 12.43(1H, s). FABMS: 600(M+H)⁺. |
| 40 | sec-Bu | CH2-CH(Me)-CH2-Me | CH | $^1$H-NMR(DMSO-$d_6$)δ: 0.56-0.86(12H, m), 1.40-1.56(5H, m), 1.67-1.91(1H, m), 2.81-3.00(2H, m), 3.20-3.34(1H, m), 3.71-3.88(2H, m), 3.75(3H, s), 7.02-7.12(4H, m), 7.27-7.35(1H, m), 7.45-7.59(5H, m), 10.61(1H, s), 12.33(1H, br s). FABMS: 613(M+H)⁺. |
| 41 | sec-Bu | CH2-CH(Me)-CH2-Me | N | $^1$H-NMR(DMSO-$d_6$)δ: 0.56-0.86(12H, m), 1.03-1.60(5H, m), 1.63-1.91(1H, m), 2.80-3.01(2H, m), 3.19-3.29(1H, m), 3.71-3.89(2H, m), 3.75(3H, s), 6.91-7.15(4H, m), 7.27-7.36(1H, m), 7.45-7.51(2H, m), 8.73(2H, s), 10.81(1H, s), 12.41(1H, s). FABMS: 614(M+H)⁺. |
| 42 | —H | tBu | CH | $^1$H-NMR(CDCl$_3$)δ: 1.32(9H, s), 2.97-3.05(1H, m), 3.33-3.41(1H, m), 3.76-3.83(1H, m), 3.88(3H, m), 6.81(1H, d, J=8.3Hz), 7.17-7.20(1H, m), 7.19(2H, d, J=8.6Hz), 7.25-7.37(4H, m), 7.56(2H, d, J=8.3Hz), 8.11(1H, s), 8.47(1H, s), 9.27(1H, s). FABMS: 543(M+H)⁺. |
| 43 | —H | tBu | N | $^1$H-NMR(CDCl$_3$)δ: 1.27(9H, s), 2.88-2.95(1H, m), 3.32-3.40(1H, m), 3.73-3.77(1H, m), 3.88(3H, s), 6.82(1H, d, J=8.6Hz), 7.03-7.08(1H, m), 7.16(2H, d, J=8.6Hz), 7.53(2H, d, J=8.3Hz), 8.11(1H, s), 8.41(2H, s), 8.46(1H, s), 8.69(1H, s). FABMS: 544(M+H)⁺. |
| 44 | —H | CH2-CH(Me)-CH2-Me | CH | $^1$H-NMR(CDCl$_3$)δ: 0.96(6H, t, J=7.3Hz), 1.51-1.80(4H, m), 2.06-2.15(1H, m), 2.97-3.05(1H, m), 3.32-3.41(1H, m), 3.77-3.83(1H, m), 3.88(3H, m), 6.83(1H, d, J=8.6Hz), 7.05-7.08(1H, m), 7.20(2H, d, J=8.6Hz), 7.25-7.42(4H, m), 7.57(2H, d, J=8.3Hz), 7.80(1H, s), 8.47(1H, s), 9.50(1H, s). FABMS. 557(M+H)⁺. |
| 45 | —H | CH(Me)-Cl | CH | $^1$H-NMR(CDCl$_3$)δ: 1.82(3H, d, J=7.3Hz), 2.57-2.59(1H, m), 2.92-3.06(1H, m), 3.29-3.42(1H, m), 3.78-3.85(1H, m), 3.90(3H, s), 6.84(1H, d, J=8.3Hz), 7.07-7.37(7H, m), 7.57(2H, d, J=8.6Hz), 8.39(1H, s), 8.91(1H, s), 9.32(1H, s). FABMS: 549(M+H)⁺. |

TABLE 4

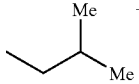

| Example No. | R¹ | R⁸ | R⁹ | NMR, MS |
|---|---|---|---|---|
| 46 | sec-Bu (Me-CH-CH₂-Me / Me) | —Cl | —Me | $^1$H-NMR(DMSO-d$_6$)δ: 0.60-0.98(15H, m), 1.34-1.70(1H, m), 2.28(3H, s), 2.40-2.61(1H, m), 2.78-3.02(1H, m), 3.13-3.48(1H, m), 3.77(3H, s), 3.78-3.99(2H, m), 6.95-7.16(4H, m), 7.20-7.39(4H, m), 7.44-7.60(2H, m), 10.43(1H, s), 12.40(1H, s). FABMS: 579(M+H)$^+$. |
| 47 | sec-Bu | —Me | —Me | $^1$H-NMR(CDCl$_3$)δ: 0.70-1.02(15H, m), 1.50-1.79(1H, m), 2.32(6H, s), 2.55-2.73(1H, m), 2.90-3.08(1H, m), 3.32-3.46(1H, m), 3.68-3.85(1H, m), 3.80(3H, s), 3.87-4.18(1H, m), 6.86(1H, d, J=8.6Hz), 7.02(2H, d, J=8.0Hz), 7.05-7.35(4H, m), 7.45-7.62(3H, m). FABMS: 559(M+H)$^+$. |
| 48 | sec-Bu | —F | —F | $^1$H-NMR(DMSO-d$_6$)δ: 0.73-0.89(15H, m), 1.31-1.65(1H, m), 2.41-2.57(1H, m), 2.85-3.02(1H, m), 3.20-3.28(1H, m), 3.77(3H, s), 3.82-3.99(2H, m), 7.02(2H, d, J=8.6Hz), 7.08-7.12(2H, m), 7.20-7.30(1H, m), 7.25(2H, d, J=7.9Hz), 7.49-7.63(3H, m), 10.67(1H, s), 12.40(1H, s). FABMS: 567(M+H)$^+$. |
| 49 | sec-Bu | —OMe | —OMe | $^1$H-NMR(CDCl$_3$)δ: 0.74-1.04(15H, m), 1.47-1.80(1H, m), 2.63(1H, m), 3.01(1H, m), 3.37(1H, dd, J=7.1, 13.7Hz), 3.59-3.87(1H, m), 3.79(3H, s), 3.80(6H, s), 4.02(1H, m), 6.57(2H, d, J=8.6Hz), 6.84(1H, d, J=8.6Hz), 6.98-7.12(3H, m), 7.22-7.33(1H, m), 7.43-7.58(3H, m). FABMS: 591(M+H)$^+$. |
| 50 | —H | —OMe | —OMe | $^1$H-NMR(CDCl$_3$)δ: 1.30(9H, s), 2.96-3.04(1H, m), 3.30-3.39(1H, m), 3.70-3.86(1H, m), 3.76(6H, s), 3.86(3H, s), 6.52(2H, d, J=8.6Hz), 6.79(1H, d, J=8.3Hz), 7.22-7.28(1H, m), 7.50(2H, d, J=8.3Hz), 7.66(1H, s), 8.10(1H, s), 8.46(1H, s). FABMS: 535 (M+H)$^+$. |

TABLE 5

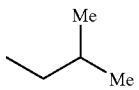

| Example No. | R¹ | R² | Z | NMR, MS |
|---|---|---|---|---|
| 51 | sec-Bu | —Me | CH | $^1$H-NMR(DMSO-d$_6$)δ: 0.77(3H, d, J=6.3Hz), 0.82(3H, d, J=6.9Hz), 1.28(3H, t, J=6.8Hz), 1.40-1.42(1H, m), 1.48&1.64(3H, m), 2.91-2.98(1H, m), 3.06-3.13(1H, m), 3.17-3.27(2H, m), 3.83(1H, t, J=7.8Hz), 4.05(2H, d, J=5.9Hz), 7.03-7.11(4H, m), 7.25(1H, t, J=6.4Hz), 7.47-7.58(5H, m), 10.62(1H, s), 12.39(1H, br s). FABMS: 571(M+H)$^+$. |

TABLE 5-continued

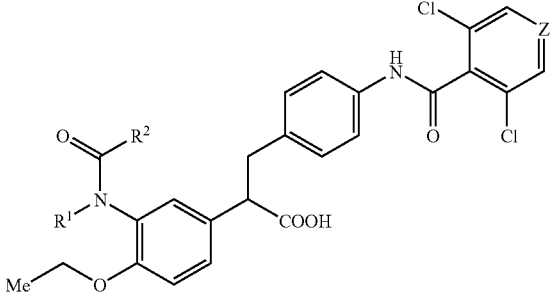

| Example No. | R¹ | R² | Z | NMR, MS |
|---|---|---|---|---|
| 52 | 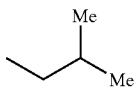 | —Me | N | ¹H-NMR(DMSO-d₆)δ: 0.75-0.84(6H, m), 1.28(3H, t, J=6.9Hz), 1.36-1.54(1H, m), 1.48&1.63(3H, s), 2.89-3.05(1H, m), 3.08-3.17(1H, m), 3.20-3.28(2H, m), 3.84(1H, t, J=7.3Hz), 4.05(2H, d, J=6.9Hz), 7.02-7.14(4H, m), 7.26(1H, t, J=6.3Hz), 7.44-7.49(2H, m), 8.79(2H, s), 10.81(1H, s), 12.50(1H, br s). FABMS: 572(M+H)⁺. |
| 53 | 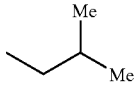 | —Et | CH | ¹H-NMR(DMSO-d₆)δ: 0.69-0.90(9H, m), 1.24-1.29(3H, m), 1.63-1.70(2H, m), 1.08&1.35(1H, t, J=7.1Hz), 1.41-1.58(1H, m), 1.82-2.09(1H, m), 2.90-3.11(2H, m), 3.17-3.26(2H, m), 3.84(1H, t, J=7.3Hz), 4.04(2H, d, J=6.3Hz), 6.95-7.12(4H, m), 7.16-7.34(2H, m), 7.45-7.59(4H, m), 10.61(1H, s), 12.44(1H, br s). FABMS: 585(M+H)⁺. |
| 54 | 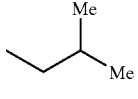 | —Et | N | ¹H-NMR(DMSO-d₆)δ: 0.75-0.89(6H, m), 1.02-1.10(3H, m), 1.26(3H, t, J=6.3Hz), 1.35(1H, t, J=6.6Hz), 1.61-1.69(1H, m), 2.25(1H, q, J=7.6Hz), 2.92-3.17(2H, m), 3.19-3.22(2H, m), 3.76-3.85(1H, m), 4.03(2H, d, J=6.6Hz), 6.98-7.14(4H, m), 7.19-7.29(1H, m), 7.38-7.52(2H, m), 8.79(2H, s), 10.81(1H, s), 12.40(1H, br s). FABMS: 586(M+H)⁺. |
| 55 | 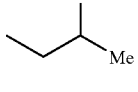 |  | CH | ¹H-NMR(DMSO-d₆)δ: 0.73-0.90(12H, m), 1.26(3H, t, J=6.6Hz), 1.42-1.57(1H, m), 2.02-2.23(1H, m), 2.88-3.07(1H, m), 3.09-3.26(2H, m), 3.45-3.56(1H, m), 3.83(1H, br s), 4.03(2H, q, J=6.6Hz), 7.02-7.12(4H, m), 7.26(1H, t, J=8.9Hz), 7.47-7.58(5H, m), 10.61(1H, s), 12.39(1H, br s). FABMS: 599(M+H)⁺. |
| 56 | 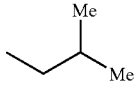 |  | N | ¹H-NMR(DMSO-d₆)δ: 0.72-0.89(12H, m), 1.26(3H, t, J=6.9Hz), 1.40-1.57(1H, m), 2.03&2.20(1H, t, J=6.6Hz), 2.89-3.09(1H, m), 3.11-3.25(2H, m), 3.45-3.56(1H, m), 3.82-3.89(1H, m), 4.03(2H, q, J=6.9Hz), 7.01-7.15(4H, m), 7.23(1H, d, J=8.3Hz), 7.28(1H, d, J=8.9Hz), 7.46(1H, d, J=8.6Hz), 7.48(1H, d, J=8.3Hz), 8.78(2H, s), 10.81(1H, s), 12.37(1H, br s). FABMS: 600(M+H)⁺. |
| 57 | 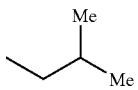 |  | CH | ¹H-NMR(CDCl₃)δ: 0.80(3H, d, J=6.9Hz), 0.85(3H, s), 0.86(3H, s), 0.89(3H, d, J=6.9Hz), 0.97(3H, s), 1.38(3H, t, J=6.9Hz), 1.70-1.80(1H, m), 2.75-2.82(1H, m), 2.98-3.05(1H, m), 3.33-3.44(1H, m), 3.76-3.79(1H, m), 3.82-3.96(1H, m), 4.01(2H, t, J=6.9Hz), 6.83(1H, d, J=8.6Hz), 7.08(1H, d, J=6.3Hz), 7.13-7.20(2H, m), 7.23(2H, d, J=5.3Hz), 7.28(2H, d, J=5.3Hz), 7.54(2H, t, J=7.6Hz), 7.98(1H, br s). FABMS: 613(M+H)⁺. |
| 58 | 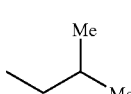 |  | N | ¹H-NMR(DMSO-d₆)δ: 0.75(6H, s), 0.82(6H, dd, J=6.6, 13.5Hz), 0.90(3H, s), 1.28(3H, t, J=6.9Hz), 1.46-1.74(1H, m), 2.57-2.68(1H, m), 2.92-3.01(1H, m), 3.17-3.27(1H, m), 3.78-3.88(2H, m), 3.99-4.06(2H, m), 7.00(2H, d, J=8.6Hz), 7.11-7.16(2H, m), 7.25-7.31(1H, m), 7.44-7.51(2H, m), 8.78(2H, s), 10.80(1H, s), 12.40(1H, br s). FABMS: 614(M+H)⁺. |

TABLE 5-continued

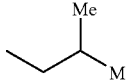

| Example No. | R¹ | R² | Z | NMR, MS |
|---|---|---|---|---|
| 59 | 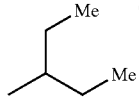 sec-Bu | 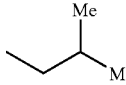 isobutyl | CH | ¹H-NMR(CDCl₃)δ: 0.61(3H, t, J=7.3Hz), 0.70(3H, dd, J=7.3, 14.8Hz), 0.81(3H, dd, J=7.4, 17.0Hz), 0.88(3H, dd, J=6.6, 11.2Hz), 1.19-1.31(2H, m), 1.37(3H, t, J=6.9Hz), 1.43-1.71(3H, m), 1.74-1.93(1H, m), 2.92-3.04(1H, m), 3.12(1H, dd, J=6.6, 13.4Hz), 3.32-3.40(1H, m), 3.65-3.81(2H, m), 3.95-4.06(2H, m), 6.88(1H, d, J=8.6Hz), 7.03-7.21(3H, m), 7.23-7.32(4H, m), 7.54(1H, d, J=5.9Hz), 7.57(1H, d, J=5.9Hz), 8.09(1H, br s). FABMS: 627(M+H)⁺. |
| 60 | 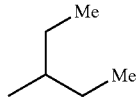 sec-Bu | 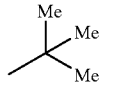 isobutyl | N | ¹H-NMR(DMSO-d₆)δ: 0.55-0.85(12H, m), 1.08-1.16(2H, m), 1.27(3H, t, J=6.8Hz), 1.34-1.46(2H, m), 1.53-1.55(1H, m), 1.70&1.88(1H, br s), 2.92-3.04(2H, m), 3.21-3.26(1H, m), 3.62-3.84(2H, m), 3.97-4.05(2H, m), 6.93(1H, s), 7.00-7.15(3H, m), 7.26-7.32(1H, m), 7.46(1H, d, J=7.9Hz), 7.49(1H, d, J=7.9Hz), 8.79(2H, s), 10.82(1H, s), 12.40(1H, br s). FABMS: 628(M+H)⁺. |
| 61 | —Et | 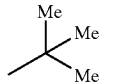 t-Bu | CH | ¹H-NMR(DMSO-d₆)δ: 0.74(6H, s), 0.90(6H, s), 1.28(3H, t, J=6.9Hz), 2.94(2H, brs), 3.19-3.27(1H, m), 3.80-3.83(2H, m), 4.04(2H, d, J=4.3Hz), 7.01(2H, d, J=8.6Hz), 7.12(2H, brs), 7.29(1H, brs), 7.46-7.59(5H, m), 10.62(1H, s). FABMS: 585(M+H)⁺. |
| 62 | —Et | 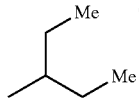 t-Bu | N | ¹H-NMR(DMSO-d₆)δ: 0.74(3H, s), 0.90(9H, d, J=6.6Hz), 1.28(3H, t, J=6.9Hz), 2.91-3.01(2H, m), 3.20-3.28(1H, m), 3.73-3.86(2H, m), 3.95-4.04(2H, m), 6.75-6.96(1H, m), 7.02(1H, d, J=8.6Hz), 7.14(2H, s), 7.29(1H, brs), 7.49(2H, d, J=8.3Hz), 8.79(2H, s), 10.81(1H, s), 12.34(1H, brs). FABMS: 586(M+H)⁺. |
| 63 | —Et | 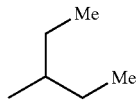 isobutyl | CH | ¹H-NMR(DMSO-d₆)δ: 0.53-0.76(6H, m), 0.87-0.98(3H, m), 1.04-1.21(2H, m), 1.27(3H, t, J=6.9Hz), 1.32-1.49(2H, m), 1.67&1.84(1H, q, J=6.6Hz), 2.84-2.98(1H, m), 3.12-3.28(2H, m), 3.71-3.92(2H, m), 3.96-4.08(2H, m), 6.95(1H, dd, J=2.0, 22.3Hz), 7.04-7.13(3H, m), 7.30(1H, t, J=9.7Hz), 7.43-7.58(5H, m), 10.62&10.64(1H, s), 12.36-12.44(1H, m). FABMS: 599(M+H)⁺. |
| 64 | —Et | 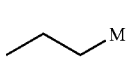 isobutyl | N | ¹H-NMR(DMSO-d₆)δ: 0.52-0.76(6H, m), 0.87-0.98(3H, m), 1.11-1.17(2H, m), 1.27(3H, t, J=6.8Hz), 1.34-1.44(2H, m), 1.67-1.85(1H, m), 2.91-2.99(1H, m), 3.14-3.28(2H, m), 3.74-3.89(2H, m), 3.96-4.07(2H, m), 6.94(1H, dd, J=1.7, 24.1Hz), 7.04-7.10(2H, m), 7.14(1H, d, J=8.6Hz), 7.30(1H, t, J=9.9Hz), 7.48(2H, t, J=7.9Hz), 8.79(2H, s), 10.81&10.83(1H, s), 12.35(1H, brs). FABMS: 600(M+H)⁺. |
| 65 | 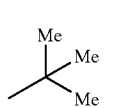 n-Bu | 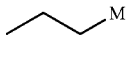 t-Bu | CH | ¹H-NMR(DMSO-d₆) δ: 0.74(9H, s), 0.90(3H, s), 1.23-1.34(4H, m), 2.85-3.00(2H, m), 3.17-3.26(2H, m), 4.02(2H, brs), 7.00(2H, d, J=8.6Hz), 7.11(2H, brs), 7.28(1H, brs), 7.45-7.59(5H, m), 10.61(1H, s), 12.35(1H, brs). FABMS: 599(M+H)⁺. |
| 66 | 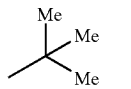 n-Bu |  t-Bu | N | ¹H-NMR(DMSO-d₆)δ: 0.74(9H, s), 0.89(3H, s), 1.23-1.34(5H, m), 2.81-3.00(2H, m), 3.20-3.27(1H, m), 3.77-3.84(2H, m), 4.03(2H, t, J=6.3Hz), 6.96-7.02(2H, m), 7.14(2H, s), 7.28(1H, s), 7.47(2H, s), 8.79(2H, s), 10.80(1H, s), 12.33(1H, brs). FABMS: 600(M+H)⁺. |

TABLE 5-continued

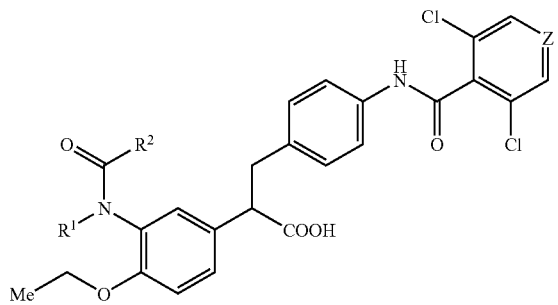

| Example No. | R¹ | R² | Z | NMR, MS |
|---|---|---|---|---|
| 67 | propyl-Me | isobutyl-Me(Me) | CH | $^1$H-NMR(DMSO-d$_6$)δ: 0.54-0.88(9H, m), 1.12-1.17(2H, m), 1.27(3H, t, J=6.9Hz), 1.34-1.39(2H, m), 1.70-1.90(2H, m), 2.90-2.98(2H, m), 3.12-3.25(2H, m), 3.71-3.83(2H, m), 3.98-4.04(2H, m), 6.95(1H, dd, J=2.1, 23.6Hz), 7.05(2H, d, J=8.6Hz), 7.11(1H, d, J=8.6Hz), 7.29(1H, t, J=9.4Hz), 7.45-7.58(5H, m), 10.61&10.63(1H, s). FABMS: 613(M+H)⁺. |
| 68 | propyl-Me | isobutyl-Me(Me) | N | $^1$H-NMR(DMSO-d$_6$)δ: 0.53-0.88(9H, m), 1.08-1.20(2H, m), 1.27(3H, t, J=6.9Hz), 1.34-1.41(4H, m), 1.66-1.87(1H, m), 2.91-2.99(1H, m), 3.07-3.12(1H, m), 3.18-3.28(1H, m), 3.71-3.87(2H, m), 3.95-4.07(2H, m), 6.94(1H, dd, J=2.1, 24.9Hz), 7.04-7.15(3H, m), 7.26-7.34(1H, m), 7.48(2H, t, J=8.1Hz), 8.78(1H, s), 8.79(1H, s), 10.80&10.82(1H, s). FABMS: 614(M+H)⁺. |

TABLE 6

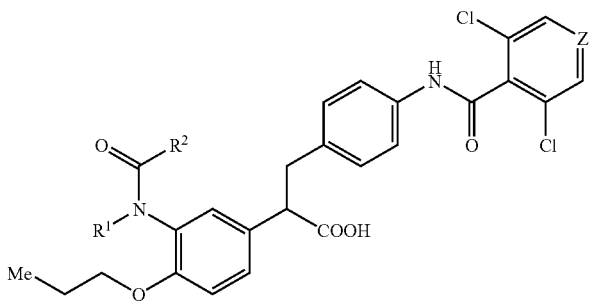

| Example No. | R¹ | R² | Z | NMR, MS |
|---|---|---|---|---|
| 69 | sec-butyl (Me, Me) | —Me | CH | $^1$H-NMR(DMSO-d$_6$) δ: 0.77-0.83(6H, m), 0.94(3H, t, J=7.3 Hz), 1.41-1.56(1H, m), 1.48&1.63(3H, s), 1.67-1.72(2H, m), 2.88-3.08(2H, m), 3.14-3.27(2H, m), 3.84(1H, t, J=7.6 Hz), 3.93(2H, br s), 7.03-7.12(4H, m), 7.25(1H, t, J=6.3 Hz), 7.48-7.58(5H, m), 10.62(1H, s), 12.38(1H, br s). FABMS: 585 (M + H)⁺. |
| 70 | sec-butyl (Me, Me) | —Me | N | $^1$H-NMR(DMSO-d$_6$) δ: 0.75-0.83(6H, m), 0.94(3H, t, J=7.3 Hz), 1.48&1.63(3H, s), 1.40-1.56(1H, m), 1.64-1.75(2H, m), 2.88-3.08(2H, m), 3.14-3.23(1H, m), 3.45-3.53(1H, m), 3.84(1H, t, J=7.9 Hz), 3.94(2H, t, J=6.1 Hz), 7.02-7.13(4H, m), 7.26(1H, t, J=6.4 Hz), 7.44-7.49(2H, m), 8.79(2H, s), 10.81(1H, s), 12.39(1H, br s). FABMS: 586 (M + H)⁺. |
| 71 | sec-butyl (Me, Me) | —Et | CH | $^1$H-NMR(DMSO-d$_6$) δ: 0.77-0.86(9H, m), 0.92(3H, t, J=7.3 Hz), 1.42-1.60(2H, m), 1.63-1.70(2H, m), 1.75-1.95(1H, m), 2.90-3.09(1H, m), 3.12-3.27(1H, m), 3.50-3.58(1H, m), 3.81-3.90(1H, m), 3.92-3.94(2H, m), 6.96-7.12(4H, m), 7.23-7.29(1H, m), 7.45-7.58(5H, m), 10.61(1H, s), 12.33(1H, br s). FABMS: 599 (M + H)⁺. |

TABLE 6-continued

[Structure: core scaffold with R¹, R² on carbamoyl group, propoxy (Me-CH₂-CH₂-O-), CH₂ linker to phenyl-CH(COOH), anilide to 2,6-dichloropyridyl/phenyl (Z = N or CH)]

| Example No. | R¹ | R² | Z | NMR, MS |
|---|---|---|---|---|
| 72 | sec-Bu (Me-CH(Me)-CH₂-Me) | —Et | N | ¹H-NMR(DMSO-d₆) δ: 0.76-0.95(9H, m), 1.65(3H, t, J=6.9 Hz), 1.75-1.94(1H, m), 2.25(1H, q, J=7.6 Hz), 2.91-3.04(2H, m), 3.09-3.27(2H, m), 3.49-3.57(2H, m), 3.76-3.85(2H, m), 3.88-3.94(2H, m), 6.85-7.14(4H, m), 7.24-7.29(1H, m), 7.38-7.48(2H, m), 8.79(2H, s), 10.81(1H, s), 12.41(1H, br s). FABMS: 600 (M + H)⁺. |
| 73 | sec-Bu | iBu (CH₂CH(Me)₂) | CH | ¹H-NMR(DMSO-d₆) δ: 0.73-0.96(12H, m), 1.43-1.57(1H, m), 1.67(3H, dd, J=6.6, 13.5 Hz), 2.01-2.23(1H, m), 2.88-3.08(2H, m), 3.21-3.26(2H, m), 3.53-3.60(2H, m), 3.86(1H, br s), 3.92(2H, t, J=6.1 Hz), 7.03-7.12(4H, m), 7.26(1H, t, J=9.2 Hz), 7.48-7.57(5H, m), 10.61(1H, s), 12.45(1H, br s). FABMS: 613 (M + H)⁺. |
| 74 | sec-Bu | iBu | N | ¹H-NMR(DMSO-d₆) δ: 0.76-1.06(15H, m), 1.42-1.59(1H, m), 1.61-1.74(2H, m), 2.00-2.23(1H, m), 2.91-3.08(2H, m), 3.17-3.23(1H, m), 3.53-3.63(1H, m), 3.83-3.85(1H, m), 3.92(2H, t, J=6.1 Hz), 7.02-7.15(4H, m), 7.24-7.31(1H, m), 7.47(1H, d, J=7.9 Hz), 7.48(1H, d, J=7.6 Hz), 8.79(2H, s), 10.81(1H, s), 12.45(1H, br s). FABMS: 614 (M + H)⁺. |
| 75 | sec-Bu | tBu (C(Me)₃) | CH | ¹H-NMR(CDCl₃) δ: 0.79(3H, d, J=6.6 Hz), 0.84(3H, s), 0.88(3H, d, J=6.3 Hz), 0.91(3H, s), 0.96(3H, s), 1.01(3H, t, J=7.3 Hz), 1.64-1.72(1H, m), 1.78(2H, q, J=6.9 Hz), 2.72(1H, dd, J=6.3, 12.9 Hz), 2.93-3.06(1H, m), 3.33-3.44(1H, m), 3.79(2H, t, J=7.3 Hz), 3.86-4.02(2H, m), 6.83(1H, d, J=8.6 Hz), 7.07-7.20(3H, m), 7.25(2H, d, J=5.6 Hz), 7.29(2H, d, J=5.6 Hz), 7.54(2H, t, J=8.2 Hz), 7.86&7.93(1H, br s). FABMS: 627 (M + H)⁺. |
| 76 | sec-Bu | tBu | N | ¹H-NMR(DMSO-d₆) δ: 0.73(6H, s), 0.82(3H, dd, J=6.6, 14.2 Hz), 0.89(3H, br s), 0.92-0.97(3H, m), 1.47(1H, br s), 1.62-1.72(3H, m), 2.56-2.63(1H, m), 2.84-3.01(1H, m), 3.04-3.27(3H, m), 3.87(2H, br s), 3.92-3.94(2H, m), 6.99(2H, d, J=8.6 Hz), 7.11-7.32(3H, m), 7.43-7.51(2H, m), 8.79(2H, s), 10.81(1H, s), 12.37(1H, br s). FABMS: 628 (M + H)⁺. |
| 77 | sec-Bu | CH₂CH(Me)CH₂Me | CH | ¹H-NMR(CDCl₃) δ: 0.59-0.72(6H, m), 0.75-0.84(3H, m), 0.88(3H, dd, J=6.6, 11.9 Hz), 1.00(3H, t, J=7.3 Hz), 1.15-1.39(2H, m), 1.43-1.60(2H, m), 1.62-1.70(1H, m), 1.77(2H, q, J=6.6 Hz), 1.92(1H, t, J=6.3 Hz), 2.93-3.06(2H, m), 3.32-3.43(1H, m), 3.75-3.84(2H, m), 3.89(2H, t, J=6.6 Hz), 6.89(1H, d, J=6.6 Hz), 7.03-7.13(2H, m), 7.18(1H, d, J=8.3 Hz), 7.20-7.32(4H, m), 7.54(1H, d, J=8.6 Hz), 7.56(1H, d, J=8.3 Hz), 8.05(1H, s). FABMS: 641 (M + H)⁺. |
| 78 | sec-Bu | CH₂CH(Me)CH₂Me | N | ¹H-NMR(DMSO-d₆) δ: 0.56-0.65(3H, m), 0.74-0.86(6H, m), 0.94(3H, t, J=7.3 Hz), 1.04-1.26(2H, m), 1.28-1.38(2H, m), 1.40-1.45(1H, m), 1.48-1.59(1H, m), 1.68(3H, dd, J=6.6, 13.9 Hz), 2.83-3.00(2H, m), 3.17-3.28(3H, m), 3.78-3.85(2H, m), 3.91(2H, t, J=6.3 Hz), 6.90(1H, s), 6.99-7.12(3H, m), 7.25-7.32(1H, m), 7.48(2H, t, J=7.9 Hz), 8.78(1H, s), 8.79(1H, s), 10.81(1H, s), 12.40(1H, br s). FABMS: 642 (M + H)⁺. |
| 79 | —Et | tBu | CH | ¹H-NMR(DMSO-d₆) δ: 0.74(3H, s), 0.82-0.98(12H, m), 1.18-1.29(1H, m), 1.70(2H, q, J=6.6 Hz), 2.94(1H, brs), 3.22(1H, m), 3.83-3.91(4H, m), 7.00(2H, d, J=8.6 Hz), 7.11(2H, s), 7.29(1H, brs), 7.48-7.57(5H, m), 10.60(1H, s), 12.35(1H, brs). FABMS: 599 (M + H)⁺. |

TABLE 6-continued

[Structure: A compound with a central propanoic acid (COOH) bearing two aryl groups. One aryl is a phenyl substituted at para with -OCH₂CH₂CH₃ (propoxy, shown as Me with propyl chain -O) and at meta with -N(R¹)-C(=O)-R². The other aryl is a 4-aminophenyl linked via -NH-C(=O)- to a 2,6-dichloropyridine/benzene (Z = N or CH).]

| Example No. | R¹ | R² | Z | NMR, MS |
|---|---|---|---|---|
| 80 | —Et | -C(Me)(Me)Me (t-Bu) | N | ¹H-NMR(DMSO-d₆) δ: 0.73(6H, s), 0.89(6H, s), 0.95(3H, t, J=7.3 Hz), 1.69(2H, q, J=6.4 Hz), 2.94(2H, brs), 3.20-3.25(1H, m), 3.84-3.93(4H, m), 7.00(2H, d, J=8.3 Hz), 7.14(2H, s), 7.29(1H, brs), 7.47(2H, s), 8.79(2H, s), 10.80(1H, s), 12.33(1H, brs). FABMS: 600 (M + H)⁺. |
| 81 | —Et | -CH(Me)CH₂CH(Me)Me (isopentyl-like) | CH | ¹H-NMR(DMSO-d₆) δ: 0.57-0.77(6H, m), 0.83-0.95(6H, m), 1.07-1.41(4H, m), 1.64-1.69(2H, m), 1.80-1.91(1H, m), 2.90-2.93(1H, m), 3.11-3.26(2H, m), 3.78-3.91(4H, m), 6.90-7.13(3H, m), 7.20-7.33(1H, m), 7.48-7.55(6H, m), 10.61(1H, s), 12.38(1H, brs). FABMS: 613 (M + H)⁺. |
| 82 | —Et | -CH(Me)CH₂CH(Me)Me | N | ¹H-NMR(DMSO-d₆) δ: 0.53-0.77(6H, m), 0.87-0.97(6H, m), 1.23-1.40(4H, m), 1.67(2H, q, J=6.6 Hz), 1.87-1.91(1H, m), 2.81-3.04(1H, m), 3.11-3.26(2H, m), 3.79-3.86(2H, m), 3.91(2H, t, J=6.6 Hz), 6.94(1H, dd, J=2.1, 27.5 Hz), 7.08(2H, d, J=7.9 Hz), 7.14(1H, d, J=8.6 Hz), 7.26-7.34(1H, m), 7.45(2H, t, J=7.9 Hz), 8.79(2H, s), 10.81&10.83(1H, s), 12.38(1H, brs). FABMS: 614 (M + H)⁺. |
| 83 | -CH₂CH₂CH₂Me (n-Bu) | -C(Me)(Me)Me (t-Bu) | CH | ¹H-NMR(DMSO-d₆) δ: 0.74-0.98(15H, m), 1.35(1H, m), 1.69(2H, q, J=6.9 Hz), 2.80-2.95(2H, m), 3.21-3.24(2H, m), 3.84-3.93(4H, m), 7.00(2H, d, J=8.6 Hz), 7.11(2H, brs), 7.28(1H, brs), 7.45-7.59(5H, m), 10.60(1H, s), 12.30(1H, brs). FABMS: 613 (M + H)⁺. |
| 84 | -CH₂CH₂CH₂Me | -C(Me)(Me)Me | N | ¹H-NMR(DMSO-d₆) δ: 0.73-0.98(15H, m), 1.29-1.35(1H, m), 1.69(2H, q, J=6.6 Hz), 2.79-2.96(2H, m), 3.20-3.25(2H, m), 3.78-3.96(4H, m), 7.00(2H, d, J=8.9 Hz), 7.13(2H, d, J=8.6 Hz), 7.29(1H, t, J=8.7 Hz), 7.45(2H, d, J=8.3 Hz), 8.79(2H, s), 10.80(1H, s), 12.35(1H, brs). FABMS: 614 (M + H)⁺. |
| 85 | -CH₂CH₂CH₂Me | -CH(Me)CH₂CH(Me)Me | CH | ¹H-NMR(DMSO-d₆) δ: 0.54-0.88(9H, m), 0.94(3H, t, J=7.4 Hz), 1.06-1.20(2H, m), 1.21-1.49(4H, m), 1.67(2H, q, J=6.8 Hz), 1.77-1.91(1H, m), 2.85-3.09(2H, m), 3.18-3.27(1H, m), 3.75-3.93(4H, m), 6.87-7.13(4H, m), 7.21-7.33(1H, m), 7.42-7.59(5H, m), 10.62&10.63(1H, s). FABMS: 627 (M + H)⁺. |
| 86 | -CH₂CH₂CH₂Me | -CH(Me)CH₂CH(Me)Me | N | ¹H-NMR(DMSO-d₆) δ: 0.54-0.87(9H, m), 0.94(3H, t, J=7.3 Hz), 1.05-1.20(2H, m), 1.23-1.46(4H, m), 1.67(2H, q, J=6.8 Hz), 1.74-1.91(1H, m), 2.91-3.04(2H, m), 3.18-3.28(1H, m), 3.76-3.93(4H, m), 6.93(1H, dd, J=1.7, 30.5 Hz), 7.08(2H, dd, J=1.8, 6.4 Hz), 7.14(1H, d, J=8.3 Hz), 7.25-7.34(1H, m), 7.48(2H, t, J=8.1 Hz), 8.78(1H, s), 8.79(1H, s), 10.81&10.82(1H, s). FABMS: 628 (M + H)⁺. |

TABLE 7

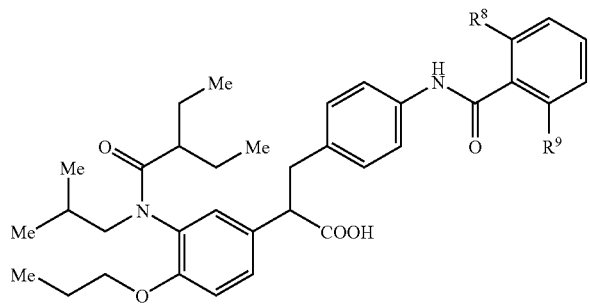

| Example No. | R⁸ | R⁹ | NMR, MS |
|---|---|---|---|
| 87 | —Cl | —F | $^1$H-NMR(DMSO-$d_6$) δ: 0.55-0.65(3H, m), 0.73-0.86(9H, m), 0.94(3H, t, J=7.4 Hz), 1.04-1.92(8H, m), 2.81-2.99(2H, m), 3.18-3.28(1H, m), 3.72-3.93(4H, m), 6.89-7.11(4H, m), 7.23-7.58(6H, m), 10.66(1H, s), 12.39(1H, br s). FABMS: 625 (M + H)⁺. |
| 88 | —F | —F | $^1$H-NMR(DMSO-$d_6$) δ: 0.54-0.65(3H, m), 0.73-0.85(9H, m), 0.94(3H, t, J=7.4 Hz), 1.03-1.90(8H, m), 2.81-2.99(2H, m), 3.20-3.28(1H, m), 3.71-3.93(4H, m), 6.88-7.10(2H, m), 7.04(2H, d, J=8.6 Hz), 7.20-7.31(1H, m), 7.25(2H, d, J=8.3 Hz), 7.48-7.63(3H, m), 10.67(1H, s), 12.40(1H, br s). FABMS: 609 (M + H)⁺. |

TABLE 8

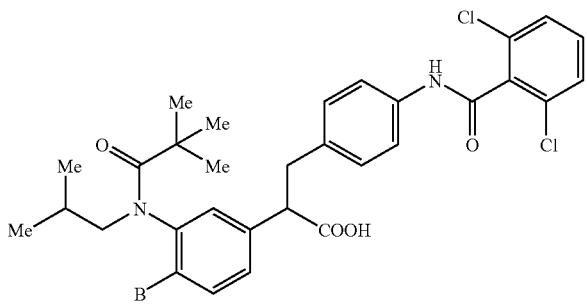

| Example No. | B | NMR, MS |
|---|---|---|
| 89 | —OH | $^1$H-NMR(CDCl$_3$) δ: 0.89(6H, d, J=6.6 Hz), 1.32(9H, s), 1.79(1H, m), 2.78-2.94(3H, m), 3.21(1H, dd, J=8.6, 13.9 Hz), 3.76(1H, t, J=7.6 Hz), 4.39(1H, br s), 6.56(1H, d, J=8.6 Hz), 6.62(1H, s), 6.80(1H, d, J=8.3 Hz), 7.17(2H, d, J=8.3 Hz), 7.44-7.60(6H, m), 10.64(1H, s). FABMS: 585 (M + H)⁺. |
| 90 | ⟨–O⌒O–OMe⟩ | $^1$H-NMR(DMSO-$d_6$) δ: 0.67-1.01(15H, m), 1.40-1.70(1H, m), 2.47-2.66(1H, m), 2.81-3.04(1H, m), 3.17-3.29(1H, m), 3.38(3H, s), 3.81-4.04(2H, m), 5.22(2H, s), 6.98-7.18(4H, m), 7.21-7.37(1H, m), 7.43-7.60(5H, m), 10.60(1H, s), 12.41(1H, br s). FABMS: 629 (M + H)⁺. |
| 91 | ⟨–O⌒O⌒O–OMe⟩ | $^1$H-NMR(CDCl$_3$) δ: 0.73-1.04(16H, m), 1.54-1.80(1H, m), 2.55-2.73(1H, m), 2.89-3.08(1H, m), 3.30-3.46(3H, m), 3.51-3.60(2H, m), 3.73-3.86(3H, m), 3.94-4.12(1H, m), 5.26(2H, s), 7.03-7.37(8H, m), 7.47-7.60(2H, m), 7.74-7.93(1H, br). FABMS: 673 (M + H)⁺. |

Example 92

Preparation of 3-[4-(2,6-dichlorobenzoyl amino)phenyl]-2-{3-[(2,2-dimethylpropionyl)isobutyl amino]-4-isopropoxyphenyl}propionic acid

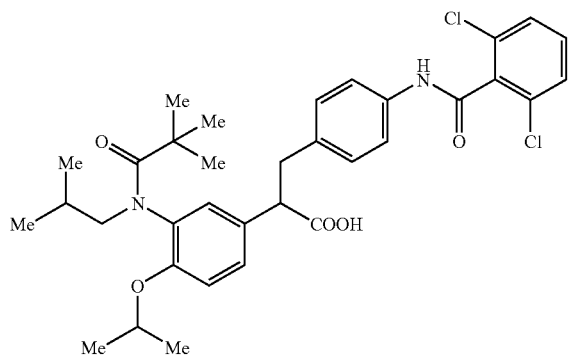

Ethyl 4-hydroxyphenylacetate (11.65 g, 64.7 mmol) was dissolved in acetone (400 mL), the solution was further added with potassium carbonate (30 g, 217 mmol) and isopropyl iodide (14 mL, 140 mmol), and stirred at room temperature for 72 hours. The solid matter was collected by filtration, evaporated under reduced pressure so as to remove the solvent, and the resultant residue was purified through silica gel column chromatography (hexane:ethyl acetate (v/v)=4:1) to thereby obtain ethyl 4-isopropoxyphenylacetate (yield: 9.21 g, yield ratio: 64%) as a light yellow syrup.

Thus obtained ethyl 4-isopropoxyphenylacetate (9.21 g, 41.5 mmol) was dissolved in acetic acid (200 mL), and a catalytic amount of concentrated sulfuric acid (0.5 mL) was added. The solution was added drop-wisely with a 60 wt % nitric acid (4.72 mL, 62 mmol) while heating the solution at 60° C., and then stirred for 2 hours. The reaction solution was poured into 500 mL of icy water, extracted with ethyl acetate, the extract was dried over anhydrous sodium sulfate, evaporated under reduced pressure so as to remove the solvent, and the resultant residue was purified through silica gel column chromatography (hexane:ethyl acetate (v/v)=5:1 to 3:1) to thereby obtain ethyl 4-isopropoxy-3-nitrophenyl acetate (yield: 3.81 g, yield ratio: 34%).

The process steps thereafter are same as those described in steps 1 to 10 of preparation method C for Example 38, to thereby obtain the compound of Example 92.

Compounds of Examples 93 to 96 were also prepared similarly to Example 92.

Physical properties of these compounds are shown in Table 9 below.

TABLE 9

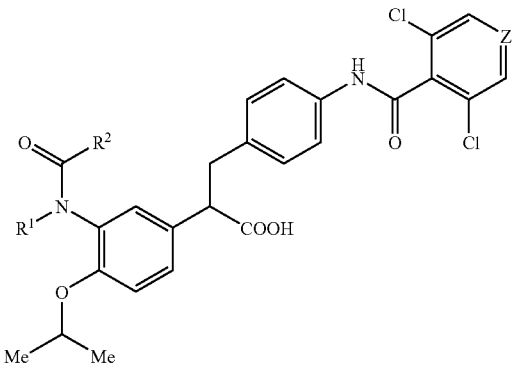

| Example No. | R$^1$ | R$^2$ | Z | NMR, MS |
|---|---|---|---|---|
| 92 | Me-CH(Me)-CH$_2$- | -C(Me)$_3$ | CH | $^1$H-NMR(CDCl$_3$)δ: 0.76-1.02(15H, m), 1.24-1.38(6H, m), 1.53-1.81(1H, m), 2.65-2.81(1H, m), 2.90-3.06(1H, m), 3.30-3.47(1H, m), 3.78(1H, t, J=7.6Hz), 4.56(1H, m), 6.82(1H, d, J=8.9Hz), 7.02-7.34(6H, m), 7.54(2H, t, J=8.2Hz), 7.90(1H, d, J=18.2Hz). FABMS: 627(M+H)$^+$. |
| 93 | Me-CH(Me)-CH$_2$- | -C(Me)$_3$ | N | $^1$H-NMR(CDCl$_3$)δ: 0.75-1.00(15H, m), 1.23-1.40(6H, m), 1.58-1.79(1H, m), 2.67-2.83(1H, m), 2.89-3.05(1H, m), 3.30-3.46(1H, m), 3.67-3.94(2H, m), 4.56(1H, m), 6.83(1H, d, J=8.9Hz), 7.06-7.33(4H, m), 7.46-7.58(2H, m), 8.46(2H, s), 8.50-8.72(1H, m). FABMS: 628(M+H)$^+$. |
| 94 | Me-CH(Me)-CH$_2$- | -CH$_2$-CH(Me)-Me | CH | $^1$H-NMR(CDCl$_3$)δ: 0.57-0.96(12H, m), 1.16-1.98(12H, m), 2.90-3.15(2H, m), 3.30-3.45(1H, m), 3.67-3.87(2H, m), 4.57(1H, m), 6.87(1H, d, J=8.9Hz), 7.00-7.36(7H, m), 7.51-7.60(2H, m), 7.99(1H, d, J=9.2Hz). FABMS: 641(M+H)$^+$. |
| 95 | Me-CH(Me)-CH$_2$- | -CH$_2$-CH(Me)-Me | N | $^1$H-NMR(DMSO-d$_6$)δ: 0.50-0.96(12H, m), 1.01-1.97(12H, m), 2.80-3.07(2H, m), 3.13-3.40(1H, m), 3.58-3.89(2H, m), 4.66(1H, m), 6.85-7.20(4H, m), 7.28(1H, m), 7.49(2H, t, J=7.9Hz), 8.78(2H, s), 10.82(1H, d, J=5.3Hz), 12.41(1H, s). FABMS: 642(M+H)$^+$. |

TABLE 9-continued

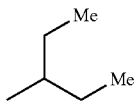

| Example No. | R¹ | R² | Z | NMR, MS |
|---|---|---|---|---|
| 96 | —H | Me (isobutyl with two Me) | CH | $^1$H-NMR(CDCl$_3$)δ: 0.95(6H, t, J=7.4Hz), 1.36(6H, d, J=5.9Hz), 1.45-1.78(4H, m), 2.05(1H, m), 2.98(1H, dd, J=4.8, 13.9Hz), 3.30-3.46(1H, m), 3.80(1H, dd, J=5.0, 10.2Hz), 4.56(1H, m), 6.83(1H, d, J=8.6Hz), 7.04(1H, dd, J=1.8, 8.4Hz), 7.13-7.31(6H, m), 7.55(2H, d, J=8.6Hz), 7.80(1H, s), 8.07(1H, s), 8.45(1H, d, J=2.0Hz). FABMS: 585(M+H)$^+$. |

Example 97

Preparation of 3-[4-(2,6-dichlorobenzoyl amino)phenyl]-2-{3-[(2,2-dimethylpropionyl)isobutyl amino]-4-ethylphenyl}propionic acid

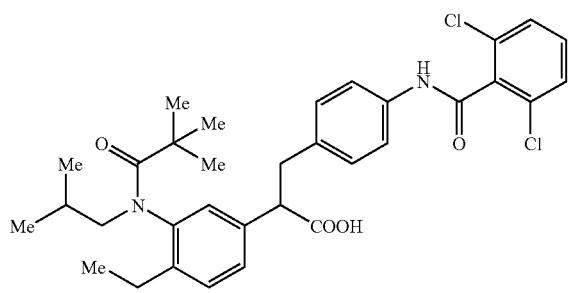

Ethyl 4-hydroxy-3-nitrophenylacetate (5.17 g, 23 mmol) was dissolved in 1,2-dichloroethane (100 mL), and was added drop-wisely with trifluoromethanesulfonic acid anhydride (5.05 mL, 30 mmol) in the presence of pyridine (3.24 mL, 40 mmol) at 0° C., the mixture was heated to room temperature, and then stirred for 20 minutes. The reaction solution was treated with a 1 mol/L hydrochloric acid (50 mL). The solution was extracted with chloroform, dried over anhydrous sodium sulfate, evaporated under reduced pressure so as to remove the solvent, and the resultant residue was purified through silica gel column chromatography (hexane:ethyl acetate (v/v)=3:1) to thereby obtain 3-nitro-4-trifluoromethanesulfonyloxyphenylacetic acid ethyl ester (yield: 7.9 g, yield ratio: 96%) as a syrup.

A 1 mol/L zinc chloride solution (in ether, 27 mL, 27 mmol) was added to tetrahydrofuran (18 mL), further added with a 3 mol/L ethyl bromide magnesium solution (in ether, 9 mL, 27 mmol) at 0° C., the mixture was stirred at room temperature for 1 hour to thereby prepare a zinc reagent. Dichlorobis(triphenylphosphine) palladium (II) (351 mg, 0.5 mmol) was dissolved in tetrahydrofuran (15 mL), added with a 1 mol/L hydrogenated diisobutyl aluminium solution (in toluene, 1 mL, 1 mmol) at 0° C., and the solution was stirred at room temperature for 30 minutes. The solution was again cooled to 0° C., added with a tetrahydrofuran solution (27 mL) of 3-nitro-4-trifluoromethanesulfonyloxyphenylacetic acid ethyl ester (3.21 g, 9 mmol), and was further added with the zing reagent previously prepared in the above. The mixture was stirred at room temperature for 1 hour, and treated with a 1 mol/L hydrochloric acid (80 mL). The solution was extracted with ethyl acetate, washed with an aqueous saturated sodium hydrogen carbonate solution, and the extract was dried over anhydrous sodium sulfate. The solvent was evaporated under reduced pressure, and the resultant residue was purified through silica gel column chromatography (hexane:ethyl acetate (v/v)=10:1 to 6:1) to thereby obtain 4-ethyl-3-nitrophenylacetic acid ethyl ester (yield: 880 mg, yield ratio: 41%).

Thus obtained 4-ethyl-3-nitrophenylacetic acid ethyl ester (1.01 g, 4.26 mmol) and 10 wt % of palladium/carbon (100 mg) were dissolved in methanol (30 mL), and stirred under a hydrogen atmosphere (3 kgf/cm$^2$) for 4 hours. The reaction solution was filtered through Celite so as to remove the palladium/carbon catalyst, the solvent was removed in vacuo, and the resultant residue was purified through silica gel column chromatography (hexane:ethyl acetate (v/v)=3:1 to 1:1) to thereby obtain 3-amino-4-ethylphenylacetic acid ethyl ester (yield: 950 mg, yield ratio: 108%) containing a trace amount of solvent.

Thus obtained 3-amino-4-ethylphenylacetic acid ethyl ester (939 mg, 4.5 mmol) and isobutylaldehyde (0.59 mL, 6.5 mmol) were dissolved in an absolute methanol (25 mL). The solution was added with sodium triacetoxyborohydride (2.86 g, 13.5 mmol) and acetic acid (3 drops), and stirred at room temperature for 14 hours. The solvent was evaporated under reduced pressure, and added with water. The solution was then extracted with ethyl acetate, the extract was dried over anhydrous sodium sulfate, evaporated under reduced pressure so as to remove the solvent, and the resultant residue was purified through silica gel column chromatography (hexane:ethyl acetate (v/v)=10:1) to thereby obtain 4-ethyl-3-isobutylaminophenylacetic acid ethyl ester (yield: 942 mg, yield ratio: 79%).

Thus obtained 4-ethyl-3-isobutylaminophenylacetic acid ethyl ester (930 mg, 3.5 mmol) was dissolved in chloroform (20 mL), and added with pivaloyl chloride (1.3 mL, 11 mmol) at 0° C. The mixture was further added with triethylamine (2.0 mL, 14 mmol), and stirred at room temperature for 4 hours. The reaction solution was treated with a 1 mol/L hydrochloric acid. The solution was extracted with chloroform, washed with brine, dried over anhydrous sodium sulfate, the solvent is removed in vacuo, and the resultant residue was purified through silica gel column chromatography (hexane:ethyl acetate (v/v)=6:1 to 4:1) to thereby obtain {3-[(2,2-dimethylpropionyl)isobutyl amino]-4-ethylphenyl}acetic acid ethyl ester (1.06 g, yield ratio: 86%).

Thus obtained {3-[(2,2-dimethylpropionyl)isobutyl amino]-4-ethylphenyl}acetic acid ethyl ester (1.05 g, 3.0 mmol) was dissolved in tetrahydrofuran (15 mL), and added drop-wisely with a 2 mol/L lithium diisopropylamide (heptane/tetrahydrofuran/ethylbenzene solution, 1.75 mL, 3.5 mmol) at −78° C. The mixture was stirred for 1 hour, and added drop-wisely with a tetrahydrofuran solution (10 mL) of 4-nitrobenzyl bromide (864 mg, 4.0 mmol). The mixture was heated to room temperature, and stirred for additional 1 hour. The reaction solution was then treated with a saturated aqueous ammonium chloride solution, extracted with ethyl acetate, the extract was dried over anhydrous magnesium sulfate, the solvent is removed in vacuo, and the resultant residue was purified through silica gel chromatography (hexane:ethyl acetate (v/v)=4:1) to thereby obtain 2-{3-[(2,2-dimethyl propionyl)isobutylamino]-4-ethylphenyl}-3-(4-nitro phenyl)propionic acid ethyl ester (yield: 1.44 g, yield ratio: 98%).

The process steps thereafter are same as those described in steps 7 to 10 of preparation method C for Example 38, to thereby obtain the compound of Example 97.

Compounds of Examples 98 to 100 were also prepared similarly to Example 97.

Physical properties of these compounds are shown in Table 10 below.

TABLE 10

| Example No. | B | Z | NMR, MS |
|---|---|---|---|
| 97 | —Et | CH | $^1$H-NMR(CDCl$_3$)δ: 0.71-1.02(15H, m), 1.23(3H, t, J=7.4Hz), 1.60-1.90(1H, m), 2.26-2.60(3H, m), 2.93-3.12(1H, m), 3.32-3.48(1H, m), 3.84(1H, t, J=7.6Hz), 4.15-4.31(1H, m), 7.03-7.39(8H, m), 7.54(2H, t, J=8.7Hz), 7.77(1H, d, J=18.5Hz). FABMS: 597(M+H)$^+$. |
| 98 | —Et | N | $^1$H-NMR(DMSO-d$_6$)δ: 0.60-1.00(15H, m), 1.18(3H, t, J=7.4Hz), 1.35-1.78(1H, m), 2.20-2.55(3H, m), 2.83-3.07(1H, m), 3.16-3.47(1H, m), 3.91(1H, m), 4.12(1H, m), 6.90-7.24(3H, m), 7.26-7.57(4H, m), 8.78(2H, s), 10.81(1H, d, J=8.6Hz), 12.47(1H, s). FABMS: 598(M+H)$^+$. |
| 99 | ~~~~~Me | CH | $^1$H-NMR(CDCl$_3$)δ: 0.71-1.05(18H, m), 1.32-1.50(2H, m), 1.52-1.90(3H, m), 2.30-2.52(3H, m), 2.93-3.10(1H, m), 3.33-3.48(1H, m), 3.83(1H, m), 4.15-4.32(1H, m), 7.03-7.38(8H, m), 7.54(2H, d, J=8.4Hz), 7.83(1H, d, J=18.8Hz). FABMS: 625(M+H)$^+$. |
| 100 | ~~~~~Me | N | $^1$H-NMR(CDCl$_3$)δ: 0.68-1.02(18H, m), 1.31-1.50(2H, m), 1.51-1.90(3H, m), 2.30-2.51(3H, m), 2.90-3.10(1H, m), 3.31-3.52(1H, m), 3.76-3.90(1H, m), 4.09-4.28(1H, m), 7.02-7.38(5H, m), 7.45-7.57(2H, m), 8.44(2H, s), 8.75(1H, d, J=15.8Hz). FABMS: 626(M+H)$^+$. |

Example 101

Preparation of 3-[4-(2,6-dichlorobenzoyl amino) phenyl]-2-{3-[(2,2-dimethylpropionyl)isobutyl amino]-5-(trifluoromethyl)phenyl}propionic acid 3-Trifluoromethyl-5-nitrobenzoic acid (2.35 g, 10 mmol) was dissolved in chloroform (50 mL), the solution was further added with oxalyl chloride (2.2 mL, 25 mmol) and a catalytic amount of dimethylformamide, and stirred for 1.5 hours. The solvent was evaporated under reduced pressure to thereby obtain a correspondent crude acid chloride. Thus obtained acid chloride is dissolved in acetonitrile (50 mL), added with a 2 mol/mL trimethylsilyldiazomethane solution (in hexane, 6.3 mL, 12.6 mmol) and triethylamine (1.7 mL, 12 mmol) while keeping the mixture at 0° C., and stirred for 1 hour. The reaction solution was treated with an aqueous saturated sodium hydrogen carbonate solution, extracted with ethyl acetate, the extract was dried over anhydrous sodium sulfate, evaporated under reduced pressure so as to remove the solvent to thereby obtain 2-diazo-1-(3-nitro-5-trifluoromethylphenyl)-2-trimethylsilanylethanone as a crude product.

Thus obtained crude 2-diazo-1-(3-nitro-5-trifluoro methylphenyl)-2-trimethylsilanylethanone was dissolved in ethanol (100 mL), added with a triethylamine (5 mL) solution of silver benzoate (687 mg, 3 mmol), and stirred at 90° C. for 1 hour. The solvent was evaporated under reduced pressure, and added with a saturated sodium hydrogen carbonate solution. The solution was extracted with ethyl acetate, the extract was dried over anhydrous sodium sulfate, evaporated under reduced pressure so as to remove the solvent, and the resultant residue was purified through silica gel column chromatography (hexane:ethyl acetate (v/v)=8:1 to 4:1) to thereby obtain 3-trifluoromethyl-5-nitrophenylacetic acid ethyl ester (yield: 1.26 g, yield ratio: 46%).

The process steps thereafter for obtaining the compound of Example 101 are same as those described in Example 97. Compounds of Examples 102 to 104 were also prepared similarly to Example 101.

Physical properties of these compounds are shown in Table 11 below.

Example 105

Preparation of 3-(4-bromophenyl)-2-{3-[(2,2-dimethylpropionyl)isobutylamino]-4-methoxyphenyl} propionic acid

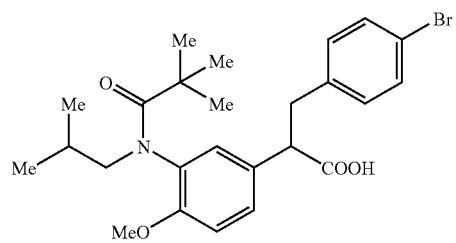

Diisopropylamine (0.20 mL, 1.43 mmol) was dissolved in tetrahydrofuran (10 mL), and the mixture was added drop-wisely with a 1.6 mol/L hexane solution of n-butyl lithium (0.825 mL, 1.32 mmol) at −78° C. The solution was stirred for 15 minutes, and added with a tetrahydrofuran solution (5 mL) of 3-[(2,2-dimethylpropionyl)isobutyl amino]-4-methoxyphenylacetic acid ethyl ester (384 mg, 1.1 mmol) while keeping the solution at −78° C. The solution was stirred for 1 hour, and added drop-wisely with a tetrahydrofuran solution (5 mL) of 4-bromobenzyl bromide (357 mg, 1.43 mmol) while keeping the solution at −78° C. The solution was then gradually heated to room temperature over 1 hour under

TABLE 11

| Example No. | B | C | Z | NMR, MS |
|---|---|---|---|---|
| 101 | —H | —CF$_3$ | CH | $^1$H-NMR(CDCl$_3$) δ: 0.83-0.90(6H, m), 0.92(9H, s), 1.70(1H, m), 3.05(1H, dd, J=6.8, 13.7 Hz), 3.36-3.50(3H, m), 3.95(1H, t, J=7.6 Hz), 7.14(2H, d, J=8.6 Hz), 7.23-7.38(5H, m), 7.51-7.63(3H, m), 7.83(1H, br s). FABMS: 637 (M + H)$^+$. |
| 102 | —H | —CF$_3$ | N | $^1$H-NMR(DMSO-d$_6$) δ: 0.72-0.90(15H, m), 1.51(1H, m), 3.07(1H, dd, J=9.4, 13.7 Hz), 3.26-3.43(3H, m), 4.18(1H, t, J=7.9 Hz), 7.15(2H, d, J=8.3 Hz), 7.39-7.53(4H, m), 7.72(1H, s), 8.79(2H, s), 10.82(1H, s), 12.73(1H, br s). FABMS: 638 (M + H)$^+$. |
| 103 | —OMe | —OMe | CH | $^1$H-NMR(CDCl$_3$) δ: 0.79-1.06(17H, m), 1.75(1H, m), 3.00(1H, dd, J=6.8, 13.7 Hz), 3.39(1H, dd, J=8.6, 13.5 Hz), 3.79(1H, t, J=7.8 Hz), 3.86(6H, s), 6.76(1H, br s), 6.88(1H, br s), 7.15(2H, d, J=8.6 Hz), 7.22-7.33(3H, m), 7.55(2H, d, J=8.6 Hz), 7.89(1H, br s). FABMS: 629 (M + H)$^+$. |
| 104 | —OMe | —OMe | N | $^1$H-NMR(CDCl$_3$) δ: 0.77-1.03(17H, m), 1.73(1H, m), 2.92-3.06(1H, m), 3.31-3.46(1H, m), 3.79(1H, dd, J=6.1, 9.1 Hz), 3.87(6H, s), 6.77(1H, br s), 6.90(1H, br s), 7.18(2H, d, J=7.9 Hz), 7.53(2H, d, J=7.9 Hz), 8.46(2H, br s). FABMS: 630 (M + H)$^+$. | stirring, and treated with a saturated aqueous ammonium chloride solution. The solution was extracted with ethyl acetate, the extract was dried over anhydrous sodium sulfate, evaporated under reduced pressure so as to remove the solvent, and the resultant residue was purified through silica gel column chromatography (hexane:ethyl acetate (v/v)=4: 1) to thereby obtain 3-(4-bromophenyl)-2-{3-[(2,2-dimethylpropionyl)isobutylamino]-4-methoxyphenyl}p ropionic acid ethyl ester (yield: 570 mg, yield ratio: 100%) as a colorless syrup.

Thus obtained 3-(4-bromophenyl)-2-{3-[(2,2-dimethylpropionyl)isobutylamino]-4-methoxyphenyl} propionic acid ethyl ester (104 mg, 0.2 mmol) was dissolved in a mixed solvent of methanol (3 mL) and tetrahydrofuran (3 mL), and the mixture was added with a 2 mol/L aqueous sodium hydroxide solution (3 mL, 6 mmol). The solution was evaporated under reduced pressure so as to remove the solvent, the resultant residue was added with water to be dissolved, and the solution was washed with diethyl ether. The separated aqueous phase was added with a 1 mol/L hydrochloric acid so as to adjust pH of the solution as low as 4 or below. The solution was then extracted with ethyl acetate, the extract was dried over anhydrous sodium sulfate, evaporated under reduced pressure so as to remove the solvent, to thereby obtain 3-(4-bromophenyl)-2-{3-[(2,2-dimethylpropionyl)isobutyl amino]-4-methoxyphenyl}propionic acid (yield: 89 mg, yield ratio: 90%) as a white solid.

Physical properties of the product were shown in Table 12 below.

Example 106

Preparation of 3-(2',6'-dimethoxybiphenyl-4-yl-2-{3-[(2,2-dimethylpropionyl)isobutylamino]-4-methoxyphenyl}propionic acid

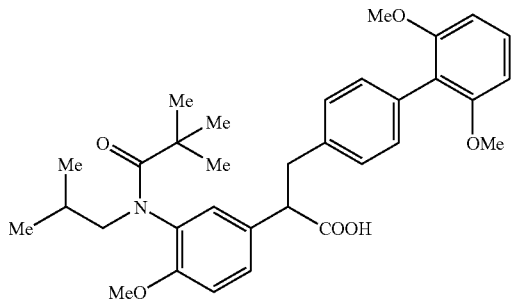

3-(4-bromophenyl)-2-{3-[(2,2-dimethylpropionyl) isobutylamino]-4-methoxyphenyl}propionic acid ethyl ester (207 mg, 0.4 mmol) obtained in step 1 of preparation method "A" described above in Example 105, 2,6-dimethoxyphenylboric acid (218 mg, 1.2 mmol), tetrakis(triphenylphosphine) palladium (312 mg, 0.27 mmol) and potassium carbonate (332 mg, 2.4 mmol) were dissolved in a mixed solvent of 1,2-dimethoxyethane (10 mL) and water (0.1 mL), and the mixture was stirred under an argon gas atmosphere at 90° C. for 14 hours. The solution was treated with a saturated aqueous sodium chloride solution. The solution was then extracted with ethyl acetate, the extract was dried over anhydrous sodium sulfate, evaporated under reduced pressure so as to remove the solvent, and the resultant residue was purified through silica gel column chromatography (toluene:ethyl acetate (v/v)=7:1) to thereby obtain 3-(2',6'-dimethoxybiphenyl-4-yl)-2-{3-[(2,2-dimethylpropionyl)isobutylamino]-4-methoxyphenyl}propionic acid ethyl ester (yield: 110 mg, yield ratio: 48%).

Thus obtained 3-(2',6'-dimethoxybiphenyl-4-yl)-2-{3-[(2,2-dimethylpropionyl)isobutylamino]-4-methoxyphenyl}propionic acid ethyl ester (110 mg, 0.19 mmol) was dissolved in a mixed solvent of methanol (2 mL) and tetrahydrofuran (2 mL), and the mixture was added with a 2 mol/L aqueous sodium hydroxide solution (2 mL, 4 mmol). The solution was evaporated under reduced pressure so as to remove the solvent, the resultant residue was added with water to be dissolved, and the solution was washed with diethyl ether. The separated aqueous phase was added with a 1 mol/L hydrochloric acid so as to adjust pH of the solution to as low as 4 or below. The solution was then extracted with ethyl acetate, the extract was dried over anhydrous sodium sulfate, evaporated under reduced pressure so as to remove the solvent to thereby obtain 3-(2',6'-dimethoxybiphenyl-4-yl)-2-{3-[(2,2-dimethylpropionyl)isobutylamino]-4-methoxyphenyl} propionic acid (yield: 95 mg, yield ratio: 91%) as a white solid.

Physical properties of the product are shown in Table 12 below.

Example 107

Preparation of 3-[4-(2,6-dichlorophenyl ethynyl) phenyl]-2-{3-[(2,2-dimethylpropionyl)isobutyl amino]-4-methoxyphenyl}propionic acid

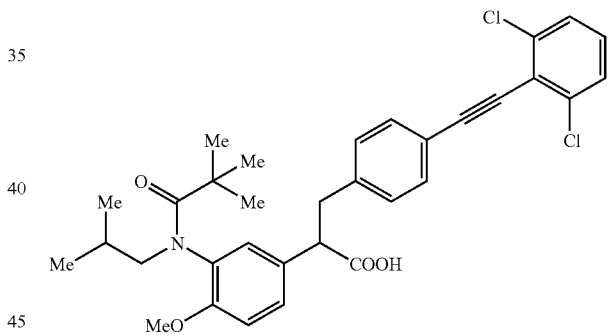

3-(4-iodophenyl)-2-{3-[(2,2-dimethylpropionyl) isobutylamino]-4-methoxyphenyl}propionic acid ethyl ester (0.15 g, 0.27 mmol) was dissolved in triethylamine (2 mL), the solution was further added with 1,3-dichloro-2-ethynylbenzene (0.15 g, 0.53 mmol), copper iodide (I) (5 mg, 0.026 mmol) and tetrakis(triphenylphosphine) palladium (15 mg, 0.013 mmol), and the mixture was stirred at room temperature for 15 hours. The solution was treated with a citric acid solution. The solution was then extracted with ethyl acetate, washed with a saturated brine, the extract was dried over anhydrous magnesium sulfate, evaporated under reduced pressure so as to remove the solvent, and the resultant residue was purified through silica gel column chromatography (hexane:ethyl acetate (v/v)=3:1) to thereby obtain 3-[4-(2,6-dichlorophenylethynyl)phenyl]-2-{3-[(2,2-dimethylpropionyl)isobutylamino]-4-methoxyphenyl} propionic acid ethyl ester (yield: 0.11 g, yield ratio: 68%).

The process step thereafter is same as those described in step 10 of preparation method C for Example 38, to thereby obtain the compound of Example 107.

Physical properties of this compound are shown in Table 12 below.

TABLE 12

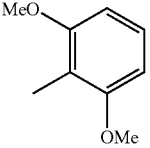

| Example No. | X | NMR, MS |
|---|---|---|
| 105 | —Br | $^1$H-NMR(CDCl$_3$) δ: 0.70-1.02(15H, m), 1.55-1.78(1H, m), 2.50-2.73(1H, m), 2.89-3.09(1H, m), 3.34(1H, dd, J=6.9, 13.9 Hz), 6.84(1H, d, J=8.6 Hz), 6.94(2H, d, J=8.3 Hz), 7.03(1H, s), 7.18-7.38(3H, m). FABMS: 490 (M + H)$^+$. |
| 106 | 2,6-(MeO)$_2$-3-Me-phenyl | $^1$H-NMR(CDC$_3$) δ: 0.75-1.04(15H, m), 1.60-1.86(1H, m), 2.60-2.75(1H, m), 2.99-3.13(1H, m), 3.37-3.53(1H, m), 3.70(6H, s), 3.79(3H, s), 3.84-4.10(2H, m), 6.63(2H, d, J=8.2 Hz), 6.85(1H, d, J=8.6 Hz), 7.08-7.37(7H, m). FABMS: 548 (M + H)$^+$. |
| 107 | 2,6-Cl$_2$-3-propynyl-phenyl | $^1$H-NMR(CDCl$_3$) δ: 0.8-1.0(15H, m), 1.5&1.8(1H, br s), 2.7(1H, m), 3.1(1H, m), 3.4(1H, dd, J=6.9, 14.2 Hz), 3.8(3H, s), 3.8(1H, m), 4.0(1H, m), 6.8(1H, d, J=8.6 Hz), 7.1-7.6(9H, m). FABMS: 580 (M + H)$^+$. |

Compounds of Examples 108 to 110 were also prepared similarly to Example 106. Physical properties of these compounds are shown in Table 13 below.

TABLE 13

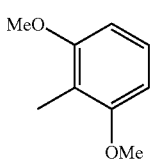

| Example No. | X | NMR, MS |
|---|---|---|
| 108 | 2,6-(MeO)$_2$-phenyl | $^1$H-NMR(DMSO-d$_6$) δ: 0.60-0.87(12H, m), 0.96(3H, t, J=7.4 Hz), 1.13-1.73(6H, m), 1.86-1.93(2H, m), 2.88-3.05(2H, m), 3.21-3.28(2H, m), 3.63(6H, s), 3.72-3.83(1H, m), 3.90-3.93(2H, m), 6.71(2H, d, J=8.3 Hz), 7.05-7.30(8H, m), 12.40(1H, br s). FABMS: 590 (M + H)$^+$. |

TABLE 13-continued

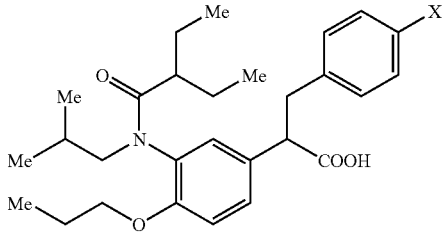

| Example No. | X | NMR, MS |
|---|---|---|
| 109 | 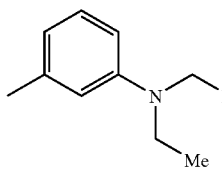 | $^1$H-NMR(DMSO-$d_6$) δ: 0.54-0.86(12H, m), 0.94(3H, t, J=7.4 Hz), 1.03-1.89(8H, m), 2.83-3.05(2H, m), 3.24-3.34(2H, m), 3.72-3.93(3H, m), 6.79-7.32(6H, m), 7.56-7.69(4H, m), 12.40(1H, br s). FABMS: 598 (M + H)$^+$. |
| 110 | 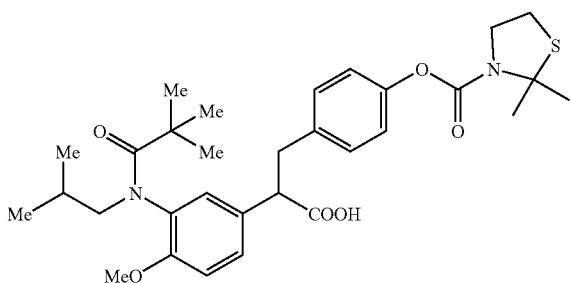 | $^1$H-NMR(DMSO-$d_6$) δ: 0.53-0.86(12H, m), 0.94(3H, t, J=7.3 Hz), 1.10(6H, t, J=6.3 Hz), 1.16-1.91((H, m), 2.84-3.05(2H, m), 3.25-3.33(1H, m), 3.71-3.91(4H, m), 6.63(1H, d, J=8.6 Hz), 6.73-6.76(2H, m), 6.99-7.08(2H, m), 7.15-7.21(3H, m), 7.27-7.33(1H, m), 7.40-7.46(2H, m), 12.39(1H, br s). FABMS: 601 (M + H)$^+$. |

Example 111

Preparation of 2,2-dimethylthiazolidine-3-carboxylic acid 4-(2-carboxy-2-{3-[(2,2-dimethyl propionyl)isobutylamino]-4-methoxyphenyl}ethyl)phenyl ester Diisopropylamine (0.35 mL, 2.5 mmol) was dissolved in tetrahydrofuran (20 mL), and the solution was added drop-wisely with a 1.6 mol/L hexane solution of n-butyl lithium (1.5 mL, 2.4 mmol) at −78° C. The mixture was stirred for 30 minutes while keeping the temperature thereof at −78° C., and was then added drop-wisely with a tetrahydrofuran solution (10 mL) of 3-[(2,2-dimethylpropionyl)isobutyl amino]-4-methoxyphenylacetic acid ethyl ester (0.72 g, 2.1 mmol) while keeping the temperature thereof again at −78° C. The solution was stirred 30 minutes, and was further added drop-wisely with a tetrahydrofuran solution (10 mL) of 4-benzyloxybenzyl bromide (0.69 g, 2.5 mmol) while keeping the temperature thereof at −78° C. The solution was then gradually heated to room temperature over 1 hour under stirring, and treated with a saturated aqueous ammonium chloride solution. The solution was extracted with ethyl acetate, the extract was dried over anhydrous magnesium sulfate, evaporated under reduced pressure so as to remove the solvent, and the resultant residue was purified through silica gel column chromatography (hexane:ethyl acetate (v/v)=4:1) to thereby obtain 3-(4-benzyloxyphenyl)-2-{3-[(2,2-dimethylpropionyl)isobutylamino]-4-methoxyphenyl} propionic acid ethyl ester (yield: 0.79 g, yield ratio: 70%).

Thus obtained 3-(4-benzyloxyphenyl)-2-{3-[(2,2-dimethylpropionyl)isobutylamino]-4-methoxyphenyl} propionic acid ethyl ester (0.79 g, 1.4 mmol) and 10 wt % of palladium/carbon (0.79 g) were dissolved in ethanol (20 mL), and the mixture was stirred under a hydrogen atmosphere (3 kg/cm$^2$) for 2 hours. The solution was filtered through Celite so as to remove the palladium/carbon catalyst, evaporated under reduced pressure so as to remove the solvent, and the resultant residue was purified through silica gel column chromatography (hexane:ethyl acetate (v/v)=2:1) to thereby obtain 3-(4-hydroxyphenyl)-2-{3-[(2,2-dimethyl propionyl)isobutylamino]-4-methoxyphenyl}propionic acid ethyl ester (yield: 0.63 g, yield ratio: 95%).

Bis(trichloromethyl) carbonate (33 mg, 0.11 mmol) was dissolved in dichloromethane (5 mL), and 3-(4-hydroxy phenyl)-2-{3-[(2,2-dimethylpropionyl)isobutylamino]-4-methoxyphenyl}propionic acid ethyl ester (0.15 g, 0.34 mmol) obtained in the above and a dichloromethane solution of N-ethyldiisopropylamine (0.06 mL, 0.34 mmol) were added thereto, and the mixture was stirred for 15 minutes. The mixture was further added with dichloromethane solutions of 2,2-dimethylthiazolidine (42 mg, 0.14 mmol) and N-ethyldiisopropylamine (0.06 mL, 0.34 mmol), and stirred for 1 hour. The solution was then treated with water, and evaporated under reduced pressure so as to remove the solvent. The resultant residue was added with ethyl acetate, and was then successively washed with aqueous potassium hydrogen sulfate solution, aqueous sodium hydrogen carbonate solution and brine. The separated organic phase was dried over anhydrous magnesium sulfate, evaporated under reduced pressure so as to remove the solvent, and the resultant residue was purified through silica gel column chromatography (hexane:ethyl acetate (v/v)=5:1 to 4:1) to thereby obtain 2,2-dimethylthiazolidine-3-carboxylic acid 4-(2-{3-[(2,2-dimethylpropionyl)isobutylamino]-4-methoxy phenyl}-2-ethoxycarbonylethyl)phenyl ester (yield: 0.12 g, yield ratio: 61%).

The process step thereafter is same as those described in step 10 of preparation method C for Example 38, to thereby obtain the compound of Example 111. Compounds of Examples 112 to 117 were also prepared similarly to Example 111. Physical properties of these compounds are shown in Tables 14 and 15 below.

Example 118

Preparation of 3-{4-[(2,2-dimethyl thiazolidine-3-carbonyl)amino]phenyl}-2-{3-[(2-ethyl butylyl)isobutylamino]-4-propoxyphenyl}propionic acid

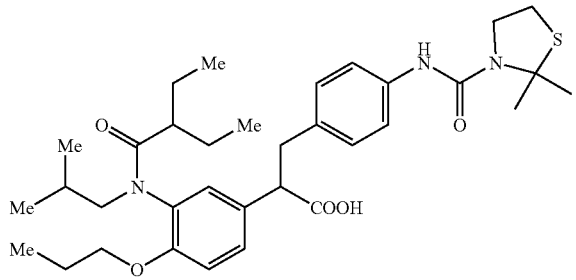

Bis(trichloromethyl) carbonate (58 mg, 0.2 mmol) was dissolved in dichloromethane (4 mL), and the mixture was further added with a dichloromethane (2 mL) solution of 3-(4-aminophenyl)-2-{3-[(2-ethylbutylyl)isobutylamino]-4-propoxyphenyl}propionic acid ethyl ester (295 mg, 0.59 mmol) and N-ethyldiisopropylamine (0.13 mL, 0.77 mmol), and was stirred for 10 minutes. The solution was further added with a dichloromethane (2 mL) solution of 2,2-dimethyl thiazolidine (0.1 mL, 0.87 mmol) and N-ethyldiisopropyl amine (0.13 mL, 0.77 mmol), and stirred for 5 hours. The solution was evaporated so as to remove the solvent, added with ethyl acetate, and successively washed with aqueous sodium hydrogen carbonate solution, aqueous citric acid solution and brine. The separated organic phase was dried over anhydrous sodium sulfate, evaporated under reduced pressure so as to remove the solvent, and the resultant residue was purified through silica gel column chromatography (hexane:ethyl acetate (v/v)=2:1) to thereby obtain 3-{4-[(2,2-dimethylthiazolidine-3-carbonyl)amino]phenyl}-2-{3-[(2-ethylbutylyl)isobutylamino]-4-propoxy phenyl}propionic acid ethyl ester (yield: 285 mg, yield ratio: 75%).

The process step thereafter is same as those described in step 10 of preparation method C for Example 38, to thereby obtain the compound of Example 118. Physical properties of the product are shown in Table 15 below.

TABLE 14

| Example No. | —NR⁴R⁵ | NMR, MS |
|---|---|---|
| 111 | (2,2-dimethylthiazolidinyl) | $^1$H-NMR(CDCl$_3$) δ: 0.79-0.97(15H, m), 1.59(1H, br s), 1.83(6H, s), 2.64(1H, br s), 2.99-3.04(3H, m), 3.37(1H, m), 3.79(3H, s), 3.80(1H, m), 4.02-4.06(3H, m), 6.83(1H, d, J=8.6 Hz), 6.95-7.09(5H, m), 7.25(1H, m). FABMS: 571 (M + H)⁺. |
| 112 | (thia-spiro group) | $^1$H-NMR(CDCl$_3$) δ: 0.80-0.97(15H, m), 1.64-1.66(3H, m), 1.71-1.92(6H, m), 2.60-2.65(2H, m), 2.96-3.01(2H, m), 3.34-3.48(1H, m), 3.79(3H, s), 3.76-3.82(2H, m), 3.98-4.02(2H, m), 6.83(1H, d, J=6.6 Hz), 6.94-7.27(6H, m). |
| 113 | (morpholinyl) | $^1$H-NMR(CDCl$_3$) δ: 0.80-0.97(15H, m), 1.72(1H, br s), 2.66(1H, m), 2.99(1H, m), 3.34-3.83(10H, m), 3.78(3H, s), 4.03(1H, m), 6.72(1H, s), 6.80(1H, d, J=8.6 Hz), 6.92-7.11(4H, m), 7.24(1H, dd, J=2.3, 8.6 Hz). FABMS: 541 (M + H)⁺. |
| 114 | (4-methylpiperazinyl) | FABMS: 554 (M + H)⁺. |

TABLE 14-continued
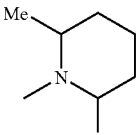
| Example No. | —NR⁴R⁵ | NMR, MS |
|---|---|---|
| 115 | 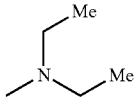 | $^1$H-NMR(CDCl$_3$) δ: 0.79-1.06(15H, m), 1.27(6H, d, J=6.9 Hz), 1.48-1.86(7H, m), 2.64(1H, m), 3.01(1H, m), 3.40(1H, m), 3.78(3H, s), 3.81(1H, br s), 4.01(1H, m), 4.42(2H, t, J=5.9 Hz), 6.82(1H, d, J=8.6 Hz), 6.94-7.10(5H, m), 7.24(1H, dd, J=2.3, 8.6 Hz). FABMS: 567 (M + H)⁺. |
| 116 | | $^1$H-NMR(CDCl$_3$) δ: 0.79-0.97(16H, m), 1.18-1.43(5H, m), 1.82(1H, br s), 2.64(1H, m), 2.99(1H, m), 3.38(5H, m), 3.78(3H, s), 3.81(1H, m), 4.04(1H, m), 6.82(1H, d, J=8.6 Hz), 6.94-7.27(5H, m), 7.25(1H, dd, J=2.0, 8.6 Hz). FABMS: 527 (M + H)⁺. |
TABLE 15
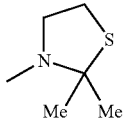
| Example No. | Z | —NR⁵R⁶ | NMR, MS |
|---|---|---|---|
| 117 | O | | $^1$H-NMR(DMSO-d$_6$) δ: 0.56-0.86(12H, m), 0.95(3H, t, J=7.4 Hz), 1.06-1.91(8H, m), 1.74(6H, s), 2.85-3.26(5H, m), 3.69-3.93(6H, m), 6.92-7.29(7H, m), 12.43(1H, br s). FABMS: 613 (M + H)⁺. |

TABLE 15-continued

| Example No. | Z | —NR⁵R⁶ | NMR, MS |
|---|---|---|---|
| 118 | NH | (2,2-dimethylthiazolidin-3-yl, N-methyl) | $^1$H-NMR(DMSO-$d_6$) δ: 0.57-0.87(12H, m), 0.94(3H, t, J=7.4 Hz), 1.09-1.94(8H, m), 1.74(6H, s), 2.76-3.21(5H, m), 3.71-3.93(6H, m), 6.92-7.04(6H, m), 7.19-7.31(3H, m), 8.03(1H, d, J=3.6 Hz), 12.34(1H, br s). FABMS: 612 (M + H)⁺. |

Example 119

Preparation of 3-[4-(2,6-dichlorobenzyloxy)phenyl]-2-{3-[(2-ethylbutylyl)isobutylamino]-4-propoxy phenyl}propionic acid

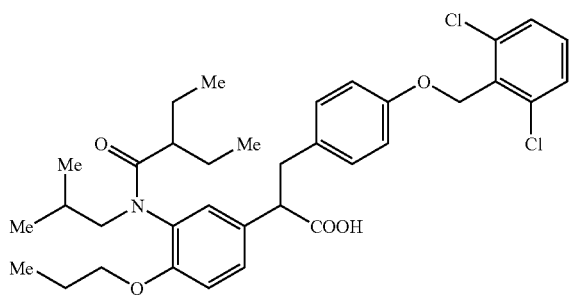

3-(4-hydroxyphenyl)-2-{3-[(2-ethylbutylyl)isobutyl amino]-4-propoxyphenyl}propionic acid ethyl ester (216 mg, 0.43 mmol) was dissolved in acetone (5 mL), the mixture was further added with 2,6-dichlorobenzyl bromide (312 mg, 1.3 mmol) and potassium carbonate (300 mg, 2.2 mmol), and refluxed under heating for 2 hours. The solvent was then removed by evaporation under reduced pressure. The resultant residue was added with ethyl acetate, and the solution was washed with water, dried over anhydrous sodium sulfate, evaporated under reduced pressure so as to remove the solvent, and the resultant residue was purified through silica gel column chromatography (hexane:ethyl acetate (v/v)=2:1) to thereby obtain 3-[4-(2,6-dichlorobenzyloxy)phenyl]-2-{3-[(2-ethylbutylyl)isobutylamino]-4-propoxyphenyl}propionic acid ethyl ester (yield: 285 mg, yield ratio: 99%).

The process step thereafter is same as those described in step 10 of preparation method C for Example 38, to thereby obtain the compound of Example 119. A compound of Example 120 was also prepared similarly to Example 119.

Physical properties of the product are shown in Table 16 below.

TABLE 16

| Example No. | Z | NMR, MS |
|---|---|---|
| 119 | CH | $^1$H-NMR(DMSO-$d_6$) δ: 0.56-0.86(12H, m), 0.95(3H, t, J=7.4 Hz), 1.07-1.91(8H, m), 2.81-2.96(2H, m), 3.15-3.25(2H, m), 3.71-3.93(3H, m), 5.14(2H, d, J=5.3 Hz), 6.83-7.08(6H, m), 7.25-7.31 (1H, m), 7.42-7.56(3H, m), 12.40(1H, br s). FABMS: 628 (M + H)⁺. |

TABLE 16-continued

| Example No. | Z | NMR, MS |
|---|---|---|
| 120 | N | $^1$H-NMR(DMSO-d$_6$) δ: 0.56-0.86(12H, m), 0.95(3H, t, J=7.4 Hz), 1.04-1.91(8H, m), 2.80-2.96(2H, m), 3.15-3.25(2H, m), 3.71-3.93(3H, m), 5.14(2H, d, J=5.9 Hz), 6.87-7.10(6H, m), 7.24-7.30(1H, m), 8.72(2H, s), 12.40(1H, br s). FABMS: 629 (M + H)$^+$. |

Examples 121 to 124

Compounds of Examples 121 to 124 were also prepared similarly to Examples 38 and 39. Physical properties of the product are shown in Table 17 below.

TABLE 17

| Example No. | R$^1$ | B | Z | NMR, MS |
|---|---|---|---|---|
| 121 | iBu (Me, Me) | —OMe | CH | $^1$H-NMR(CDCl$_3$) δ: 0.99(6H, d, J=6.9 Hz), 1.81-1.97(1H, m), 2.93(2H, d, J=6.9 Hz), 2.97-3.02(1H, m), 3.33-3.42(1H, m), 3.70-3.76(1H, m), 3.82(3H, s), 6.54-6.74(3H, m), 7.14-7.38(5H, m), 7.53(2H, d, J=8.2 Hz), 8.05(1H, s). FABMS: 515 (M + H)$^+$. |
| 122 | iBu (Me, Me) | —OMe | N | $^1$H-NMR(CDCl$_3$) δ: 0.99(6H, d, J=6.6 Hz), 1.84-1.96(1H, m), 2.93(2H, d, J=6.9 Hz), 2.97-3.02(1H, m), 3.33-3.41(1H, m), 3.68-3.74(1H, m), 3.82(3H, s), 6.56-6.69(3H, m), 7.18(2H, d, J=8.6 Hz), 7.55(2H, d, J=8.2 Hz), 8.55(2H, s), 9.59(1H, s). FABMS: 516 (M + H)$^+$. |
| 123 | (Me, Me, Me) | —OMe | CH | $^1$H-NMR(CDCl$_3$) δ: 0.87-1.11(9H, m), 1.72-1.88(1H, m), 2.94-3.02(1H, m), 3.32-3.41(2H, m), 3.68-3.71(1H, m), 3.81(3H, s), 6.53-6.69(3H, m), 7.18(2H, d, J=7.9 Hz), 7.24-7.36(3H, m), 7.54(2H, d, J=8.6 Hz), 8.39(1H, s). FABMS: 529 (M + H)$^+$. |
| 124 | iBu (Me, Me) | —OH | CH | $^1$H-NMR(CDCl$_3$) δ: 0.99(6H, d, J=6.6 Hz), 1.88(1H, m), 2.80-3.04(3H, m), 3.35(1H, dd, J=8.9, 13.9 Hz), 3.69(1H, t, J=7.8 Hz), 6.49(1H, d, J=7.6 Hz), 6.57(1H, s), 6.66(1H, d, J=7.9 Hz), 7.16(2H, d, J=8.3 Hz), 7.22-7.40(3H, m), 7.53(2H, d, J=8.6 Hz), 8.82(1H, s). FABMS: 501 (M + H)$^+$. |

Examples 125 to 137

Compounds of Examples 125 to 137 were also prepared similarly to Examples 1 and 2. Physical properties of the product are shown in Tables 18 and 19 below.

TABLE 18

| Example No. | A | B | NMR, MS |
|---|---|---|---|
| 125 | —H | —H | $^{1}$H-NMR(CDCl$_{3}$) δ: 2.98(1H, dd, J=5.0, 13.9 Hz), 3.43(1H, dd, J=10.4, 13.7 Hz), 3.82(1H, dd, J=5.0, 10.2 Hz), 7.11-7.42(10H, m), 7.57(2H, d, J=8.3 Hz), 8.03(1H, s). FABMS: 416 (M + H)$^{+}$. |
| 126 | 2,5-dimethyl-1-methylpyrrol-3-yl | —H | FABMS: 507 (M + H)$^{+}$. |
| 127 | 2,6-dimethoxy-3-methylphenyl (MeO, Me, OMe substituted phenyl) | —H | $^{1}$H-NMR(CDCl$_{3}$) δ: 3.04(1H, dd, J=5.1, 13.7 Hz), 3.42(1H, dd, J=10.4, 13.7 Hz), 3.68(6H, s), 3.84(1H, dd, J=5.1, 10.1 Hz), 6.63(2H, d, J=8.6 Hz), 7.14-7.41(10H, m), 7.53(2H, d, J=8.6 Hz), 7.91(1H, br s). FABMS: 550 (M + H)$^{+}$. |
| 128 | 1,3,3-trimethyl-2-oxoazetidin-? | —H | $^{1}$H-NMR(CDCl$_{3}$) δ: 1.38(6H, s), 2.98(1H, dd, J=5.3, 13.5 Hz), 3.34-3.47(3H, m), 3.83(1H, dd, J=5.3, 9.9 Hz), 7.07-7.32(9H, m), 7.57(2H, d, J=8.3 Hz), 8.06(1H, s). FABMS: 511 (M + H)$^{+}$. |
| 129 | —H | tert-butyl | $^{1}$H-NMR(CDCl$_{3}$) δ: 1.30(9H, s), 2.96(1H, dd, J=4.3, 13.5 Hz), 3.43(1H, dd, J=10.9, 13.5 Hz), 3.80(1H, dd, J=4.5, 10.7 Hz), 7.13-7.38(9H, m), 7.58(2H, d, J=8.3 Hz), 8.07(1H, br s). FABMS: 470 (M + H)$^{+}$. |
| 130 | —H | phenyl | $^{1}$H-NMR(CDCl$_{3}$) δ: 2.99(1H, dd, J=7.1, 13.7 Hz), 3.20-3.40(1H, m), 3.93(1H, t, J=7.8 Hz), 7.22(2H, d, J=8.2 Hz), 7.29-7.70(14H, m), 10.66(1H, s), 12.42(1H, br s). FABMS: 490 (M + H)$^{+}$. |
| 131 | —H | —NHC(=O)O-tBu | $^{1}$H-NMR(CDCl$_{3}$) δ: 1.48(9H, s), 2.93(1H, dd, J=5.6, 13.9 Hz), 3.35(1H, dd, J=9.7, 13.7 Hz), 3.75(1H, m), 6.65(1H, br s), 7.13(2H, d, J=8.3 Hz), 7.18-7.30(7H, m), 7.50(2H, d, J=8.3 Hz), 8.06(1H, br s). FABMS: 529 (M + H)$^{+}$. |
| 132 | —H | —NHC(=O)Ph | FABMS: 533 (M + H)$^{+}$. |

TABLE 18-continued

[Structure: 2-(3-A,4-B-phenyl)-3-[4-(2,6-dichlorobenzamido)phenyl]propanoic acid scaffold with COOH]

| Example No. | A | B | NMR, MS |
|---|---|---|---|
| 133 | —H | [N-methyl-2-phenylacetamide group via NH] | FABMS: 547 (M + H)+. |
| 134 | —OCH2CH(Me)Me (isobutoxy with Me) | —C(Me)3 (tert-butyl) | FABMS: 542 (M + H)+. |
| 135 | —OCH2-phenyl (benzyloxy) | —C(Me)3 (tert-butyl) | FABMS: 576 (M + H)+. |

TABLE 19

[Structure: 2-(3-B,4-C,5-A-phenyl)-3-[4-(2,6-dichlorobenzamido)phenyl]propanoic acid scaffold]

| Example No. | A | B | C | NMR, MS |
|---|---|---|---|---|
| 136 | —OCH2CH(Me)Me with OMe | —OCH2CH(Me)Me with OMe | —H | $^1$H-NMR(CDCl$_3$) δ: 1.01(12H, d, J=6.6 Hz), 1.98-2.13(2H, m), 2.91-2.98(1H, m), 3.35-3.44(1H, m), 3.64-3.73(1H, m), 3.68(4H, d, J=6.6 Hz), 6.37(1H, s), 6.51(2H, s), 7.13-7.23(5H, m), 7.58(2H, d, J=8.3 Hz), 8.09(1H, s). FABMS: 558 (M + H)+. |
| 137 | —OMe | —H | —OMe | $^1$H-NMR(CDCl$_3$) δ: 2.95(1H, dd, J=5.8, 13.7 Hz), 3.32(1H, dd, J=9.2, 13.5 Hz), 3.74(3H, s), 3.78(3H, s), 4.31(1H, dd, J=5.6, 9.2 Hz), 6.72-6.92(3H, m), 7.14-7.31(5H, m), 7.53(2H, d, J=8.6 Hz), 7.82(1H, br s). |

Example 138

A compound of Example 138 was also prepared similarly to Example 119. Physical properties of the product are shown below.

Example No. 138

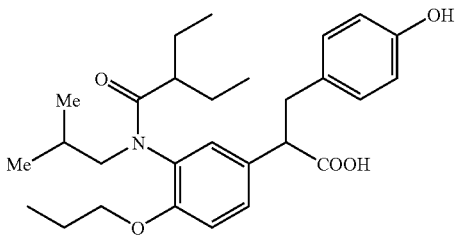

$^1$H-NMR (DMSO-d$_6$) δ: 0.56-0.86 (12H, m), 0.94 (3H, t, J=7.3 Hz), 1.06-1.71 (8H, m), 2.71-2.96 (2H, m), 3.07-3.18 (1H, m), 3.69-3.92 (4H, m), 6.52-6.59 (2H, m), 6.84-7.04 (4H, m), 7.19-7.25 (1H, m), 9.13 (1H, br s), 12.33 (1H, br s).

Example 139

Preparation of 3-{4-[(2,6-dichlorobenzoyl)methylamino]phenyl}-2-{3-[(2,2-dimethylpropionyl)isobutylamino]-4-methoxyphenyl}propionic acid

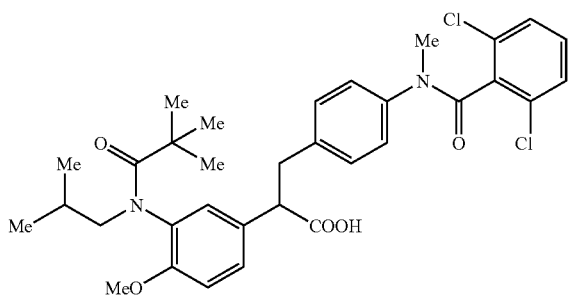

3-[4-(2,6-Dichlorobenzoyl amino)phenyl]-2-{3-[(2,2-dimethylpropionyl)isobutylamino]-4-methoxyphenyl} propionic acid ethyl ester (251 mg, 0.4 mmol) was dissolved in dimethylformamide (3 mL), the mixture was further added with sodium hydride (oil-base, 60%, 24 mg, 0.6 mmol), and stirred for 15 minutes. The mixture was further added with methyl iodide (75 µL, 1.2 mmol), and stirred at room temperature for 17 hours. The mixture was added with a saturated aqueous ammonium chloride solution, the solution was extracted with ethyl acetate, dried over anhydrous sodium sulfate, evaporated under reduced pressure so as to remove the solvent, and the resultant residue was purified through silica gel column chromatography (hexane:ethyl acetate (v/v)=3:2) to thereby obtain 3-{4-[(2,6-dichloro benzoyl)methylamino]phenyl}-2-{3-[(2,2-dimethyl propionyl)isobutylamino]-4-methoxyphenyl}propionic acid ethyl ester (yield: 234 mg, yield ratio: 91%) as a white solid.

The process step thereafter is same as those described in Example 38, to thereby obtain the compound of Example 139. Physical properties of the product are shown below.

1H-NMR (CDCl$_3$) d: 0.72-1.03 (15H, m), 1.70 (1H, m), 2.67 (1H, m), 2.90 (1H, dd, J=7.9, 13.5 Hz), 3.19-3.33 (1H, m), 3.45 (3H, s), 3.69 (1H, t, J=7.8 Hz), 3.79 (3H, s), 3.99 (1H, m), 6.78 (1H, d, J=8.6 Hz), 6.82-7.41 (9H, m).

FABMS: 613 (M+H)$^+$.

Example 140

Preparation of 3-{4-[(3,5-dichloro pyridine-4-carbonylamino)phenyl]-2-[3-(3,3-diethyl-1-isobutylureido)-4-ethoxyphenyl]propionic acid

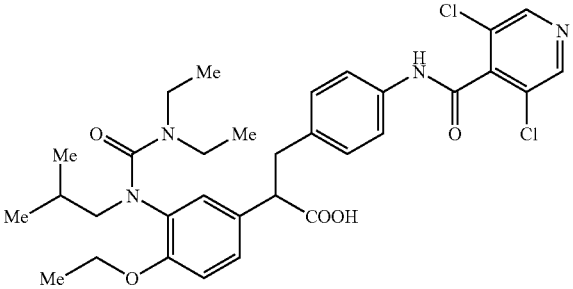

2-[(3-isobutylamino)-4-ethoxyphenyl]-3-(4-nitro phenyl) propionic acid ethyl ester (303 mg, 0.73 mmol) was dissolved in chloroform (10 mL), and the mixture was added with triethylamine (0.68 mL, 4.8 mmol). The mixture was further added with a chloroform solution (10 mL) of diethylcarbamoyl chloride (0.56 mL, 4.4 mmol) at 0° C., and then stirred at room temperature for 1 hour. The mixture was further stirred at 70° C. for 19 hours, and then evaporated under reduced pressure so as to remove the solvent. The resultant residue was treated with water, and then extracted with ethyl acetate. The organic phase was successively washed with an aqueous saturated sodium hydrogen carbonate solution and saturated brine, and dried over magnesium sulfate. The organic phase was then evaporated under reduced pressure so as to remove the solvent, and the resultant residue was purified through silica gel column chromatography (hexane:ethyl acetate (v/v)=3:2) to thereby obtain 2-[3-(3,3-diethyl-1-isobutylureido)-4-ethoxyphenyl]-3-(4-nitrophenyl)propionic acid ethyl ester (yield: 104 mg, yield ratio: 28%).

The process step thereafter is same as those described in Example 39, to thereby obtain the compound of Example 140. Physical properties of the product are shown below.

1H-NMR (DMSO-d6) d: 0.64 (6H, t, J=6.9 Hz), 0.82 (3H, d, J=6.9 Hz), 0.83 (3H, d, J=6.6 Hz), 1.28 (3H, t, J=6.9 Hz), 1.68-1.78 (1H, m), 2.84-2.96 (5H, m), 3.08 (2H, d, J=6.9 Hz), 3.19 (1H, dd, J=7.6, 13.9 Hz), 3.78 (1H, t, J=7.8 Hz), 4.01 (2H, q, J=6.9 Hz), 6.91 (1H, d, J=2.0 Hz), 6.98 (1H, d, J=8.6 Hz), 7.11 (1H, d, J=2.0 Hz), 7.15 (2H, d, J=8.3 Hz), 7.48 (2H, d, J=8.3 Hz), 8.79 (2H, s), 10.82 (1H, s), 12.27 (1H, br s).

FABMS: 629 (M+H)$^+$.

The following paragraphs will describe exemplary processes based on solid phase synthesis.

Example 141

Preparation of 3-biphenyl-4-yl-2-{3-[(2,2-dimethylpropionyl)isobutylamino]-4-methoxyphenyl} propionic acid

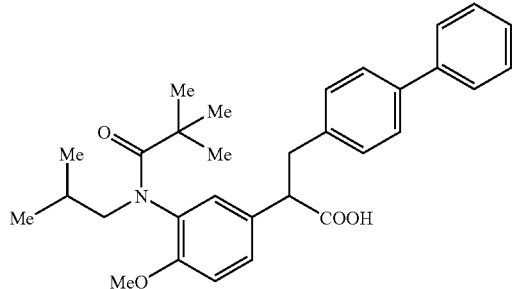

4-(hydroxymethyl)phenoxyacetic acid (10.0 g, 54.9 mmol) and allyl bromide (23.8 mL, 274 mmol) were dis solved in dimethylformamide (250 mL), the mixture was added with cesium carbonate (17.9 g, 54.9 mmol), and stirred at room temperature for 2.5 hours. The solid matter was removed by filtration, and the filtrate was evaporated under reduced pressure so as to remove the solvent, and the resultant residue was dissolved in ethyl acetate (250 mL). The solution was washed with a saturated brine, and dried over sodium sulfate. The solution was then evaporated under reduced pressure so as to remove the solvent, the resultant residue was dissolved in a mixed solvent of water:acetonitrile (v/v)=1:1, and the solution was lyophilized to thereby obtain 4-(hydroxymethyl)phenoxy acetic acid allyl ester (yield: 10.9 g, yield ratio: 89%) as a white powder.

3-(4-Bromophenyl)-2-(4-methoxy-3-nitrophenyl) propionic acid (5.00 g, 13.2 mmol), the 4-(hydroxymethyl)phenoxyacetic acid allyl ester (3.04 g, 13.7 mmol) and 4-dimethylaminopyridine (0.268 g, 2.19 mmol) were dissolved in dichloromethane (60 mL), and the mixture was gradually added with 1-ethyl-3-(3'-dimethylaminopropyl) carbodiimide hydrochloride (2.85 g, 13.8 mmol) over 5 minutes while keeping the temperature thereof at 0° C. The mixture was stirred at 0° C. for 4 hours, and further stirred at room temperature for 20 hours. The mixture was evaporated under reduced pressure so as to remove the solvent, and the resultant residue was added with a mixed solution of a 10 wt % aqueous citric acid solution (100 mL) and a saturated brine (100 mL), and the solution was extracted with ethyl acetate (180 mL). The organic phase was washed with the mixed solution of a 10 wt % aqueous citric acid solution (100 mL) and a saturated brine (100 mL) once again, and further washed twice with a mixed solution of an aqueous saturated sodium hydrogen carbonate solution (100 mL) and a saturated brine (100 mL), and finally washed twice with a saturated brine. The organic phase was dried over sodium sulfate, evaporated under reduced pressure so as to remove the solvent to thereby obtain 4-[3-(4-bromophenyl)-2-(4-methoxy-3-nitrophenyl)propionyloxymethyl]phenoxyacetic acid allyl ester (yield: 7.57 g, yield ratio: 98%).

Thus obtained 4-[3-(4-bromophenyl)-2-(4-methoxy-3-nitrophenyl)propionyloxymethyl]phenoxyacetic acid allyl ester (7.57 g, 13.0 mmol) was dissolved in dichloromethane (50 mL), the solution was successively added at 0° C. with tetrakis(triphenylphosphine) palladium (1.49 g, 1.29 mmol), triethylsilane (3.31 mL, 20.7 mmol) and acetic acid (2.3 mL, 40.1 mmol) in this order, and the mixture was stirred in a dark nitrogen atmosphere for 22 hours. The mixture was evaporated under reduced pressure so as to remove the solvent, the resultant residue was dissolved in ethyl acetate, and the obtained solution was filtered through Celite. The resultant ethyl acetate solution was washed with a saturated brine, dried over anhydrous sodium sulfate, evaporated under reduced pressure so as to remove the solvent, and the resultant residue was purified through silica gel column chromatography (dichloromethane:methanol:acetic acid (v/v)=98.5:1.2:0.3) to thereby obtain 4-[3-(4-bromo phenyl)-2-(4-methoxy-3-nitrophenyl)propionyloxymethyl]phenoxyacetic acid (yield: 6.01 g, yield ratio: 85%).

A trifluoroacetic acid salt of an aminomethylated support resin (product of Mimotopes, aminomethylated polystyrene-grafted D-Series SynPhase™ Lanterns, 35 µmol/bead, 280 beads) was added to a mixed solution of triethylamine, dimethylformamide and dichloromethane (5:19:76(v/v)), and allowed to stand at room temperature for 15 minutes. The reaction solution was discarded and the support resin was washed with dimethylformamide (200 mL×3). The support resin was further washed with dichloromethane (200 mL×3), and dried.

4-[3-(4-bromophenyl)-2-(4-methoxy-3-nitrophenyl)propionyloxymethyl]phenoxy acetic acid (6.01 g, 11.0 mmol) and 1-hydroxybenzotriazole (2.03 g, 13.2 mmol) were dissolved in a mixed solvent of dimethylformamide (22 mL) and dichloromethane (88 mL), and the mixture was added with diisopropylcarbodiimide (1.81 mL, 11.6 mmol). Five minutes later, the solution was added with above-obtained aminomethylated support resin (280 beads), and gently stirred at 25° C. for 24 hours. The reaction solution was discarded, and the support resin was washed with dimethylformamide (150 mL×2) and dichloromethane (150 mL×2), and dried. Being dissolved in a mixed solution (150 mL) of acetic anhydride, diisopropylethylamine and dimethylformamide (1:5:50 (v/v)), further added the above-obtained support, and the mixture was allowed to stand at room temperature for 90 minutes. The reaction solution was discarded, and the support resin was washed with dimethylformamide (150 mL×2) and dichloromethane (150 mL×2), and then dried, to thereby obtain a compound represented by formula (8) below. The amount of load was 7 µmol/bead. Res in the formula is such that defined in the above.

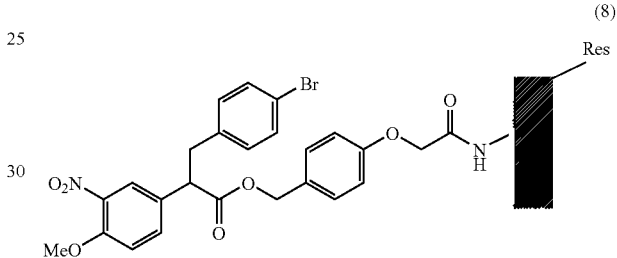

(8)

Tin chloride (I) dihydrate (45.1 g, 200 mmol) was dissolved in a mixed solution of dimethylformamide (50 mL) and dichloromethane (50 mL), the mixture was added with support resin (96 beads) comprising a compound represented by the formula (8), and allowed to stand at room temperature for 4 hours. The reaction solution was discarded and the support resin was washed with dimethylformamide (100 mL×2). A series of process steps were then repeated twice in which the support resin was added with a mixed solvent of water (20 mL) and tetrahydrofuran (80 mL), allowed to stand at 60° C. for 30 minutes, and the solvent was discarded. The support resin was washed twice with dichloromethane (100 mL×2), and then dried.

Sodium cyanotrihydroborate (1.07 g, 25 mmol) was dissolved in a mixed solvent of acetic acid (0.5 mL) and dimethylformamide (50 mL), and the mixture was added with isobutylaldehyde (4.54 mL, 50 mmol). The mixture was further added with the above-obtained support resin (48 beads), and allowed to stand at room temperature for 17 hours. The reaction solution was discarded, and the support resin was washed with dimethylformamide (50 mL×1). The support resin was then washed once with a mixed solvent of acetic acid (2.5 mL) and dimethylformamide (47.5 mL), and then once with a mixed solvent of ethyldiisopropylamine (2.5 mL) and dimethylformamide (47.5 mL). The support resin was still further washed with dimethylformamide (50 mL×1), finally with dichloromethane (50 mL×3), and then dried.

Pivaloyl chloride (0.92 mL, 7.5 mmol) was dissolved in a mixed solution of dimethylformamide (2.3 mL) and dichloromethane (9.2 mL), and the mixture was added with ethyldiisopropylamine (2.6 mL, 15 mmol). The mixture was further added with the above-obtained support resin (16 beads), and allowed to stand at room temperature for 17 hours. The reaction solution was discarded, and the support resin was washed with dimethylformamide (20 mL×3). The support resin was further washed with dichloromethane (20 mL×3), and then dried.

Tetrakis(triphenylphosphine) palladium (416 mg, 0.36 mmol) and phenylboric acid (122 mg, 1.0 mmol) were dissolved in a degassed dimethylformamide (8.0 mL), and the mixture was added with a 0.5 mol/L aqueous sodium carbonate solution (2 mL, 1.0 mmol) prepared using a degassed water. The mixture was further added with the above-obtained support resin (12 beads), and allowed to stand under an argon atmosphere at 80° C. for 17 hours. The reaction solution was discarded, and the support resin was washed with dimethylformamide (15 mL×3). The support resin was further washed three times with a solution prepared by dissolving sodium diethyldithiocarbamate (300 mg) and ethyldiisopropylamine (0.3 mL) in dimethylformamide (60 mL). The support resin was still further washed with dimethylformamide (15 mL×3), and finally with dichloromethane (15 mL×3), and then dried.

The above-obtained support resin (1 bead) was put in a mixed solvent of trifluoroacetic acid (0.16 mL) and dichloromethane (0.64 mL), and allowed to stand for 1 hour. The support resin was removed, and the solution was evaporated under reduced pressure, to thereby obtain 3-biphenyl-4-yl-2-{3-[(2,2-dimethylpropionyl)isobutylamino]-4-methoxyphenyl}propionic acid (yield: 1.7 mg, yield ratio: 50%). ESIMS measured values are listed in Table 20 below.

Compounds of Examples 142 to 332 were also prepared similarly to as described in Example 141. ESIMS measured values are listed in Table 20 below. Compounds exemplified in Examples 323 to 404 can also be prepared in a similar manner.

TABLE 20

| Example No. | R² | X | MS (M + H)⁺ |
|---|---|---|---|
| 141 | 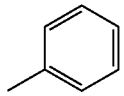 |  | 488 |
| 142 | 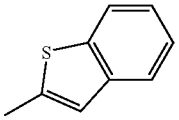 |  | 544 |
| 143 | 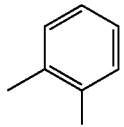 |  | 518 |

TABLE 20-continued

| Example No. | R² | X | MS (M + H)⁺ |
|---|---|---|---|
| 144 |  |  | 502 |
| 145 |  |  | 538 |
| 146 |  |  | 556 |
| 147 |  |  | 556 |
| 148 |  |  | 624 |
| 149 |  |  | 472 |
| 150 |  |  | 528 |
| 151 |  |  | 502 |
| 152 |  |  | 486 |
| 153 |  |  | 522 |

TABLE 20-continued

[Structure: Ar-CH(COOH)-CH2-C6H4-X with N(iBu)(C(O)R2) and OMe substituents]

| Example No. | R² | X | MS (M+H)⁺ |
|---|---|---|---|
| 154 | CH=CH-Me (propenyl) | 2-CF₃-phenyl | 540 |
| 155 | CH=CH-Me | 3,4-diCl-phenyl | 540 |
| 156 | CH=CH-Me | 3,5-bis(CF₃)-phenyl | 608 |
| 157 | CH₂-C(Me)=CH₂ (isobutenyl) | phenyl | 472 |
| 158 | CH₂-C(Me)=CH₂ | 2-benzothienyl | 528 |
| 159 | CH₂-C(Me)=CH₂ | 2-OMe-phenyl | 502 |
| 160 | CH₂-C(Me)=CH₂ | 4-Me-phenyl | 486 |
| 161 | CH₂-C(Me)=CH₂ | 2-naphthyl | 522 |
| 162 | CH₂-C(Me)=CH₂ | 2-CF₃-phenyl | 540 |
| 163 | CH₂-C(Me)=CH₂ | 3,4-diCl-phenyl | 540 |
| 164 | CH₂-C(Me)=CH₂ | 3,5-bis(CF₃)-phenyl | 608 |
| 165 | CH₂-CH(Me)-CH₂-Me (isobutyl-like) | phenyl | 502 |
| 166 | CH₂-CH(Me)-CH₂-Me | 2-benzothienyl | 558 |
| 167 | CH₂-CH(Me)-CH₂-Me | 2-OMe-phenyl | 532 |
| 168 | CH₂-CH(Me)-CH₂-Me | 4-Me-phenyl | 516 |
| 169 | CH₂-CH(Me)-CH₂-Me | 2-naphthyl | 552 |
| 170 | CH₂-CH(Me)-CH₂-Me | 2-CF₃-phenyl | 570 |
| 171 | CH₂-CH(Me)-CH₂-Me | 3,4-diCl-phenyl | 570 |

TABLE 20-continued

| Example No. | R² | X | MS (M + H)⁺ |
|---|---|---|---|
| 172 | CH(Me)CH₂Me (sec-butyl/isobutyl-like) | 3,5-(CF₃)₂-C₆H₃ | 638 |
| 173 | cyclopentyl | C₆H₅ | 500 |
| 174 | cyclopentyl | benzothiophen-2-yl | 556 |
| 175 | cyclopentyl | 2-OMe-C₆H₄ | 530 |
| 176 | cyclopentyl | 4-Me-C₆H₄ | 514 |
| 177 | cyclopentyl | 2-naphthyl | 550 |
| 178 | cyclopentyl | 2-CF₃-C₆H₄ | 568 |
| 179 | cyclopentyl | 3,4-Cl₂-C₆H₃ | 568 |
| 180 | cyclopentyl | 3,5-(CF₃)₂-C₆H₃ | 636 |
| 181 | phenyl | C₆H₅ | 508 |
| 182 | phenyl | benzothiophen-2-yl | 564 |
| 183 | phenyl | 2-OMe-C₆H₄ | 538 |
| 184 | phenyl | 4-Me-C₆H₄ | 522 |
| 185 | phenyl | 2-naphthyl | 558 |
| 186 | phenyl | 2-CF₃-C₆H₄ | 576 |
| 187 | phenyl | 3,4-Cl₂-C₆H₃ | 576 |
| 188 | phenyl | 3,5-(CF₃)₂-C₆H₃ | 644 |
| 189 | t-Bu | C₆H₅ | 502 |

TABLE 20-continued

| Example No. | R² | X | MS (M + H)⁺ |
|---|---|---|---|
| 190 | tBu (Me,Me,Me) | 2-methylbenzothiophene | 558 |
| 191 | tBu | 2-OMe-phenyl | 532 |
| 192 | tBu | 4-Me-phenyl | 516 |
| 193 | tBu | 6-methylnaphthyl | 552 |
| 194 | tBu | 2-CF₃-phenyl | 570 |
| 195 | tBu | 3,4-diCl-phenyl | 570 |
| 196 | tBu | 3,5-bis(CF₃)-phenyl | 638 |
| 197 | CH=CHMe | phenyl | 486 |
| 198 | CH=CHMe | 2-methylbenzothiophene | 542 |
| 199 | CH=CHMe | 2-OMe-phenyl | 516 |
| 200 | CH=CHMe | 4-Me-phenyl | 500 |
| 201 | CH=CHMe | 6-methylnaphthyl | 536 |
| 202 | CH=CHMe | 2-CF₃-phenyl | 554 |
| 203 | CH=CHMe | 3,4-diCl-phenyl | 553 |
| 204 | CH=CHMe | 3,5-bis(CF₃)-phenyl | 622 |
| 205 | C(=CH₂)Me | phenyl | 486 |
| 206 | C(=CH₂)Me | 2-methylbenzothiophene | 542 |
| 207 | C(=CH₂)Me | 2-OMe-phenyl | 516 |

TABLE 20-continued

Structure: common scaffold with N-isobutyl amide, methoxy group, and arylacetic acid (COOH) bearing para-X benzyl substituent.

| Example No. | R² | X | MS (M + H)⁺ |
|---|---|---|---|
| 208 | CH₂=C(Me)– | 4-Me-C₆H₄ | 500 |
| 209 | CH₂=C(Me)– | 2-naphthyl | 536 |
| 210 | CH₂=C(Me)– | 2-CF₃-C₆H₄-Me | 554 |
| 211 | CH₂=C(Me)– | 3,4-diCl-C₆H₃ | 554 |
| 212 | CH₂=C(Me)– | 3,5-bis(CF₃)-C₆H₃ | 622 |
| 213 | isobutyl (Me₂CHCH₂–) | C₆H₅ | 516 |
| 214 | isobutyl | 2-benzothienyl | 572 |
| 215 | isobutyl | 2-OMe-C₆H₄ | 546 |
| 216 | isobutyl | 4-Me-C₆H₄ | 530 |
| 217 | isobutyl | 2-naphthyl | 566 |
| 218 | isobutyl | 2-CF₃-C₆H₄-Me | 584 |
| 219 | isobutyl | 3,4-diCl-C₆H₃ | 584 |
| 220 | isobutyl | 3,5-bis(CF₃)-C₆H₃ | 652 |
| 221 | cyclopentyl | C₆H₅ | 514 |
| 222 | cyclopentyl | 2-benzothienyl | 570 |
| 223 | cyclopentyl | 2-OMe-C₆H₄ | 544 |
| 224 | cyclopentyl | 4-Me-C₆H₄ | 528 |
| 225 | cyclopentyl | 2-naphthyl | 564 |

TABLE 20-continued

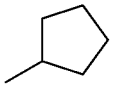

| Example No. | R² | X | MS (M + H)⁺ |
|---|---|---|---|
| 226 | cyclopentyl | 2-CF₃-phenyl | 582 |
| 227 | cyclopentyl | 3,4-diCl-phenyl | 582 |
| 228 | cyclopentyl | 3,5-di(CF₃)-phenyl | 650 |
| 229 | phenyl | phenyl | 522 |
| 230 | phenyl | benzothiophen-2-yl | 578 |
| 231 | phenyl | 2-OMe-phenyl | 552 |
| 232 | phenyl | 4-Me-phenyl | 536 |
| 233 | phenyl | naphth-2-yl | 572 |
| 234 | phenyl | 2-CF₃-phenyl | 590 |

TABLE 20-continued

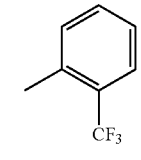

| Example No. | R² | X | MS (M + H)⁺ |
|---|---|---|---|
| 235 | phenyl | 3,4-diCl-phenyl | 590 |
| 236 | phenyl | 3,5-di(CF₃)-phenyl | 658 |
| 237 | tert-butyl | 3,5-diCl-phenyl | 556 |
| 238 | tert-butyl | 2-CN-phenyl | 513 |
| 239 | tert-butyl | 2,5-diMe-thiophen-yl | 508 |
| 240 | tert-butyl | 2-Me-phenyl | 502 |
| 241 | tert-butyl | benzofuran-2-yl | 528 |
| 242 | tert-butyl | 4-tert-butyl-phenyl | 544 |

TABLE 20-continued

| Example No. | R² | X | MS (M + H)⁺ |
|---|---|---|---|
| 243 | *t*-Bu (Me₃C) | 4-MeO-3-Me-C₆H₃-Cl | 552 |
| 244 | *t*-Bu (Me₃C) | 4-Me-C₆H₄-OH (benzyl alcohol) | 518 |
| 245 | CH=CH-Me (propenyl) | 3,5-diCl-C₆H₃-Me | 540 |
| 246 | CH=CH-Me | 2-Me-C₆H₄-CN | 497 |
| 247 | CH=CH-Me | 2,5-diMe-thiophene | 492 |
| 248 | CH=CH-Me | 2,3-diMe-C₆H₃ | 486 |
| 249 | CH=CH-Me | 2-Me-benzofuran | 512 |
| 250 | CH=CH-Me | 4-Me-C₆H₄-C(Me)₃ (cumyl) | 528 |

TABLE 20-continued

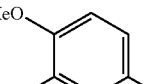

| Example No. | R² | X | MS (M + H)⁺ |
|---|---|---|---|
| 251 | CH=CH-Me | 4-MeO-3-Me-C₆H₃-Cl | 536 |
| 252 | CH=CH-Me | 4-Me-C₆H₄-OH | 502 |
| 253 | C(=CH₂)Me (isopropenyl) | 3,5-diCl-C₆H₃-Me | 540 |
| 254 | C(=CH₂)Me | 2-Me-C₆H₄-CN | 497 |
| 255 | C(=CH₂)Me | 2,5-diMe-thiophene | 492 |
| 256 | C(=CH₂)Me | 2,3-diMe-C₆H₃ | 486 |
| 257 | C(=CH₂)Me | 2-Me-benzofuran | 512 |
| 258 | C(=CH₂)Me | 4-Me-C₆H₄-C(Me)₃ | 528 |

TABLE 20-continued

| Example No. | R² | X | MS (M + H)⁺ |
|---|---|---|---|
| 259 | CH₂=C(Me)- | 4-MeO-3-Me-C₆H₃-Cl | 536 |
| 260 | CH₂=C(Me)- | 4-Me-C₆H₄-CH₂OH | 502 |
| 261 | isobutyl (Me₂CHCH₂) | 3,5-diCl-C₆H₃-Me | 570 |
| 262 | isobutyl | 2-CN-C₆H₄-Me | 527 |
| 263 | isobutyl | 2,5-diMe-thiophene | 522 |
| 264 | isobutyl | 2-Me-C₆H₄-Me | 516 |
| 265 | isobutyl | 2-Me-benzofuran | 542 |
| 266 | isobutyl | 4-Me-C₆H₄-C(Me)₃ | 558 |

| Example No. | R² | X | MS (M + H)⁺ |
|---|---|---|---|
| 267 | isopentyl | 4-MeO-3-Me-C₆H₃-Cl | 566 |
| 268 | isopentyl | 4-Me-C₆H₄-CH₂OH | 532 |
| 269 | cyclopentyl | 3,5-diCl-C₆H₃-Me | 568 |
| 270 | cyclopentyl | 2-CN-C₆H₄-Me | 525 |
| 271 | cyclopentyl | 2,5-diMe-thiophene | 520 |
| 272 | cyclopentyl | 2-Me-C₆H₄-Me | 514 |
| 273 | cyclopentyl | 2-Me-benzofuran | 540 |
| 274 | cyclopentyl | 4-Me-C₆H₄-C(Me)₃ | 556 |

TABLE 20-continued
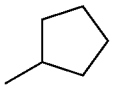
| Example No. | R² | X | MS (M + H)⁺ |
|---|---|---|---|
| 275 | 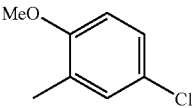 | 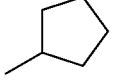 | 564 |
| 276 | 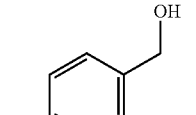 | 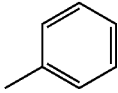 | 530 |
| 277 | 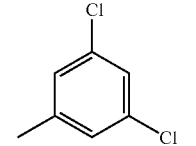 | 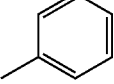 | 576 |
| 278 | 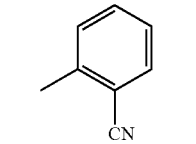 | 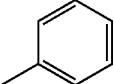 | 533 |
| 279 | 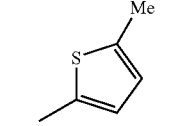 | 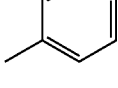 | 528 |
| 280 | 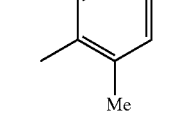 | 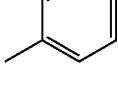 | 522 |
| 281 | 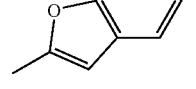 | 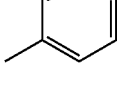 | 548 |
| 282 | 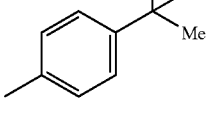 | 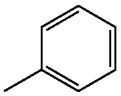 | 564 |
TABLE 20-continued
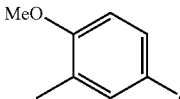
| Example No. | R² | X | MS (M + H)⁺ |
|---|---|---|---|
| 283 | 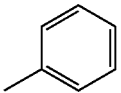 | 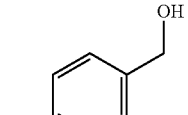 | 572 |
| 284 | 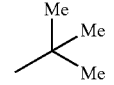 | 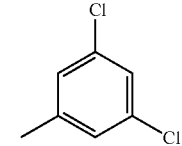 | 538 |
| 285 | 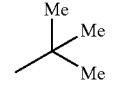 | 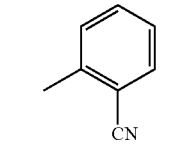 | 570 |
| 286 | 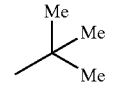 | 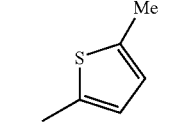 | 527 |
| 287 | 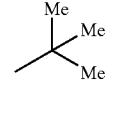 | 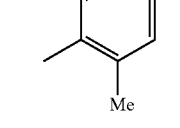 | 522 |
| 288 | 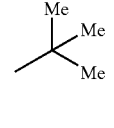 | 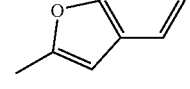 | 516 |
| 289 | 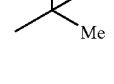 | 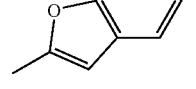 | 542 |
| 290 | 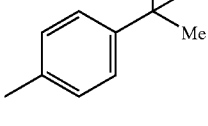 | 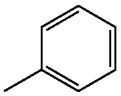 | 558 |

TABLE 20-continued

| Example No. | R² | X | MS (M + H)⁺ |
|---|---|---|---|
| 291 | tBu (Me,Me,Me) | 4-MeO-3-Me-phenyl-Cl | 566 |
| 292 | tBu (Me,Me,Me) | 4-Me-phenyl-OH | 532 |
| 293 | CH=CHMe | 3,5-diCl-phenyl | 554 |
| 294 | CH=CHMe | 2-CN-phenyl | 511 |
| 295 | CH=CHMe | 2,5-diMe-thienyl | 506 |
| 296 | CH=CHMe | 2,3-diMe-phenyl | 500 |
| 297 | CH=CHMe | benzofuran-2-yl | 526 |
| 298 | CH=CHMe | 4-(CMe₃)-phenyl | 542 |

TABLE 20-continued

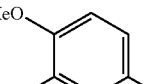

| Example No. | R² | X | MS (M + H)⁺ |
|---|---|---|---|
| 299 | CH=CHMe | 4-MeO-3-Me-phenyl-Cl | 550 |
| 300 | CH=CHMe | 4-Me-phenyl-OH | 516 |
| 301 | C(=CH₂)Me | 3,5-diCl-phenyl | 554 |
| 302 | C(=CH₂)Me | 2-CN-phenyl | 511 |
| 303 | C(=CH₂)Me | 2,5-diMe-thienyl | 506 |
| 304 | C(=CH₂)Me | 2,3-diMe-phenyl | 500 |
| 305 | C(=CH₂)Me | benzofuran-2-yl | 526 |
| 306 | C(=CH₂)Me | 4-(CMe₃)-phenyl | 542 |

TABLE 20-continued

| Example No. | R² | X | MS (M + H)⁺ |
|---|---|---|---|
| 307 | CH₂=C(Me)– | 4-MeO, 3-Me, 5-Cl phenyl | 550 |
| 308 | CH₂=C(Me)– | 4-(CH₂OH), 3-Me phenyl | 516 |
| 309 | isobutyl (Me₂CHCH₂–) | 3,5-diCl, 4-Me phenyl | 584 |
| 310 | isobutyl | 2-CN, 4-Me phenyl | 541 |
| 311 | isobutyl | 2,5-diMe thiophene | 536 |
| 312 | isobutyl | 2,4-diMe phenyl | 530 |
| 313 | isobutyl | 2-Me benzofuran | 556 |
| 314 | isobutyl | 4-(CMe₃), 3-Me phenyl | 572 |
| 315 | isobutyl | 4-MeO, 3-Me, 5-Cl phenyl | 580 |
| 316 | isobutyl | 4-(CH₂OH), 3-Me phenyl | 546 |
| 317 | cyclopentyl | 3,5-diCl, 4-Me phenyl | 582 |
| 318 | cyclopentyl | 2-CN, 4-Me phenyl | 539 |
| 319 | cyclopentyl | 2,5-diMe thiophene | 534 |
| 320 | cyclopentyl | 2,4-diMe phenyl | 528 |
| 321 | cyclopentyl | 2-Me benzofuran | 554 |
| 322 | cyclopentyl | 4-(CMe₃), 3-Me phenyl | 570 |

TABLE 20-continued
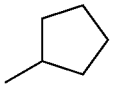
| Example No. | R² | X | MS (M + H)⁺ |
|---|---|---|---|
| 323 | 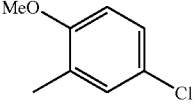 | 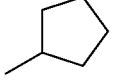 | 578 |
| 324 | 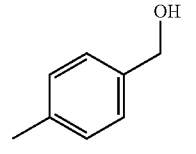 | 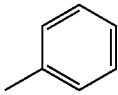 | 544 |
| 325 | 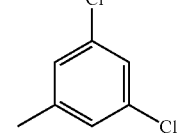 | 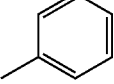 | 590 |
| 326 | 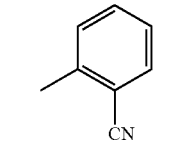 | 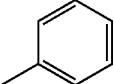 | 547 |
| 327 | 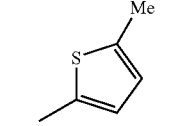 | 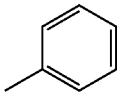 | 542 |
| 328 | 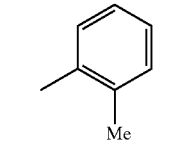 | 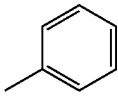 | 536 |
| 329 | 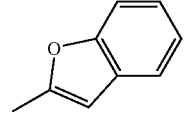 | 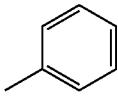 | 562 |
| 330 | 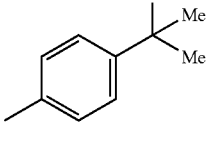 | 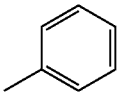 | 578 |
| 331 | 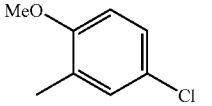 | 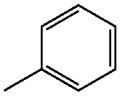 | 586 |
| 332 | 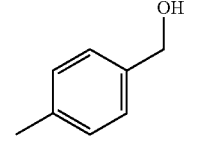 | 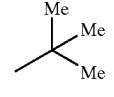 | 552 |
| 333 | 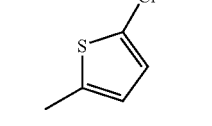 | 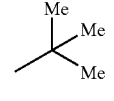 | |
| 334 | 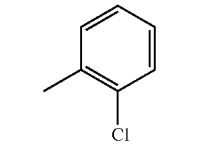 | 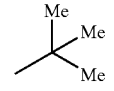 | |
| 335 | 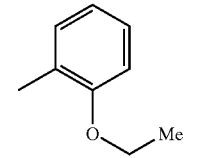 | 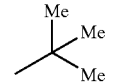 | |
| 336 | 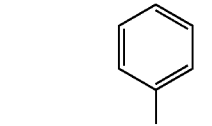 | 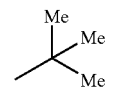 | |
| 337 | 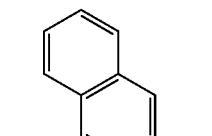 | | |

TABLE 20-continued
| Example No. | R² | X | MS (M + H)⁺ |
|---|---|---|---|
| 338 | 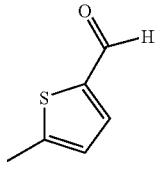 | 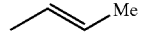 | |
| 339 | 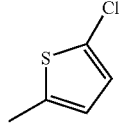 | 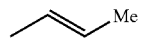 | |
| 340 | 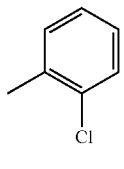 | 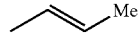 | |
| 341 | 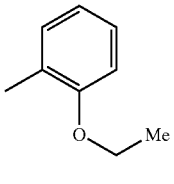 | 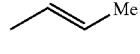 | |
| 342 | 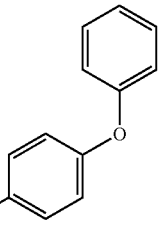 | 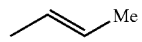 | |
| 343 | 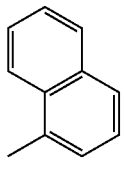 | 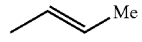 | |
| 344 | 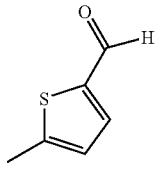 | 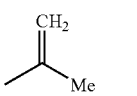 | |
TABLE 20-continued
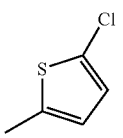
| Example No. | R² | X | MS (M + H)⁺ |
|---|---|---|---|
| 345 | 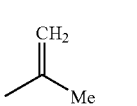 | 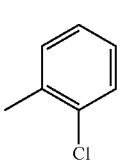 | |
| 346 | 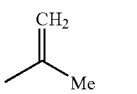 | 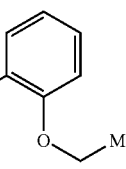 | |
| 347 | 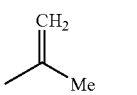 | 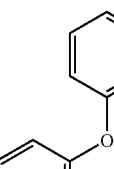 | |
| 348 |  | 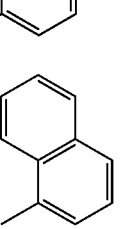 | |
| 349 | 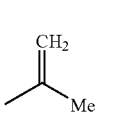 | 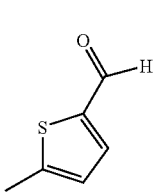 | |
| 350 | 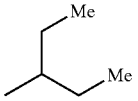 | | |
| 351 | 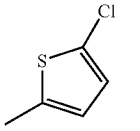 | | |

TABLE 20-continued
| Example No. | R² | X | MS (M + H)⁺ |
|---|---|---|---|
| 352 | 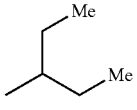 | 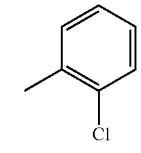 | |
| 353 | 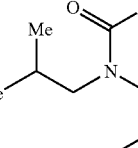 | 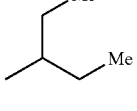 | |
| 354 | 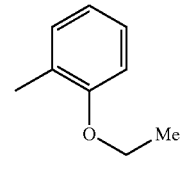 | 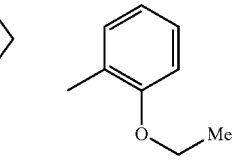 | |
| 355 | 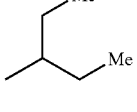 | 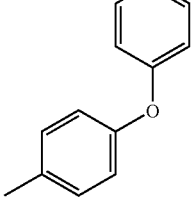 | |
| 356 | 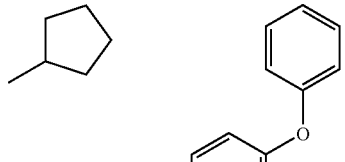 | 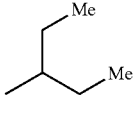 | |
| 357 | 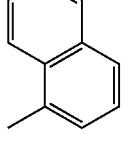 | 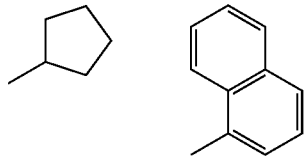 | |
| 358 | 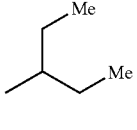 | 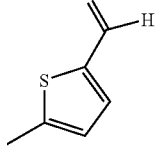 | |
| 359 | 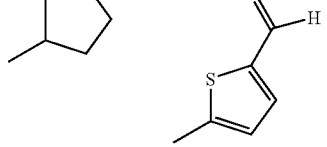 | 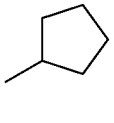 | |
| 360 | 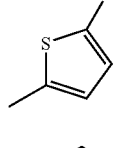 | 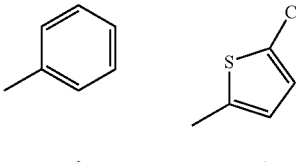 | |
| 361 | 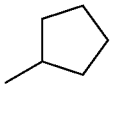 | 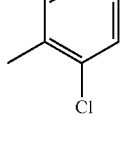 | |
| 362 | 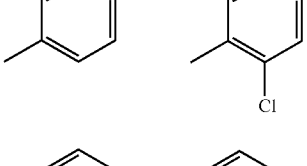 | 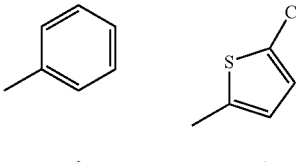 | |
| 363 | 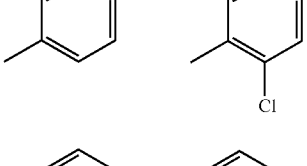 | 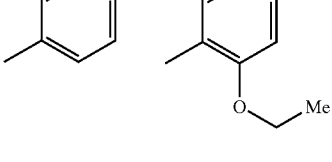 | |
| 364 | 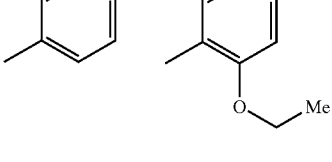 | 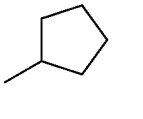 | |
| 365 | 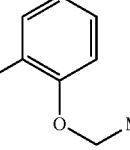 | 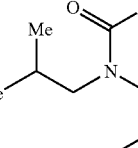 | |

TABLE 20-continued

| Example No. | R² | X | MS (M + H)⁺ |
|---|---|---|---|
| 366 | phenyl | 4-phenoxyphenyl | |
| 367 | phenyl | naphthalen-1-yl | |
| 368 | phenyl | 5-methylthiophene-2-carbaldehyde | |
| 369 | tert-butyl | 5-chlorothiophen-2-yl | |
| 370 | tert-butyl | 2-chlorophenyl | |
| 371 | tert-butyl | 2-ethoxyphenyl | |
| 372 | tert-butyl | 4-phenoxyphenyl | |
| 373 | tert-butyl | naphthalen-1-yl | |
| 374 | tert-butyl | 5-methylthiophene-2-carbaldehyde | |
| 375 | 1-propenyl | 5-chlorothiophen-2-yl | |
| 376 | 1-propenyl | 2-chlorophenyl | |
| 377 | 1-propenyl | 2-ethoxyphenyl | |
| 378 | 1-propenyl | 4-phenoxyphenyl | |
| 379 | 1-propenyl | naphthalen-1-yl | |

TABLE 20-continued
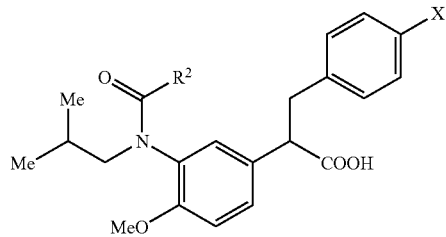
| Example No. | R² | X | MS (M + H)⁺ |
|---|---|---|---|
| 380 | | | |
| 381 | | | |
| 382 | | | |
| 383 | | | |
| 384 | | | |
| 385 | | | |
| 386 | | | |
TABLE 20-continued
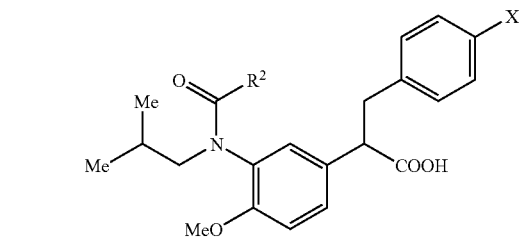
| Example No. | R² | X | MS (M + H)⁺ |
|---|---|---|---|
| 387 | | | |
| 388 | | | |
| 389 | | | |
| 390 | | | |
| 391 | | | |
| 392 | | | |
| 393 | | | |

TABLE 20-continued
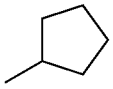
| Example No. | R² | X | MS (M + H)⁺ |
|---|---|---|---|
| 394 | 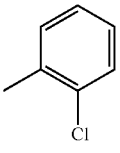 | 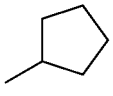 | |
| 395 | 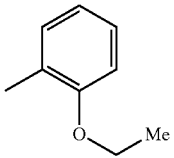 | 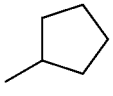 | |
| 396 | 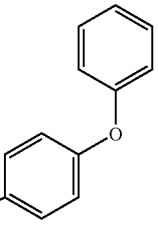 | 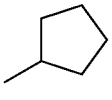 | |
| 397 | 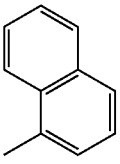 | 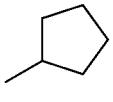 | |
| 398 | 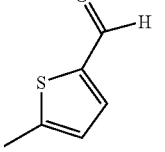 | 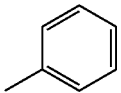 | |
| 399 | 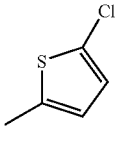 | 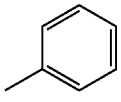 | |
| 400 | 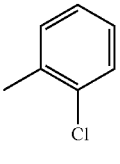 | 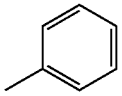 | |
| 401 | 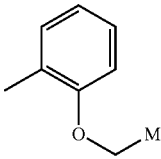 | 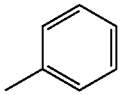 | |
| 402 | 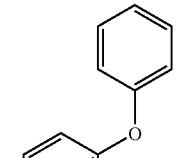 | 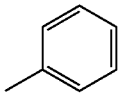 | |
| 403 | 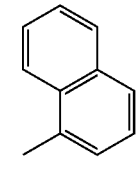 | 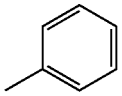 | |
| 404 | | 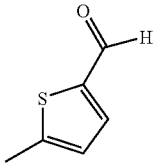 | |
Example 405
Preparation of 2-{3-[(2,2-dimethylpropionyl) isobutylamino]-4-methoxyphenyl}-3-[4-(3-methylbut-2-enoylamino)phenyl]propionic acid
2-(3-amino-4-methoxyphenyl)-3-(4-nitrophenyl) propionic acid (6.20 g, 19.6 mmol) was dissolved in a mixed solvent of acetone (50 mL) and water (50 mL), and was gradually added with an acetone solution (50 mL) of 9-fluorenylmethyl chloroformate (5.08 g, 19.6 mmol) over 30 minutes in a drop-wise manner at 0° C. The mixture was heated to room temperature, and further stirred for 3 hours. The mixture was then added with dichloromethane (200 mL) and water (300 mL). The separated aqueous phase was extracted with dichloromethane (150 mL) three times. The extracts were mixed with the first organic phase, and washed twice with a saturated brine (150 mL). The organic phase was dried over sodium sulfate, evaporated under reduced pressure so as to remove the solvent, to thereby obtain N-fluoronylmethoxy carbonyl-2-(3-amino-4-methoxyphenyl)-3-(4-nitrophenyl) propionic acid (yield: 10.3 g, yield ratio: 97%).

A compound represented by formula (9) below was obtained similarly to as described in Example 141. The amount of load was found to be 16.8 μmol/bead. Res in the formula is such that defined in the above.

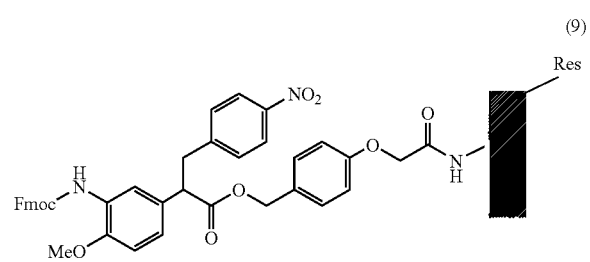

(9)

The compound represented by the formula (9) (96 beads) were added to a mixed solvent of piperidine (20 mL) and dimethylformamide (80 mL), and allowed to stand for 40 minutes. The reaction solution was discarded, and the support resin was washed with dimethylformamide (100 mL×3). The support resin was further washed with dichloromethane (100 mL×3), and then dried.

Sodium cyanotrihydroborate (1.07 g, 25 mmol) was dissolved in a mixed solvent of acetic acid (0.5 mL) and dimethylformamide (50 mL), and the mixture was added with isobutylaldehyde (4.54 mL, 50 mmol). The mixture was further added with the above-obtained support resin (48 beads), and allowed to stand at room temperature for 17 hours. The reaction solution was discarded, and the support resin was washed with dimethylformamide (50 mL×1). The support resin was then washed once with a mixed solution of acetic acid (2.5 mL) and dimethylformamide (47.5 mL), and further washed once with a mixed solvent of ethyldiisopropylamine (2.5 mL) and dimethylformamide (47.5 mL). The support resin was still further washed with dimethyl formamide (50 mL×1), and finally with dichloromethane (50 mL×3), and then dried.

Pivaloyl chloride (1.2 mL, 10 mmol) was dissolved in a mixed solvent of dimethylformamide (3.2 mL) and dichloromethane (12.8 mL), and the mixture was added with ethyldiisopropylamine (3.5 mL, 20 mmol). The mixture was further added with above-obtained support resin (24 beads), and allowed to stand at room temperature for 17 hours. The reaction solution was discarded, and the support resin was washed with dimethylformamide (20 mL×3). A series of process steps were then repeated three times in which the support resin was added with methanol (20 mL), allowed standing at 60° C. for 30 minutes, and the solvent was discarded. The support resin was finally washed with dichloromethane (20 mL×3), and then dried.

Tin chloride (I) dihydrate (45.1 g, 200 mmol) was dissolved in a mixed solvent of dimethylformamide (50 mL) and dichloromethane (50 mL), the mixture was added with support resin (96 beads) and allowed to stand at room temperature for 4 hours. The reaction solution was discarded, the support resin was washed with dimethylformamide (100 mL×2). A series of process steps were then repeated twice in which the support resin was added with a mixed solvent of water (20 mL) and tetrahydrofuran (80 mL), allowed to stand at 60° C. for 30 minutes, and the solvent was discarded. The support resin was finally washed with dichloromethane (20 mL×2), and then dried.

3-methylbut-2-enoyl chloride (0.45 mL, 4 mmol) was dissolved in a mixed solvent of dimethylformamide (1.3 mL) and dichloromethane (5.2 mL), and the mixture was added with ethyldiisopropylamine (1.4 mL, 8 mmol). The mixture was further added with above-obtained support resin (8 beads), and allowed to stand at room temperature for 17 hours. The reaction solution was discarded, and the support resin was washed with dimethylformamide (10 mL×3). The support resin was further washed with dichloromethane (100 mL×3) and then dried.

The above-obtained support resin (1 bead) was put in trifluoroacetic acid (0.8 mL), and allowed to stand for 1 hour. The support resin was removed, and the solvent was evaporated to thereby obtain 2-{3-[(2,2-dimethyl propionyl)isobutylamino]-4-methoxyphenyl}-3-[4-(3-methylbut-2-enoylamino)phenyl]propionic acid (yield: 6 mg, yield ratio: 70%). ESIMS measured values are listed in Table 21 below.

Compounds of Examples 406 to 498 were also prepared similarly to as described in Example 405. ESIMS measured values are listed in Table 21 below.

TABLE 21

| Example No. | R⁵ | MS (M + H)⁺ |
|---|---|---|
| 405 | Me-CH=C(Me)- | 509 |
| 406 | cyclohexyl | 537 |
| 407 | Me₂CHCH₂CH(Me)- | 553 |
| 408 | Me(CH₂)₇- | 595 |

TABLE 21-continued
| Example No. | R⁵ | MS (M + H)⁺ |
|---|---|---|
| 409 | 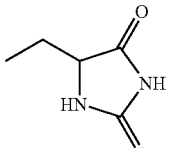 | 567 |
| 410 | 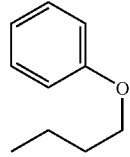 | 589 |
| 411 | 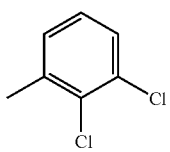 | 599 |
| 412 | 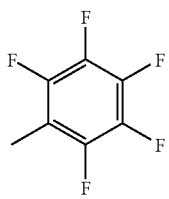 | 621 |
| 413 | 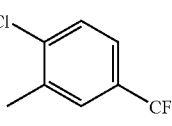 | 633 |
| 414 | 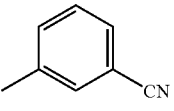 | 556 |
| 415 | 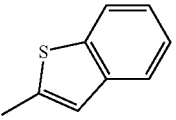 | 587 |
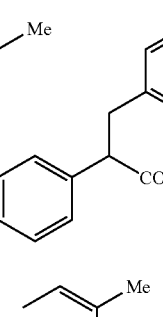
| Example No. | R⁵ | MS (M + H)⁺ |
|---|---|---|
| 416 | 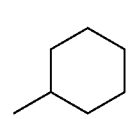 | 493 |
| 417 | 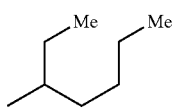 | 521 |
TABLE 21-continued
| Example No. | R⁵ | MS (M + H)⁺ |
|---|---|---|
| 418 | 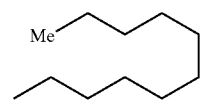 | 537 |
| 419 | 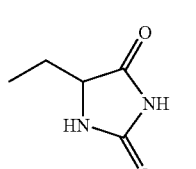 | 579 |
| 420 | 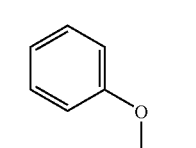 | 551 |
| 421 | 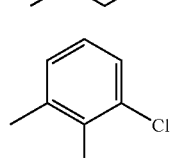 | 573 |
| 422 | 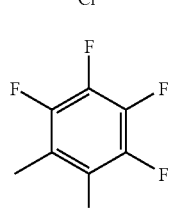 | 583 |
| 423 | 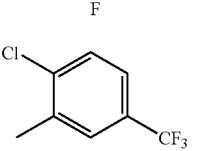 | 605 |
| 424 | 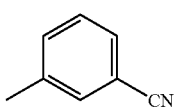 | 617 |
| 425 | 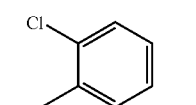 | 540 |
| 426 | | 583 |
| 427 | 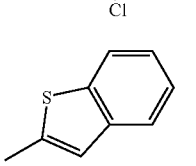 | 571 |

TABLE 21-continued
| Example No. | R⁵ | MS (M + H)⁺ |
|---|---|---|
| | 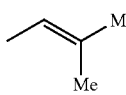 | |
| 428 | 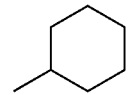 | 523 |
| 429 | 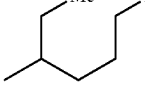 | 551 |
| 430 | 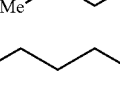 | 567 |
| 431 | 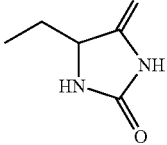 | 609 |
| 432 | 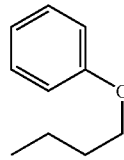 | 581 |
| 433 | 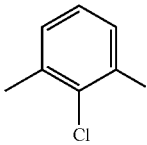 | 603 |
| 434 | 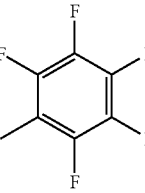 | 613 |
| 435 | 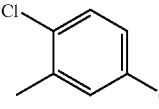 | 635 |
| 436 | 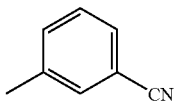 | 647 |
TABLE 21-continued
| Example No. | R⁵ | MS (M + H)⁺ |
|---|---|---|
| 437 | 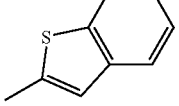 | 570 |
| 438 | 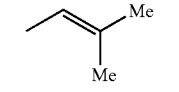 | 601 |
| | 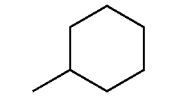 | |
| 439 | 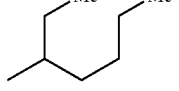 | 529 |
| 440 | 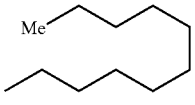 | 557 |
| 441 | 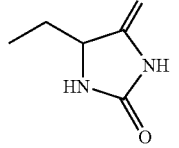 | 573 |
| 442 | 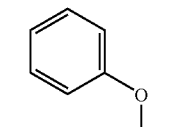 | 615 |
| 443 | 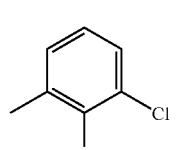 | 587 |
| 444 | | 609 |
| 445 | | 619 |

TABLE 21-continued
| Example No. | R⁵ | MS (M + H)⁺ |
|---|---|---|
| 446 | 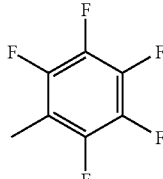 | 641 |
| 447 | 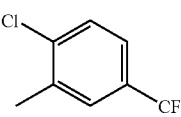 | 653 |
| 448 | 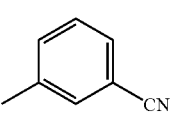 | 576 |
| 449 | 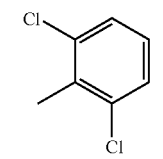 | 619 |
| 450 | 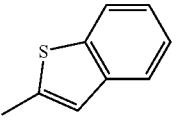 | 607 |
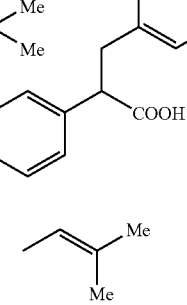
| Example No. | R⁵ | MS (M + H)⁺ |
|---|---|---|
| 451 | 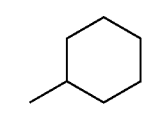 | 523 |
| 452 | 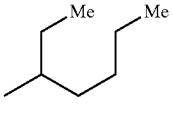 | 551 |
| 453 | 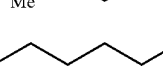 | 567 |
| 454 | 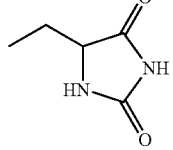 | 609 |
TABLE 21-continued
| Example No. | R⁵ | MS (M + H)⁺ |
|---|---|---|
| 455 | 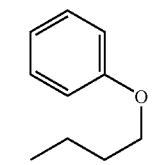 | 581 |
| 456 | 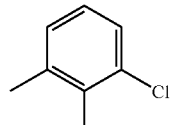 | 603 |
| 457 | 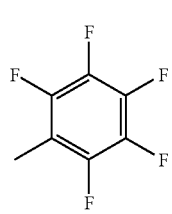 | 613 |
| 458 | 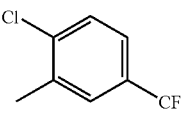 | 635 |
| 459 | 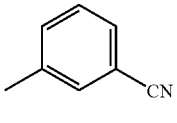 | 647 |
| 460 | 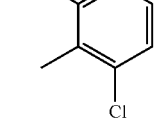 | 570 |
| 461 | 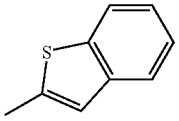 | 613 |
| 462 | 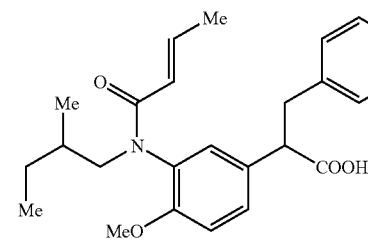 | 601 |

TABLE 21-continued

| Example No. | R⁵ | MS (M + H)⁺ |
|---|---|---|
| 463 | CMe=CHMe (Me,Me substituted alkene) | 507 |
| 464 | cyclohexyl-CH₂ | 535 |
| 465 | (Me)CH-CH₂-CH₂-CH(Me)-CH₂ branched | 551 |
| 466 | Me-(CH₂)₉- | 593 |
| 467 | 5-ethyl-hydantoin-yl | 565 |
| 468 | 4-butoxyphenyl | 587 |
| 469 | 2,3-dichloro-6-methylphenyl | 597 |
| 470 | pentafluorophenyl-CH₂ | 619 |
| 471 | 4-chloro-3-methyl-...-CF₃ phenyl | 631 |
| 472 | 3-cyanophenyl | 554 |
| 473 | 2,6-dichloro-3-methylphenyl | 597 |

General structure (Table 21):

Compound with 4-methoxyphenyl core bearing –CH(COOH)– and an N-(2-methylbutyl)-N-(2-ethylbutanoyl)amino substituent, linked via –CH₂– to a 4-(R⁵–C(O)NH–)phenyl group.

| Example No. | R⁵ | MS (M + H)⁺ |
|---|---|---|
| 474 | 2-methyl-benzothiophen-3-yl | 585 |
| 475 | CMe=CHMe | 537 |
| 476 | cyclohexyl-CH₂ | 565 |
| 477 | (Me)CH-CH₂-CH₂-CH(Me)-CH₂ branched | 581 |
| 478 | Me-(CH₂)₉- | 623 |
| 479 | 5-ethyl-hydantoin-yl | 595 |
| 480 | 4-butoxyphenyl | 617 |
| 481 | 2,3-dichloro-6-methylphenyl | 627 |

TABLE 21-continued
| Example No. | R⁵ | MS (M + H)⁺ |
|---|---|---|
| 482 | 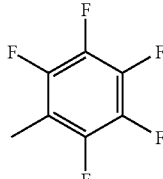 | 649 |
| 483 | 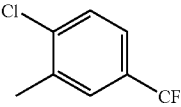 | 661 |
| 484 | 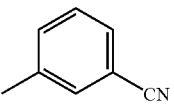 | 584 |
| 485 | 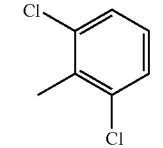 | 627 |
| 486 | 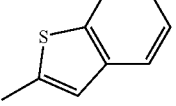 | 615 |
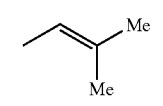
| Example No. | R⁵ | MS (M + H)⁺ |
|---|---|---|
| 487 | 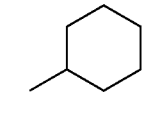 | 543 |
| 488 | 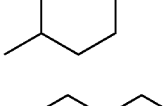 | 571 |
| 489 | 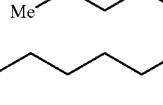 | 587 |
| 490 | 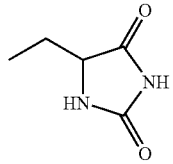 | 629 |
TABLE 21-continued
| Example No. | R⁵ | MS (M + H)⁺ |
|---|---|---|
| 491 | 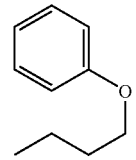 | 601 |
| 492 | 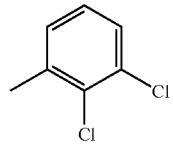 | 623 |
| 493 | 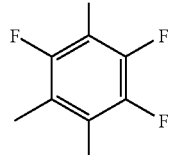 | 633 |
| 494 | 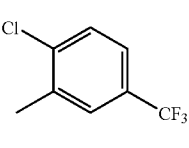 | 655 |
| 495 | 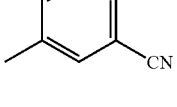 | 667 |
| 496 | 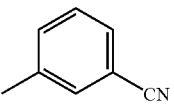 | 590 |
| 497 | 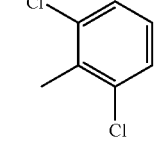 | 633 |
| 498 | 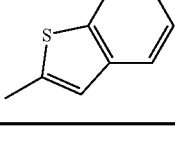 | 621 |

Example 499

Preparation of 3-[4-(2,6-dichlorobenzoyl amino) phenyl]-2(S)-{3-[(2,2-dimethylpropionyl)isobutyl amino]-4-methoxyphenyl}propionic acid

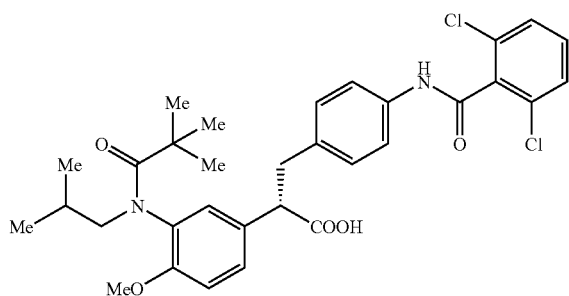

To a mixed solution of a tetrahydrofuran (120 mL) solution of 4-methoxy-3-nitrophenylacetic acid ethyl ester (24.6 g, 100 mmol) and methanol (120 mL), a 2 mol/L aqueous sodium hydroxide solution (60 mL) was added and stirred for 2 hours. After the reaction, the solvent was concentrated under reduced pressure. The resultant residue was washed with ether (300 mL), and the aqueous phase was adjusted to be acidic using a 1 mol/L aqueous hydrochloric acid solution (100 mL), extracted with ethyl acetate (300 mL×2), and dried over anhydrous magnesium sulfate. The dried solution was filtered, and the filtrate was concentrated under reduced pressure to thereby obtain 4-methoxy-3-nitrophenylacetic acid (yield: 20.6 g, yield ratio: 95%).

A 1,2-dichloroethane solution (100 mL) of thus obtained 4-methoxy-3-nitrophenylacetic acid (5.0 g, 23.7 mmol) was added with oxalyl chloride (4.4 mL, 47.4 mmol) and N,N-dimethylformamide (1 mL) at room temperature, and the mixture was stirred for 2 hour. After the reaction, the solvent was concentrated under reduced pressure, to thereby obtain acid chloride (5.2 g). Next a tetrahydrofuran solution (50 mL) of (S)-4-benzyl-2-oxazolidinone (5.0 g, 29 mmol) was gradually added with a 1.6 mol/L n-butyl lithium solution (18.0 mL, 28.2 mmol) at −78° C., and the mixture was stirred for 2 hours. Next the reaction solution was gradually added with a tetrahydrofuran solution (30 mL) of the above-synthesized acid chloride in a drop-wise manner, and the mixture was stirred for 1 hour. After the reaction, the solution was added with a saturated aqueous ammonium chloride solution (100 mL), extracted with ethyl acetate (200 mL), and the organic phase was washed with a saturated brine (100 mL), and dried over anhydrous magnesium sulfate. The dried organic phase was filtered, the filtrate was concentrated under reduced pressure, and the resultant residue was purified through silica gel column chromatography (n-hexane:ethyl acetate (v/v)=3:2) to thereby obtain 4(S)-benzyl-3-[2-(4-methoxy-3-nitro phenyl)acetyl]oxazolidine-2-one (yield: 6.7 g, yield ratio: 77%).

A mixed solution of ethyl acetate (60 mL)-methanol (60 mL) of 4(S)-benzyl-3-[2-(4-methoxy-3-nitrophenyl)acetyl] oxazolidine-2-one (6.7 g, 18 mmol) was added with 10 wt % of palladium/carbon (0.67 g) and isobutylaldehyde (2.1 mL, 23.5 mmol), and the mixture was stirred under a hydrogen atmosphere (4 kg/cm²) for 12 hours. After the reaction, any insoluble matter was removed by filtration through Celite, the filtrate was concentrated under reduced pressure, and the resultant residue was purified through silica gel column chromatography (n-hexane:ethyl acetate (v/v)=4:1) to thereby obtain 4(S)-benzyl-3-[2-(3-isobutylamino-4-methoxyphenyl)acetyl]oxazolidine-2-one (yield: 7.1 g, yield ratio: 99%).

A 1,2-dichloroethane solution (120 mL) of thus obtained 4(S)-benzyl-3-[2-(3-isobutylamino-4-methoxy phenyl) acetyl]oxazolidine-2-one (7.1 g, 18 mmol) was added with trimethylacetyl chloride (3.3 mL, 27 mmol) and triethylamine (2.0 mL, 36 mmol) at 0° C., and the mixture was stirred at room temperature for 3 hours. After the reaction, the solvent was concentrated under reduced pressure, and the resultant residue was added with ethyl acetate (200 mL), the solution was successively washed with an aqueous saturated sodium hydrogen carbonate solution (100 mL), an aqueous 1N-hydrochloric acid solution (100 mL) and a saturated brine (100 mL), and the organic phase was dried over anhydrous magnesium sulfate. The dried organic phase was filtered, the filtrate was concentrated under reduced pressure, and the resultant residue was purified through silica gel column chromatography (n-hexane:ethyl acetate (v/v)=3:1) to thereby obtain N-{5-[2-(4(S)-benzyl-2-oxooxazolidine-3-yl)-2-oxoethyl]-2-methoxyphenyl}-N-isobutyl-2,2-dimethylpropionic acid amide (yield: 8.1 g, yield ratio: 94%).

A tetrahydrofuran solution (80 mL) of thus obtained N-{5-[2-(4(S)-benzyl-2-oxooxazolidine-3-yl)-2-oxoethyl]-2-methoxyphenyl}-N-isobutyl-2,2-dimethylpropionic acid amide (7.9 g, 16.5 mmol) was gradually added with a tetrahydrofuran solution (18 mL, 18 mmol) of an 1 mol/L lithium bis(trimethylsilyl)amide in a step-wise manner at −78° C., and the mixture was stirred for 2 hours. Next a tetrahydrofuran solution (20 mL) of 4-nitrobenzyl bromide (4.6 g, 22 mmol) was added at the same temperature, and the mixture was gradually heated to 0° C. After the reaction, the mixture was added with a saturated aqueous ammonium chloride solution (100 mL), extracted with ethyl acetate (200 mL), and the organic phase was washed with a saturated brine (100 mL), and dried over anhydrous magnesium sulfate. The dried organic phase was filtered, and the filtrate was concentrated under reduced pressure, and the resultant residue was purified through silica gel column chromatography (n-hexane:ethyl acetate (v/v)=2:1) to thereby obtain N-{5-[2-(4(S)-benzyl-2-oxooxazolidine-3-yl)-1(S)-(4-nitrobenzyl)-2-oxoethyl]-2-methoxyphenyl}-N-isobutyl-2,2-dimethylpropionic acid amide (yield: 6.9 g, yield ratio: 68%).

$^1$H-NMR (CDCl$_3$) δ value: 0.85 (6H, d, J=6.6 Hz), 0.97-1.02 (9H, m), 1.71 (1H, m), 2.71 (1H, dd, J=9.6, 13.5 Hz), 3.17 (2H, dd, J=3.3, 13.5 Hz), 3.53 (1H, dd, J=7.6, 13.5 Hz), 3.79 (3H, s), 3.99-4.09 (3H, m), 4.56 (1H, br s), 5.33 (1H, br s), 6.83 (1H, d, J=8.3 Hz) 7.06-7.37 (9H, m), 8.11 (2H, d, J=8.5 Hz).

FABMS: 616 (M+H)$^+$.

A methanol solution (120 mL) of thus obtained N-{5-[2-(4(S)-benzyl-2-oxooxazolidine-3-yl)-1(S)-(4-nitrobenzyl)-2-oxoethyl]-2-methoxyphenyl}-N-isobutyl-2,2-dimethylpropionic acid amide (6.9 g, 11 mmol) was added with 10 wt % of palladium/carbon (0.69 g), and the mixture was stirred under a hydrogen atmosphere (1 kg/cm²) for 6 hours. After the reaction, any insoluble matter was removed by filtration, the filtrate was concentrated under reduced pressure, and the resultant residue was purified through silica gel column chromatography (n-hexane:ethyl acetate (v/v)=2:1) to thereby obtain N-{5-[l(S)-(4-aminobenzyl)-2-(4(S)-benzyl-2-oxooxazolidine-3-yl)-2-oxoethyl]-2-methoxyphenyl}-N-isobutyl-2,2-dimethylpropionic acid amide (yield: 5.4 g, yield ratio: 83%).

A 1,2-dichloroethane solution (100 ml) of thus obtained N-{5-[1(S)-(4-aminobenzyl)-2-(4(S)-benzyl-2-oxooxazolidine-3-yl)-2-oxoethyl]-2-methoxyphenyl}-N-isobutyl-2,2-dimethylpropionic acid amide (5.4 g, 9.3 mmol) was added with 2,6-dichlorobenzoyl chloride (2.7 mL, 19 mmol) and triethylamine (3.9 mL, 28 mmol) at 0° C., and the mixture was stirred at room temperature for 12 hours. After the reaction, the mixture was added with chloroform (100 mL), and the solution was washed successively with an aqueous saturated sodium hydrogen carbonate solution (100 mL), aqueous 1N-hydrochloric acid solution (100 mL) and saturated brine (100 mL), and dried over anhydrous magnesium sulfate. The dried organic phase was filtered, and the filtrate was concentrated under reduced pressure to thereby obtain N-[4-(3-(4(S)-benzyl-2-oxooxazolidine-3-yl)-2(S)-{3-[(2,2-dimethylpropionyl)isobutylamino]-4-methoxyphenyl}-3-oxopropyl)phenyl]-2,6-dichlorobenzamide (yield: 6.4 g, yield ratio: 91%).

A mixed solvent of tetrahydrofuran (60 mL) and distilled water (20 mL) was added with a 2 mol/L aqueous lithium hydroxide solution (4.5 mL, 8.8 mmol) and 30 wt % of hydrogen peroxide (3.9 mL, 35.2 mmol) at 0° C., and the mixture was further added with a tetrahydrofuran (30 mL) solution of N-[4-(3-(4(S)-benzyl-oxooxazolidine-3-yl)-2(S)-{3-[(2,2-dimethylpropionyl)isobutylamino]-4-methoxyphenyl}-3-oxopropyl)phenyl]-2,6-dichlorobenzamide (3.3 g, 4.4 mmol), and was then stirred for 30 minutes. After the reaction, the solution was added with a saturated aqueous sodium hydrogen sulfite solution (42 mL) and a 10 wt % aqueous citric acid solution (33 mL), stirred for 30 minutes, extracted with ethyl acetate (100 mL×2), and the extract was dried over anhydrous magnesium sulfate. The dried organic phase was filtered, the filtrate was concentrated under reduced pressure, and the resultant residue was purified through silica gel column chromatography (n-hexane:ethyl acetate (v/v)=2:1) to thereby obtain 3-[4-(2,6-dichlorobenzoyl amino)phenyl]-2(S)-{3-[(2,2-dimethylpropionyl) isobutyl amino]-4-methoxyphenyl}propionic acid (yield: 1.3 g, yield ratio: 50%).

$^1$H-NMR (DMSO-$d_6$) δ value: 0.74-0.89 (15H, m), 1.60 (1H, br s), 2.40-2.66 (1H, m), 2.97 (1H, m), 3.29 (1H, m), 3.77 (3H, s), 3.80-3.91 (2H, m), 7.03 (2H, d, J=8.6 Hz), 7.09-7.21 (2H, m), 7.32 (1H, m), 7.48-7.57 (5H, m), 10.60 (1H, s), 12.42 (1H, s).

FABMS: 599 (M+H)$^+$.

$[α]_D$=+98.8

Example 500

Preparation of 3-[4-(2,6-dichlorobenzoyl amino) phenyl]-2(R)-{3-[(2,2-dimethylpropionyl)isobutyl amino]-4-methoxyphenyl}propionic acid 3-[4-(2,6-Dichlorobenzoyl amino)phenyl]-2(R)-{3-[(2,2-dimethylpropionyl)isobutylamino]-4-methoxyphenyl} propionic acid was synthesized similarly to as described in Example 499 except that (R)-4-benzyl-2-oxazolidinone was used in place of (S)-4-benzyl-2-oxazolidinone.

$^1$H-NMR (DMSO-$d_6$) δ value: 0.74-0.89 (15H, m), 1.58 (1H, m), 2.40-2.62 (1H, m), 2.95 (1H, m), 3.24 (1H, dd, J=6.6, 14.2 Hz), 3.77 (3H, s), 3.84-3.90 (2H, m), 7.03 (2H, d, J=6.6 Hz), 7.09-7.12 (2H, m), 7.33 (1H, m), 7.45-7.60 (5H, m), 10.61 (1H, s), 12.42 (1H, s).

FABMS: 599 (M+H)$^+$.

$[α]_D$=−80.6

[VLA-4/VCAM-1 Cell Adhesion Inhibition Test]

The compound of the present invention was examined for inhibition activity against adhesion between Chinese hamster ovary cell (CHO cell) transfected with human VCAM-1 gene and human promyelocyte-like cell line HL-60 exhibiting VLA-4, using a method described below.

VCAM-1-expressing CHO cells were placed in a 96-well cuture plate in an amount of 7×10$^3$ cells/well, and were cultured in Ham's F-12 medium containing 10 vol % fetal calf serum (FCS) for 3 days until a confluent state was satisfied. HL-60 cells were re-flotated in Hanks' solution containing 0.4 wt % bovine serum albumin (BSA), and fluorescence-labeled by adding 5 µM of 2',7'-bis(carboxyethyl)-5(6)-carboxy fluorescein pentaacetoxymethyl ester (BCECF-AM). The BCECF-labeled HL-60 cells were re-flotated in a FCS-free RPMI1640 medium in an amount of 4×10$^6$ cells/mL, and each 180 µL of the cell suspension was added with 20 µL of a solution of the individual test substance having various concentrations, and incubated at 37° C. for 15 minutes for pretreatment.

Thus-pretreated HL-60 cells were then stratified in an amount of 2×10$^5$ cells/well in each well containing the cultured VCAM-1-expressing CHO cells, and allowed to adhere at 37° C. for 5 minutes. The plate was filled with a 0.4 wt % BSA Hanks' solution, covered with a plate sealer, turned upside down, and the cells were further cultured for 45 minutes. The cells were washed, destroyed by adding PBS containing 1 vol % NP-40, and fluorescence intensity of the obtained supernatant was measured using a fluorescence measurement system (Millipore, Model cyto Fluor 2300).

Blank experiment was based on fluorescence intensity of PBS containing 1 vol % NP-40. Standard experiment was carried out using the fluorescence-labeled HL-60 suspensions having a concentration of 2×10$^5$, 10$^5$, 2×10$^4$ and 10$^4$ cells/mL, respectively, where the suspensions were added to PBS containing 1 vol % NP-40, the cells were destroyed, and the fluorescence intensities of the obtained supernatant were measured.

The above-described measurement was carried out for each test substance, and the number of cells adhered to the VCAM-1-expressing CHO cell added with the control or test substances was counted based on an analytical curve prepared based on the standard measurement. Inhibition ratio (%) for cell adhesion was estimated using the equation below:

Inhibition ratio (%) for cell adhesion
=100×[1−(the number of adhered cell in the test group)/ (the number of adhered cell in the control group)].

Fifty-percent inhibition concentration of the individual test substances estimated by the present test were shown in Table 22.

TABLE 22

| Example No. | 50% Inhibition Concentration (nM) |
|---|---|
| 1 | 85 |
| 2 | 48 |
| 3 | 3300 |
| 4 | 940 |
| 5 | 54 |
| 6 | 1000 |
| 7 | 930 |
| 8 | 650 |
| 9 | 7100 |
| 10 | 100 |
| 11 | 620 |

TABLE 22-continued

| Example No. | 50% Inhibition Concentration (nM) |
|---|---|
| 12 | 140 |
| 13 | 5300 |
| 14 | 1700 |
| 15 | 1100 |
| 16 | 680 |
| 17 | 7000 |
| 18 | 1700 |
| 19 | 1700 |
| 20 | 580 |
| 27 | 6000 |
| 28 | 7500 |
| 29 | 11000 |
| 30 | 73 |
| 32 | 14 |
| 35 | 8.6 |
| 37 | 0.85 |
| 38 | 2 |
| 39 | 2.4 |
| 40 | 0.5 |
| 41 | 1.7 |
| 46 | 1200 |
| 48 | 620 |
| 55 | 24 |
| 56 | 34 |
| 57 | 3.1 |
| 58 | 0.25 |
| 59 | 1.2 |
| 60 | 0.11 |
| 62 | 66 |
| 64 | 17 |
| 65 | 17 |
| 66 | 22 |
| 67 | 44 |
| 68 | 5.5 |
| 73 | 65 |
| 74 | 11 |
| 75 | 0.12 |
| 76 | 0.65 |
| 77 | 0.1 |
| 78 | 0.1 |
| 80 | 9.9 |
| 86 | 21 |
| 87 | 1.7 |
| 88 | 18 |
| 89 | 11 |
| 90 | 3.8 |
| 91 | 11 |
| 92 | 8.4 |
| 93 | 1.1 |
| 94 | 9.8 |
| 95 | 0.62 |
| 97 | 4.9 |
| 98 | 0.1 |
| 99 | 48 |
| 100 | 4.9 |
| 101 | 23 |
| 102 | 0.4 |
| 103 | 16 |
| 106 | 4100 |
| 117 | 3300 |
| 120 | 160 |
| 124 | 29 |
| 126 | 5700 |
| 130 | 17000 |

The results of LPAM-1/VCAM-1 adhesion inhibition test using the compounds of Example 38, 39, 106, 108, 499 and 500 showed the inhibition activity.

INDUSTRIAL AVAILABILITY

The present invention can provide novel 2,3-diphenylpropionic acid derivatives or salts thereof having an excellent oral absorptivity and in vivo behavior, having an antagonistic action against VLA-4 and/or LPAM-1, and are useful for treating or preventing diseases mediated by VLA-4 and/or LPAM-1. The present invention can provide also a VLA-4 and/or LPAM-1 antagonist or medicine which is useful as a remedy or prophylactic for diseases caused by adhesion and infiltration of leukocytes, or those mediated by VLA-4 and/or LPAM-1 in which VLA-4 and/or LPAM-1-dependent adhesion process play a certain role.

What is claimed is:

1. A 2,3-diphenylpropionic acid derivative or a salt thereof represented by general formula (1) below:

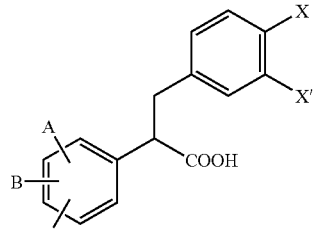

Formula (1)

where, A, B and C independently represent a hydrogen atom, halogen atom, nitro, cyano, hydroxy, carboxy, $C_{1-15}$ alkyl group, $C_{6-10}$ aryl group, heteroaryl group, $C_{1-15}$ alkoxy group, $C_{6-10}$ aryloxy group, heteroaryloxy group, $C_{2-16}$ alkoxycarbonyl group, $C_{7-11}$ aryloxycarbonyl group, heteroaryloxycarbonyl group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, $C_{1-15}$ alkylsulfonyl group, $C_{6-10}$ arylsulfonyl group, heteroarylsulfonyl group, $C_{1-15}$ alkylsulfinyl group, $C_{6-10}$ arylsulfinyl group, heteroarylsulfinyl group, $-NR^1R^2$, $-NR^1COR^2$, $-NR_1SO_2R^2$, $-NR^1CONR^2R^3$ or $-CONR^1R^2$, where $R^1$, $R^2$ and $R^3$ independently represent a hydrogen atom, $C_{1-15}$ alkyl group, $C_{2-15}$ alkenyl group, $C_{1-15}$ alkoxy group, $C_{6-10}$ aryl group, $C_{6-10}$ aryloxy group, heteroaryloxy group or heteroaryl group; either $R^1$ and $R^2$ or $R^2$ and $R^3$ may respectively form a ring; said ring may additionally contain at least one ring-composing atom selected from oxygen atom, nitrogen atom and sulfur atom; said ring may contain a double bond; and said ring may have a substituent; any two of A, B and C bound on the adjacent carbon atoms may form a benzene ring or a methylenedioxy ring; provided that, if A, B, or C is a heteroaryl group or comprises a heteroaryl group, the heteroaryl group is selected from the group consisting substituted or non-substituted, thienyl, dimethylpyrrole, benzothiazolyl and benzofuryl, and

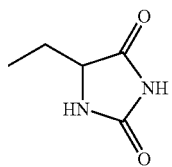 and 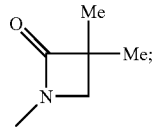

X and X' independently represent a hydrogen atom, halogen atom, nitro, cyano, hydroxy, carboxy, $C_{1-15}$ alkyl group, $C_{2-15}$ alkenyl group, $C_{2-15}$ alkynyl group, $C_{6-10}$ aryl group, heteroaryl group, $C_{1-15}$ alkoxy group, $C_{6-10}$ aryloxy group, heteroaryloxy group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, $-NR^4R^5$, $-NR^4COR^5$, $-NR^4SO_2R^5$, $-NR^4CONR^5R^6$, $-OCONR^4R^5$ or $-CONR^4R^5$, where, $R^4$, $R^5$ and $R^6$ independently represent a hydrogen atom, $C_{1-15}$ alkyl group, $C_{2-15}$ alkenyl group, $C_{6-10}$ aryl group, $C_{1-15}$ alkoxy group, $C_{6-10}$ aryloxy group, heteroaryloxy group or heteroaryl group; either $R^4$ and $R^5$ or $R^5$ and $R^6$ may form a ring; said ring may additionally contain at least one ring-composing atom selected from oxygen atom, nitrogen atom and sulfur atom; said ring may contain a double bond; and said ring may have a substituent; wherein at least one of X and X' in the general formula (1) is represented by a formula (2) below:

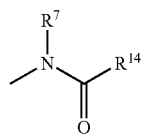

Formula (2)

where $R^7$ represents a hydrogen atom or $C_{1-15}$ alkyl group, and $R^{14}$ represents either of groups represented by general formulae (6) and (7);

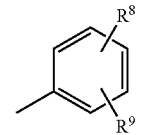

Formula (6)

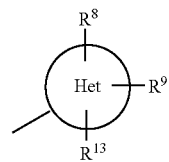

Formula (7)

where $R^8$ and $R^9$ independently represent a hydrogen atom, halogen atom, nitro, cyano, hydroxyl, carboxy, $C_{1-15}$ alkyl group, $C_{6-10}$ aryl group, $C_{1-15}$ alkoxy group, $C_{6-10}$ aryloxy group, heteroaryloxy group, $C_{2-16}$ alkoxycarbonyl group, $C_{2-16}$ alkanoyl group, $C_{7-11}$ aroyl group, heteroaroyl group, $C_{2-16}$ alkylcarbonyloxy group, $C_{7-11}$ arylcarbonyloxy group, heteroarylcarbonyloxy group, $C_{1-15}$ alkylthio group, $C_{6-10}$ arylthio group, heteroarylthio group, $C_{1-15}$ alkylsulfonyl group, $C_{6-10}$ arylsulfonyl group, heteroarylsulfonyl group, $C_{1-15}$ alkylsulfinyl group, $C_{6-10}$ arylsulfinyl group, heteroarylsulfinyl group, $-NR^{10}R^{11}$, $-NR^{10}COR^{11}$, $-NR^{10}SO2R^{11}$, $-NR^{10}CONR^{11}R^{12}$ or $-CONR^{10}R^{11}$, where $R^{10}$, $R^{11}$ and $R^{12}$ independently represent a hydrogen atom, $C_{1-15}$ alkyl group, $C_{2-15}$ alkenyl group, $C_{1-15}$ alkoxy group, $C_{6-10}$ aryl group, $C_{6-10}$ aryloxy group, heteroaryloxy group or heteroaryl group, either $R^{10}$ and R11 or $R^{11}$ and $R^{12}$ may form a ring; said ring may additionally contain at least one ring-composing atom selected from oxygen nitrogen atom and sulfur atom; said ring may contain a double bond; and said ring may have a substituent; Het represents an aromatic heterocycle containing at least one atom selected from nitrogen atom, oxygen atom and sulfur atom; and $R^{13}$ represents a hydrogen atom or $C_{1-15}$ alkyl group.

2. The 2,3-diphenylpropionic acid derivative or the salt thereof according to claim 1, wherein at least one of A, B and C in the formula (1) represents $-NR^1R^2$, $-NR^1COR^2$, $-NR^1SO_2R^2$ or $-NR^1CONR^2R^3$.

3. The 2,3-diphenylpropionic acid derivative or the salt thereof according to claim 1, wherein at least one of A, B and C in the formula (1) represents a $C_{1-15}$ alkyl group, $C_{1-15}$ alkoxy group, $C_{6-10}$ aryl group, heteroaryl group or $C_{2-16}$ alkoxycarbonyl group.

4. The 2,3-diphenylpropionic acid derivative or the salt thereof according to claim 1, wherein at least one of A, B and C in the formula (1) represents a halogen atom, cyano or $C_{1-15}$ alkylthio group.

5. The 2,3-diphenylpropionic acid derivative or the salt thereof according to claim 1, wherein "A" represents $-NR^1COR^2$ substituted at the 3-position; and X' represents a hydrogen atom.

6. The 2,3-diphenylpropionic acid derivative or the salt thereof according to claim 1, wherein "A" represents $-NR^1COR^2$ substituted at the 3-position; B represents a $C_{1-15}$ alkyl group or $C_{1-15}$ alkoxy group substituted at the 4- or 5-position; X' represents a hydrogen atom.

7. A pharmaceutical composition comprising as an active ingredient the 2,3-diphenylpropionic acid derivative or the salt thereof as set forth in claim 1.

8. A cell adhesion inhibitor comprising as an active ingredient the 2,3-diphenylpropionic acid derivative or the salt thereof as set forth in claim 1.

9. An α4 integrin inhibitor comprising as an active ingredient the 2,3-diphenylpropionic acid derivative or the salt thereof as set forth in claim 1.

10. A VLA 1 and/or LPAM-1 antagonist comprising as an active ingredient the 2,3-diphenylpropionic acid derivative or the salt thereof as set forth in claim 1.

* * * * *